(12) United States Patent
Zhao et al.

(10) Patent No.: US 7,273,845 B2
(45) Date of Patent: Sep. 25, 2007

(54) POLYMERIC PRODRUGS OF VANCOMYCIN

(75) Inventors: Hong Zhao, Edison, NJ (US); Richard B. Greenwald, Somerset, NJ (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 534 days.

(21) Appl. No.: 10/705,743

(22) Filed: Nov. 11, 2003

(65) Prior Publication Data

US 2004/0136947 A1    Jul. 15, 2004

Related U.S. Application Data

(60) Provisional application No. 60/425,892, filed on Nov. 12, 2002.

(51) Int. Cl.
 *A61K 38/16*   (2006.01)
 *A61K 38/14*   (2006.01)
(52) U.S. Cl. .......................................... 514/8; 530/322
(58) Field of Classification Search .................... None
See application file for complete search history.

(56) References Cited

U.S. PATENT DOCUMENTS 5,681,811 A    10/1997   Ekwuribe 6,395,266 B1 *   5/2002   Martinez et al. ........... 424/78.3

FOREIGN PATENT DOCUMENTS

WO        WO97/04796         2/1997
WO        WO 03/040211 A2    5/2003

OTHER PUBLICATIONS

Yuichi Ohya, et al., Synthesis and Cytotoxic Activity of Conjugates of Monomethoxy-Poly-(ethylene glycol) End-Capped with Doxorubicin *via* Ester, Amide, or Schiff's Base Bond, Journal of Bioactive and Compatible Polymers, vol. 10-Jan. 1995 pp. 51-66.

* cited by examiner

*Primary Examiner*—Anish Gupta
*Assistant Examiner*—Thomas S. Heard
(74) *Attorney, Agent, or Firm*—Lucas & Mercanti, LLP

(57) ABSTRACT

Methods of preparing vancomycin-polymer conjugates are disclosed. In preferred aspects, polymer residues which are preferably releasable, are selectively attached to the sugar amino and/or N-methyl amino groups of vancomycin and related compounds. Vancomycin-polymer conjugates made by the methods and methods of treatment using the conjugates are also disclosed.

14 Claims, 9 Drawing Sheets

POLYMERIC PRODRUGS OF VANCOMYCIN

CROSS-REFERNCE TO RELATED APPLICATION

This application claims the benefit of priority from U.S. Provisional Patent Application Ser. No. 60/425,892, filed Nov. 12, 2002, the contents of which are incorporated herein by reference.

FIELD OF INVENTION

The present invention relates to polymeric derivatives of vancomycin. More particularly, the invention relates to select vancomycin derivatives in which the sugar amino group and/or the N-methyl amino group has been modified with a substantially non-antigenic polymer.

BACKGROUND OF THE INVENTION

Vancomycin is an antibiotic which was initially discovered in the 1950's, see U.S. Pat. No. 3,067,099. It is usually reserved for use in the treatment of severe gram positive infections such as those caused by *Staphylococcus aureus* and when traditional antibiotics have failed. Over the years, there have been several proposals for improving one or more attributes of vancomycin, usually by continuous infusion. In another example, prodrugs of vancomycin have been proposed as a way of increasing the solubility and circulating life of the drug.

Prodrugs include chemical derivatives of a biologically-active parent compound which, upon administration, will eventually liberate the active parent compound in vivo. The use of prodrugs allows the artisan to modify one or more properties such as the onset and/or duration of action of a biologically-active compound in vivo. Prodrugs are often biologically inert or substantially inactive forms of the active compound. The rate of release of the active drug is influenced by several factors including the rate of hydrolysis of the linker which joins the parent biologically active compound to the prodrug carrier.

Polymer conjugates of vancomycin have also been proposed as potential prodrugs. For example, commonly-assigned U.S. Pat. No. 6,180,095 discloses benzyl elimination (BE) systems as part of a tripartate polymer-based prodrug platform. These BE prodrug systems are designed inter alia to releasably attach polymers such as polyethylene glycol (hereinafter PEG) to hydroxyl or amine residues on small molecules. After administration to a patient, the prodrugs break down in a predictable fashion. First, the polymer portion hydrolyzes at a predictable, predetermined rate due to the presence of selected bifunctional linkers which contain the desired "trigger". Once the polymer portion has been hydrolyzed, the BE system is initiated or triggered by having a free phenol or aniline derivative and rapidly releases the parent compound. Commonly assigned U.S. Pat. Nos. 5,965,119 and 6,303,569 disclose related tripartate prodrug systems containing trimethyl lock triggers. The disclosure of each of the above-mentioned commonly-assigned patents is incorporated herein by reference.

In spite of the fact that vancomycin is listed among the various biologically active compounds having an available amino group for attachment of the prodrug platform in each of the foregoing commonly-assigned patents, further advances have been sought to refine and improve prodrugs of vancomycin. For example, unlike many biologically active compounds, vancomycin has two amino groups, i.e. the sugar amino ($V_3$) and N-methyl amino ($X_i$), which are available for polymeric substitution. Thus, control of the substitution reactions involving these amino groups is desirable. It has now been determined that it would be beneficial under certain circumstances to provide vancomycin polymer prodrugs which have the polymer attached substantially exclusively on one of the amino groups. It has further been discovered that other and further advantages are realized when a polymer is attached to both of the vancomycin amino groups. The present invention addresses such needs.

SUMMARY OF THE INVENTION

In one aspect of the invention, there is provided a method of preparing a vancomycin-polymer conjugates. The method includes reacting a vancomycin compound of the formula:

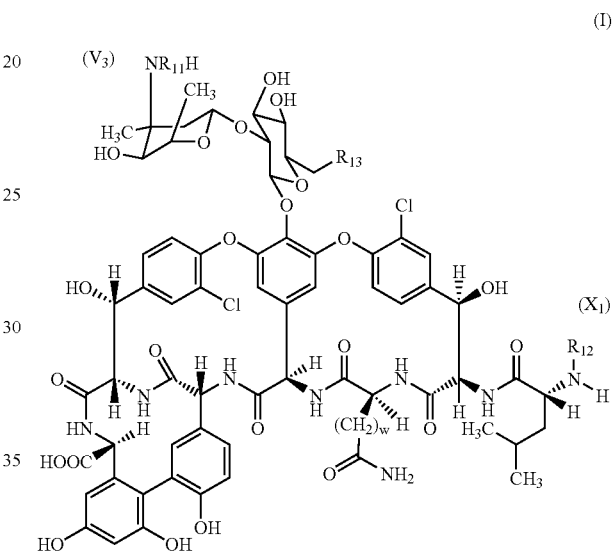

(I)

wherein:

$R_{11}$ and $R_{12}$ are each independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxys, phenoxys and $C_{1-6}$ heteroalkoxys;

$R_{13}$ is OH, NH-aryl, NH-aralkyl, NH-alkyl-aryl or NH—$C_{1-12}$ alkyl; and w is 1 or 2;

with a polymer residue containing at least one leaving group capable of reacting with the sugar amino group of a vancomycin compound in the presence of at least about a twenty-fold molar excess of triethylamine and a sufficient amount of dimethylformamide.

In a further aspect of the invention, a vancomycin-polymer conjugate is formed in which a polymer residue is attached on both the sugar amino and the N-methyl amino of the vancomycin compound. Specifically, the initial vancomycin-polymer conjugates are reacted with an activated polymer residue containing at least one leaving group capable of reacting with the N-methyl amino group of the vancomycin compound in the presence of at least about a 5 to 10 fold molar excess amount of dimethylaminopyridine (DMAP) and a sufficient amount of a solvent mixture comprising dichloromethane (DCM) and dimethylformamide (DMF).

In a still further aspect of the invention, there is provided an alternative method of preparing vancomycin-polymer conjugates in which a polymer conjugate is attached to both the sugar amino and the N-methyl amino groups. This method includes reacting a vancomycin compound of formula (I) as shown above with about 2 equivalents of a polymer residue containing at least one leaving group capable of reacting with the sugar amino group and the N-methyl amino group of the vancomycin compound in the presence of at least about a 5 to 10 fold molar excess amount of dimethylaminopyridine (DMAP) and a sufficient amount of a solvent mixture which contains dichloromethane (DCM) and dimethylformamide (DMF).

The present invention also includes the vancomycin-polymer conjugates made by the above-mentioned processes. Methods of treating mammals having conditions susceptible to vancomycin and related compound therapies are also provided.

Apart from the specific methods of the present invention, there are also provided vancomycin-polymer conjugates, including, for example:

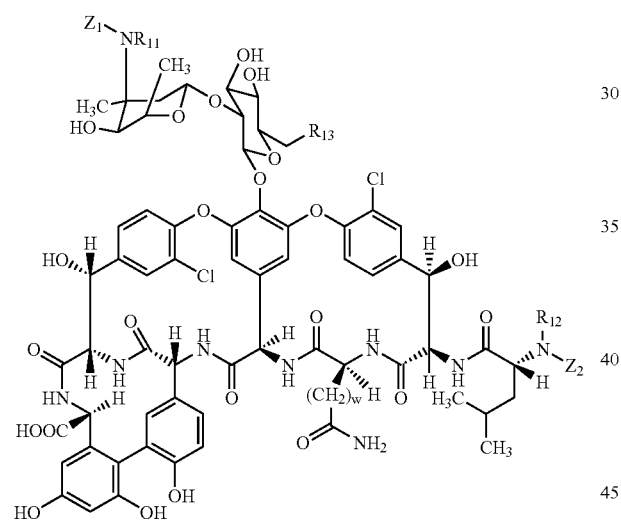

(II)

wherein:

$R_{11}$ and $R_{12}$ are each independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl and $C_{1-6}$ heteroalkoxys;

$R_{13}$ is OH, NH-aryl, NH-aralkyl, or NH—$C_{1-12}$ alkyl;

w is 1 or 2;

$Z_1$ is

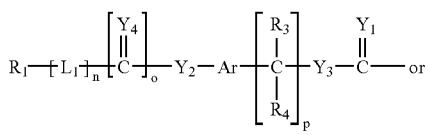

-continued

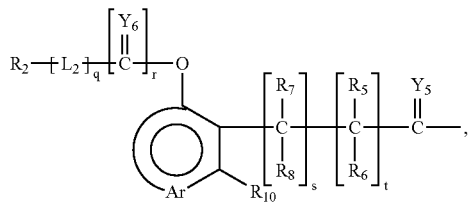

wherein $R_1$ and $R_2$ are independently selected polymeric residues;

$Y_{1-6}$ are independently selected from among O, S or $NR_9$;

$R_{3-10}$ are independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl, $C_{1-6}$ heteroalkoxys, $C_{1-6}$ haloalkyl, $C_{1-6}$ carboxyalkyl and $C_{1-6}$ hydroxyalkyl;

Ar is a moiety which forms a multi-substituted aromatic hydrocarbon or a multi-substituted heterocyclic group;

$L_1$ and $L_2$ are independently selected bifunctional linkers;

p and t are independently selected positive integers;

n, q and s are independently either zero or a positive integer;

o and r are independently zero or one; and $Z_2$ is

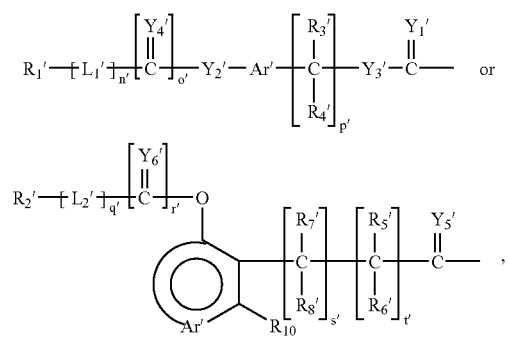

wherein $R_1'$ and $R_2'$ are independently selected polymeric residues;

$Y_{1-6}'$ are independently selected from among O, S or $NR_9'$;

$R_{3-10}'$ are the same or different and are each independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl, $C_{1-6}$ heteroalkoxys, $C_{1-6}$ haloalkyl, $C_{1-6}$ carboxyalkyl and $C_{1-6}$ hydroxyalkyl;

Ar' is a moiety which forms a multi-substituted aromatic hydrocarbon or a multi-substituted heterocyclic group;

$L_1'$ and $L_2'$ are independently selected bifunctional linkers;

p' and t' are independently selected positive integers;

n', q' and s' are independently either zero or a positive integer; and o' and r' are independently zero or one.

Further conjugates include those containing a vancomycin attached on each terminus of the polymer through the N-methyl amino group of the vancomycin.

For purposes of the present invention, the term "residue" shall be understood to mean that portion of a vancomycin compound, polymer, i.e. PEG, or bifunctional spacer which remains after it has undergone a substitution reaction with another compound.

Methods of preparing the compositions of the invention and methods of treatment using the same are also provided.

For purposes of the present invention, the term "polymeric containing residue" or "PEG residue" shall each be understood to mean that portion of the polymer or PEG which remains after it has undergone a reaction with a vancomycin compound such as those described herein as being of formula (I).

For purposes of the present invention, the term "alkyl" shall be understood to include straight, branched, substituted, e.g. halo-, alkoxy-, nitro-, $C_{1-2}$ alkyls, $C_{3-8}$ cycloalkyls or substituted cycloalkyls, etc. Positive integer shall mean an integer greater than or equal to one, preferably between 1 and 10 and more preferably 1.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo phenyl; aralkyls include moieties such as tolyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo shall be understood to include fluoro, chloro, iodo and bromo.

The term "sufficient amounts" for purposes of the present invention shall mean an amount which achieves a desired effect or therapeutic effect as such effect is understood by those of ordinary skill in the art.

An advantage of the compounds of the invention is that in certain preferred embodiments, the releasable polymer not only extends the circulating life of the vancomycin derivative, but it also provides a means for controlling the rate of hydrolysis of the derivative. Thus, the artisan has the ability to include varied substituents that allow for modulation of the rate- of hydrolysis of the prodrug to optimize the pK profile, reduce dose frequency and its related medical costs. The modifications described herein also allow one to maintain serum levels and prevent bacterial resistance of vancomycin from developing. Further, the conjugates of the present invention can be used on a prophylactic basis to provide protection against bacterial infection.

Other and further advantages will be apparent from the following description and drawings.

DETAILED DESCRIPTION OF THE INVENTION

Figure 1A:
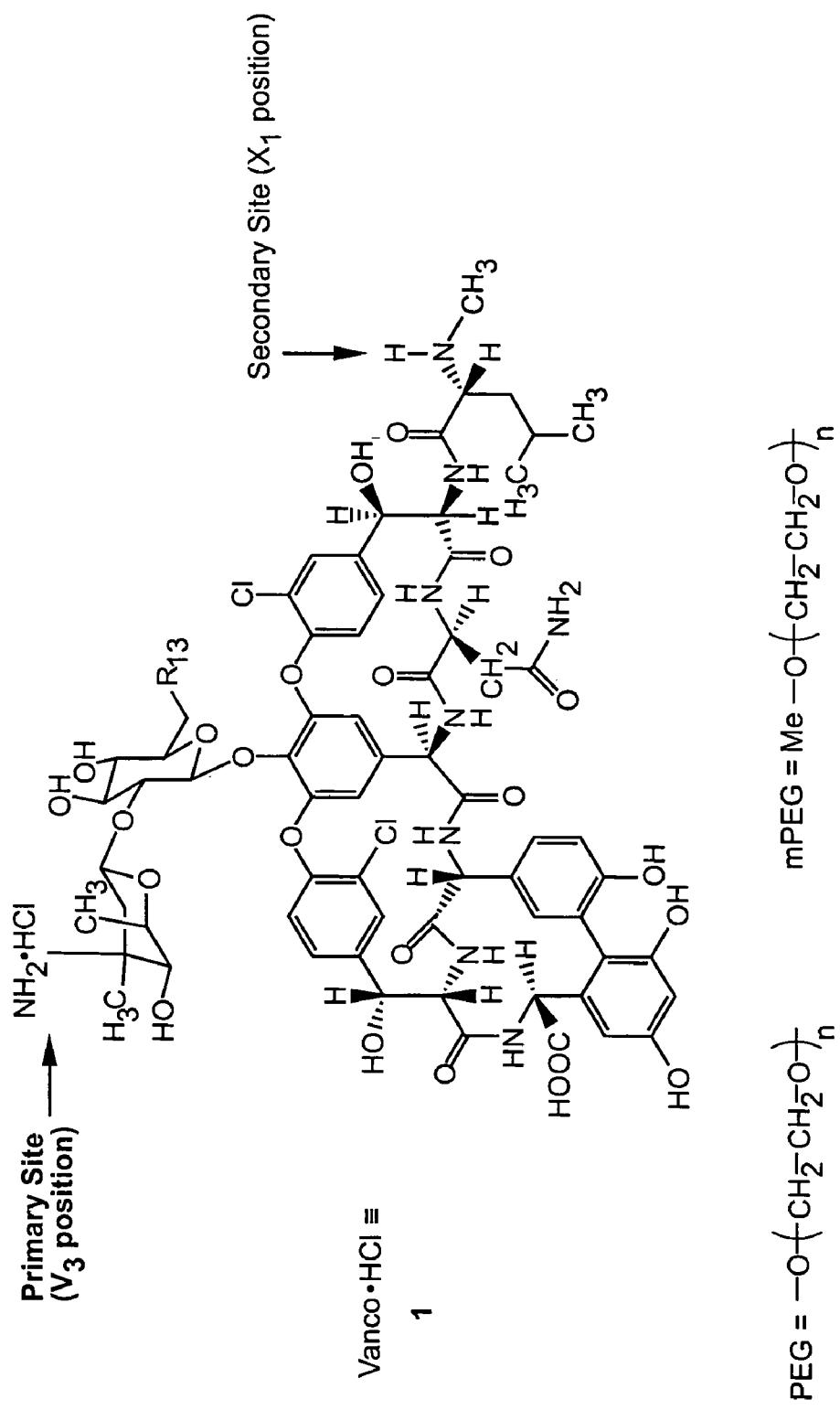
FIGS. 1-7 schematically illustrate methods of forming compounds of the present invention which are described in the Examples.

The vancomycin compounds of the present invention generally correspond to formula (I):

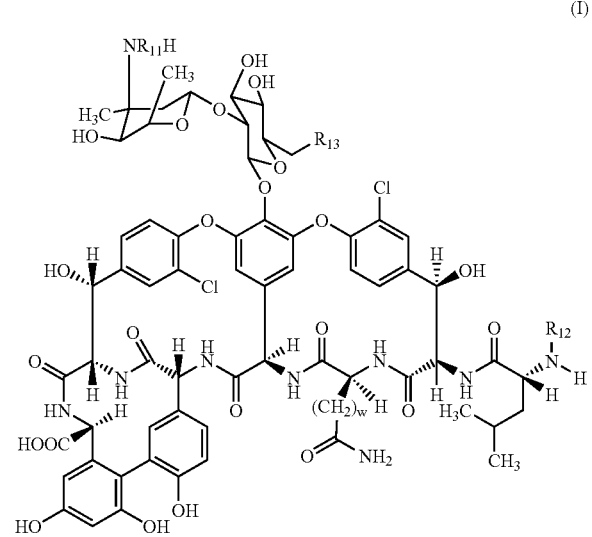

(I)

wherein:

$R_{11}$ and $R_{12}$ are independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxyalkyl, phenoxyalkyl, and $C_{1-6}$ heteroalkoxys;

$R_{13}$ is OH, NH-aryl, NH-aralkyl, or NH—$C_{1-12}$ alkyl; and w is 1 or 2.

$R_{11}$ is preferably hydrogen, $R_{12}$ is preferably methyl and $R_{13}$ is preferably OH. In alternative aspects of the invention, $R_{11}$ can be

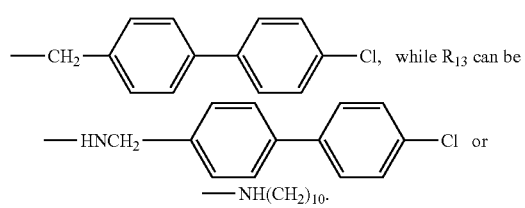

While the above formula covers many of the more well known vancomycin-type compounds known to have biological activity, it is to be understood that the invention embraces not only these specific compounds, but also those vancomycin-based compounds know to artisans of ordinary skill to have a sugar amino and/or an N-methyl amino group. For example, the inventive processes described herein can also be carried out with the vancomycin derivatives described in, for example, EP 0 201 251, "The Role of Hydrophobic Substituents in the Biological Activity of Gycopeptide Antibiotics", *J. Am. Chem Soc.* 2000, 122, 12608-12609 and U.S. Pat. Nos. 4,495,179, 3,067,099, 4,556,008, 4,548,925 and 4,547,488 to name but a few. The disclosure of each of the foregoing is incorporated herein by reference. In most preferred aspects of the invention, however, the vancomycin compound employed for the processes described herein is:

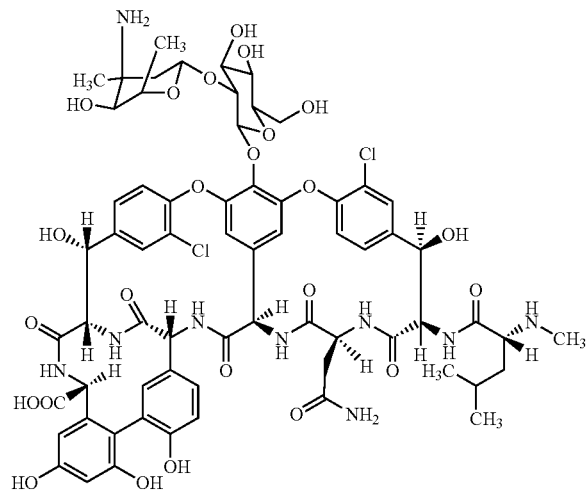

In accordance with a first aspect of the invention, methods are provided for preparing vancomycin-polymer conjugates by reacting a vancomycin compound of formula (I) as shown above with a polymer residue containing at least one leaving group capable of reacting with the sugar ($V_3$) amino group of a vancomycin compound in the presence of at least about a twenty-fold molar excess of triethylamine (TEA) and a sufficient amount of dimethylformamide (DMF). In even more preferred aspects of the invention, the reaction is also carried out in the presence of a molecular sieve.

Important aspects of this embodiment are the selection and amount of the base used in the reaction of the vancomycin compound with the activated polymer, e.g. the polymer residue containing the leaving group. Since the vancomycin compounds employed in the invention usually contain two amino groups, care must be taken during the reaction so as to avoid formation a heterogeneous mixture of vancomycin-polymer conjugates in which the polymer is attached at more than one of the sugar amino (hereinafter $V_3$) and/or N-methyl amino (hereinafter $X_1$). It has been surprisingly found that when the at least about 20 and preferably at least about 30 equivalents of TEA in combination with a sufficient amount of DMF, and in the presence of a sufficient amount of a molecular sieve of about 4 Å, are used, it is possible to obtain a substantially homogeneous reaction product of a vancomycin compound having a polymer linked thereto via the $V_3$ amino group.

For purposes of the present invention, the amount of the solvent DMF employed in the reaction is referred to as a "sufficient amount". As will be appreciated by those of ordinary skill, this amount will be an amount which is capable of at least dissolving the reactants. In most aspects of the invention, the amount of DMF employed will range from about 10 ml/g to about 500 ml/g and preferably from about 100 ml/g to about 200 ml/g based upon the vancomycin compound used. For purposes of the present invention, the reaction takes place at a temperature range of from about 15° C. to about 40° C. Preferably; the temperature range is from about 25° C. to about 35° C. with from about 30° C. to about 35° C. being most preferred.

The activated polymers which can be employed in this process are preferably selected from among compounds of the formulae:

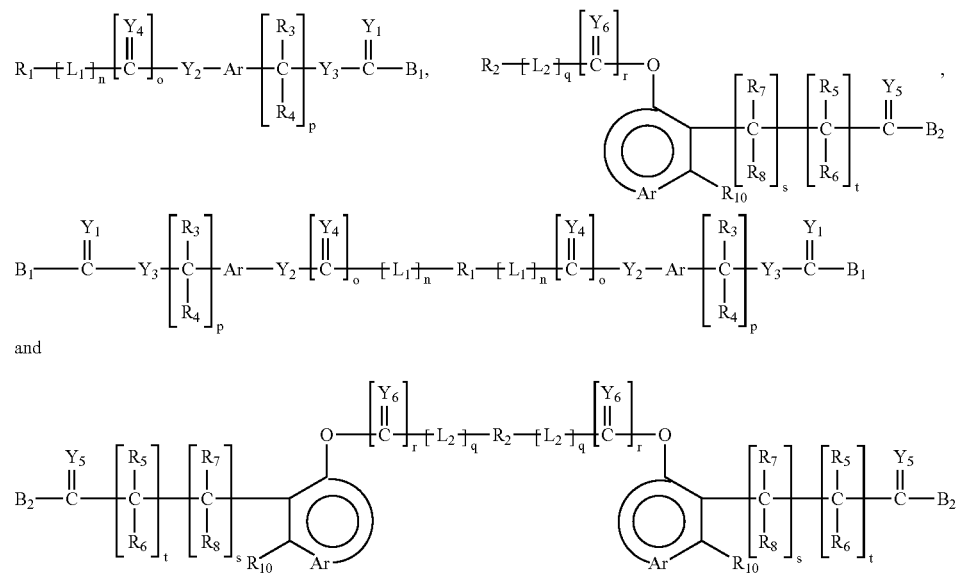

and wherein:

$R_1$ and $R_2$ are independently selected polymer residues;

$Y_{1-6}$ are O, S or $NR_9$;

$R_{3-10}$ are independently selected from among hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxys, phenoxys and $C_{1-6}$ heteroalkoxys;

Ar is a moiety which forms a multi-substituted aromatic hydrocarbon or a multi-substituted heterocyclic group;

$L_1$ and $L_2$ are independently selected bifunctional linkers;

$B_1$ and $B_2$ are independently selected leaving groups;

p and t are independently selected positive integers;

n, q and s are independently either zero or a positive integer; and o and r are independently zero or one.

For purposes of the present invention, the foregoing are also referred to as activated polymer linkers. The polymer residues are preferably polyalkylene oxide-based and more preferably polyethylene glycol (PEG) based wherein the PEG is either linear or branched.

Within this aspect of the invention, the following are preferred: $Y_{1-6}$ are O; $R_{3-10}$ are each independently either hydrogen or $C_{1-6}$ alkyls, with methyl and ethyl being the most preferred alkyls. $R_{10}$ is most preferably methyl, p, p', t and t' are each one; n, q and s are independently zero or one; o and r are independently zero or one. $L_{1-2}$ are preferably each selected from the non-limiting list consisting of:

—C(O)CH$_2$OCH$_2$—;    —NHC(CH$_3$)$_2$CH$_2$—;

—C(O)CH$_2$CH$_2$NR$_{14}$—;    —C(O)CH$_2$NR$_{14}$—;

—NHCH$_2$(CH$_3$)—;    —NHCH$_2$—;    —NHCH$_2$CH$_2$—;

—NHCH$_2$CH$_2$OCH$_2$CH$_2$O—;

—NHCH$_2$CH$_2$OCH$_2$CH$_2$OCH$_2$CH$_2$NR$_{14}$—    and

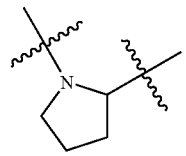

wherein $R_{14}$ is selected from the same group as that which defines $R_3$ above.

Referring now to the activated polymers described above, it can be seen that the Ar is a moiety which forms a multi-substituted aromatic hydrocarbon or a multi-substituted heterocyclic group. A key feature is that the Ar moiety is aromatic in nature. Generally, to be aromatic, the π electrons must be shared within a "cloud" both above and below the plane of a cyclic molecule. Furthermore, the number of π electrons must satisfy the Hückle rule (4n+2). Those of ordinary skill will realize that a myriad of moieties will satisfy the aromatic requirement of the moiety and thus are suitable for use herein. Some particularly preferred aromatic groups include:

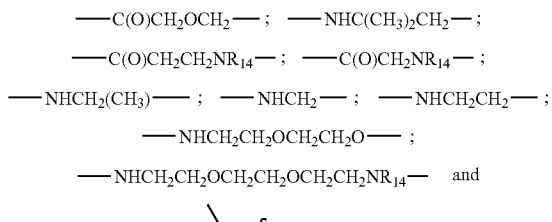

wherein $R_{15-20}$ are independently selected from the same group which defines $R_3$.

Other preferred aromatic hydrocarbon moieties include, without limitation

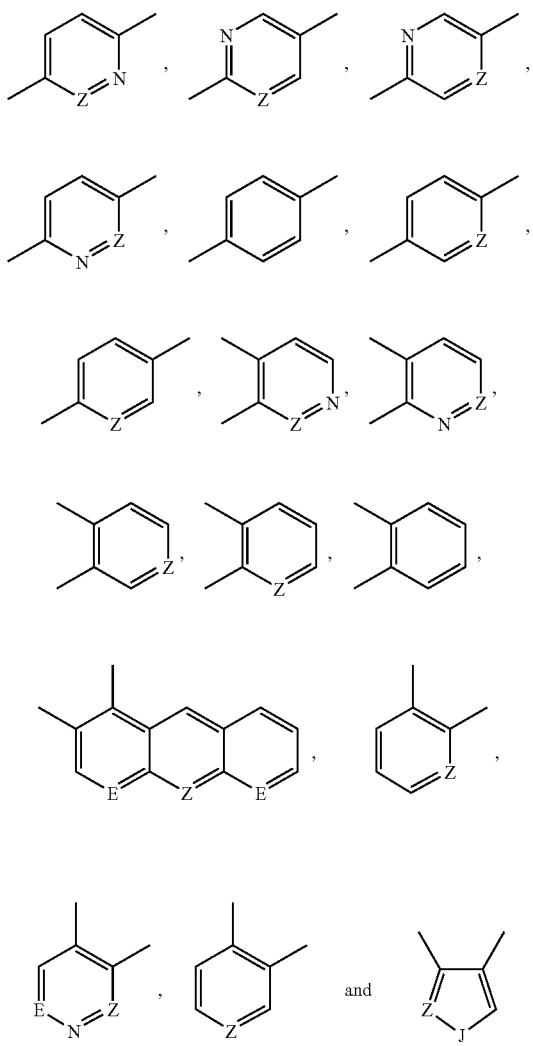

wherein Z and E are independently $CR_{21}$ or $NR_{22}$; and J is O, S or $NR_{23}$ where $R_{21-23}$ are selected from the same group at that which defines $R_3$ or a cyano, nitro, carboxyl, acyl, substituted acyl or carboxyalkyl. Isomers of the five and six-membered rings are also contemplated as well as benzo- and dibenzo-systems and their related congeners are also contemplated. It will also be appreciated by the artisan of ordinary skill that aromatic rings can optionally be substituted with heteroatoms such as O, S, $NR_{19}$, etc. so long as Hückel's rule is obeyed. Furthermore, the aromatic or heterocyclic structures may optionally be substituted with halogen(s) and/or side chains as those terms are commonly understood in the art.

In some preferred aspects of the invention, the activated polymer linkers are prepared in accordance with commonly-assigned U.S. Pat. Nos. 6,180,095, 5,965,119 and 6,303,569, the contents of which have already been incorporated herein by reference. Within this context, the following activated polymer linkers are preferred:

11                                               12
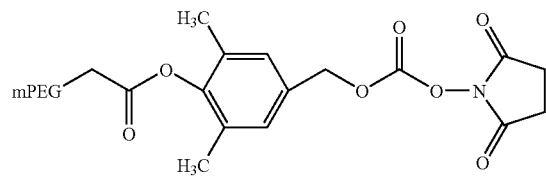
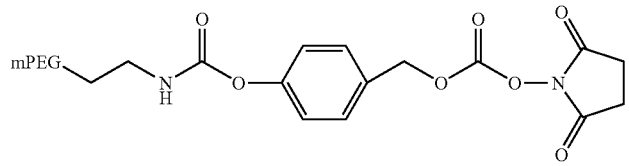
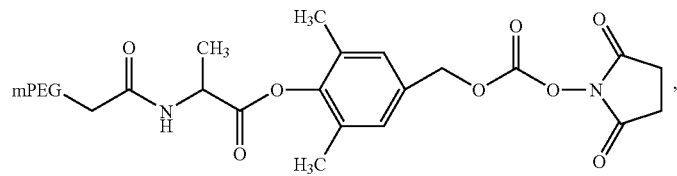
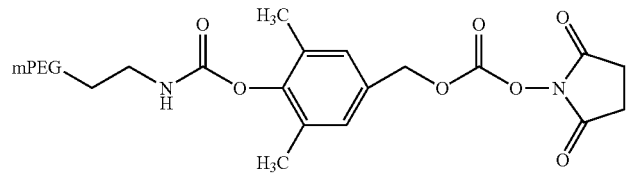
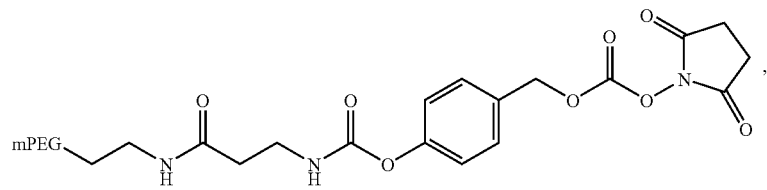
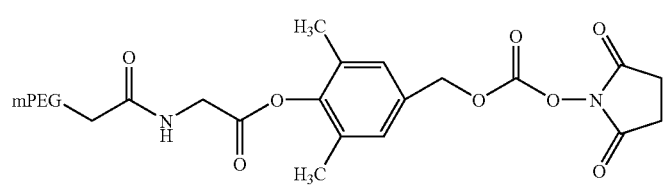
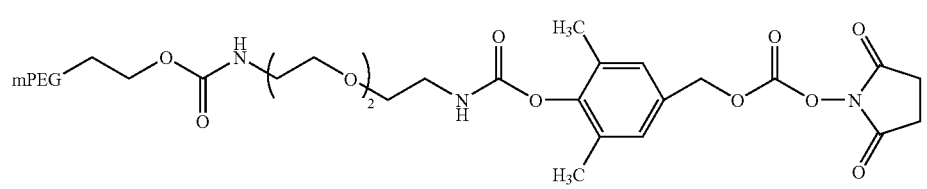
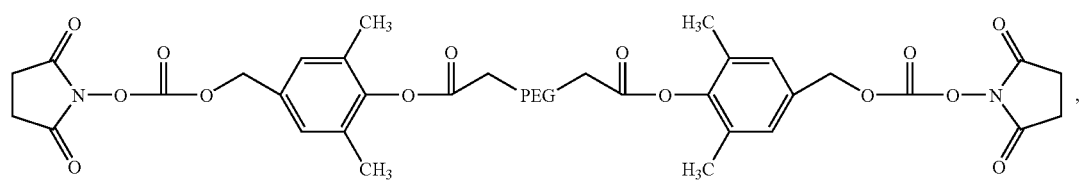
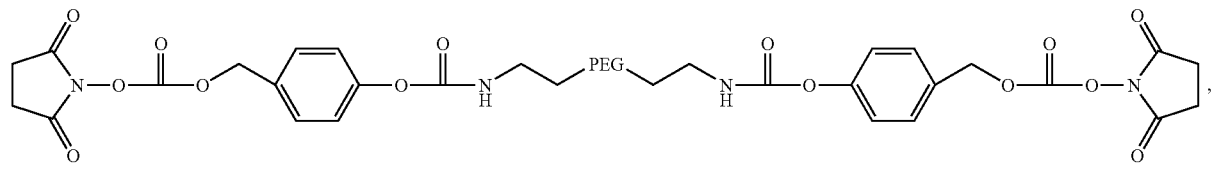
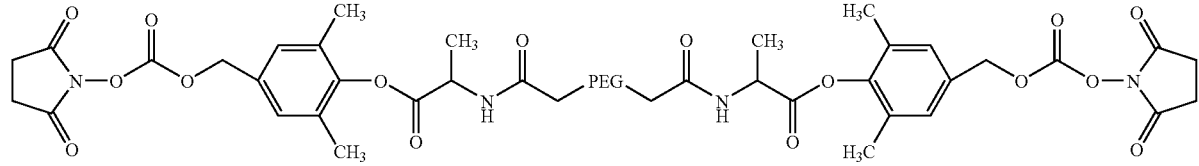

-continued

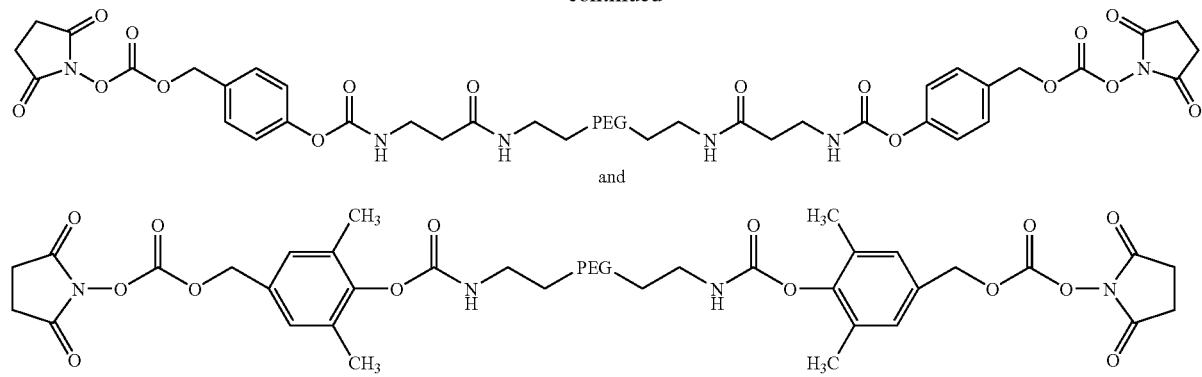

and

In one alternative aspect of the invention, the vancomycin polymer conjugates are made using certain branched or bicine polymer residues such as those described in commonly assigned U.S. patent application Ser. Nos. 10/218,167 and 10/449,849, the disclosure of each being incorporated herein by reference. Within this aspect of the invention, some preferred activated polymers are of the formulae:

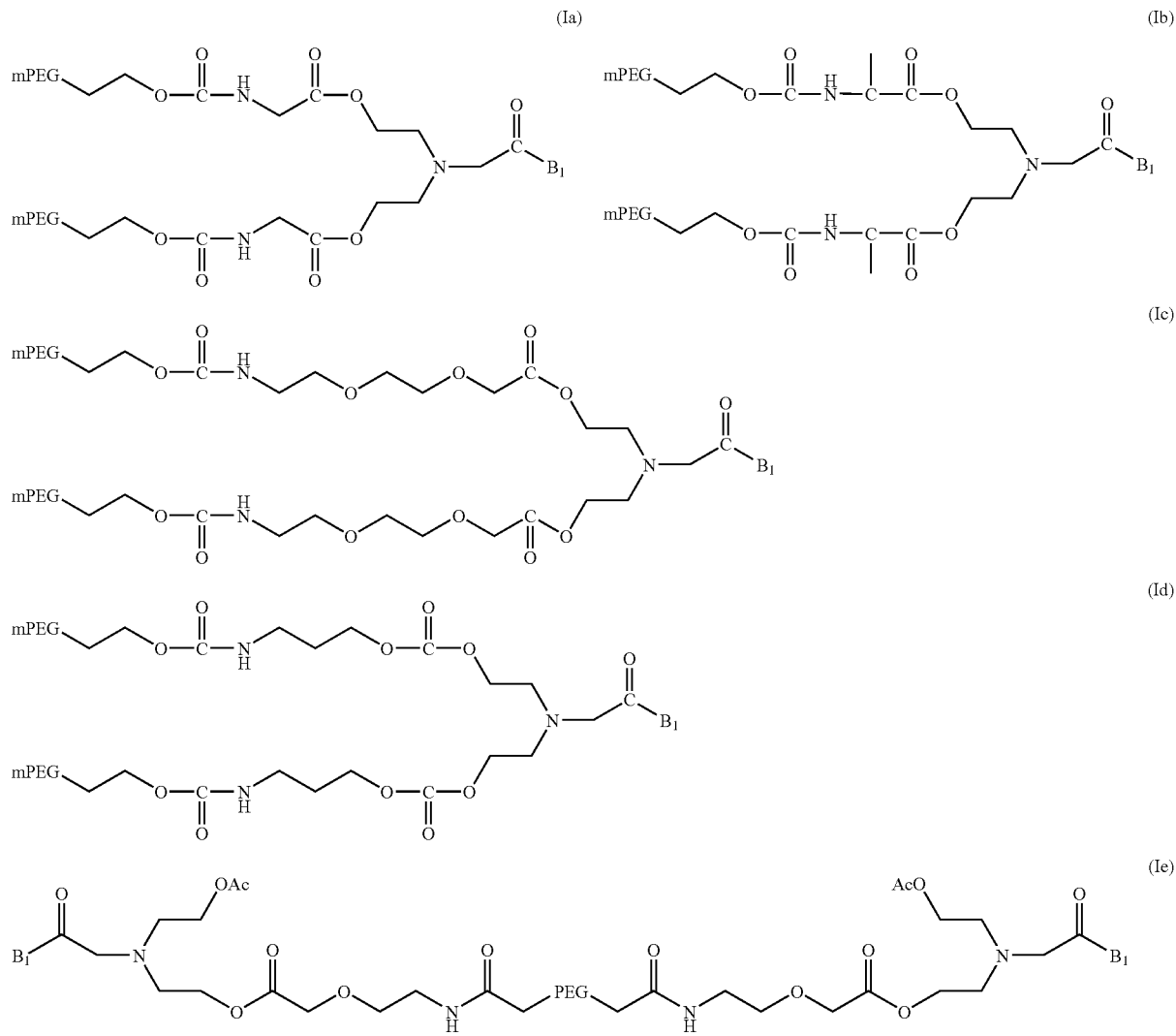

-continued
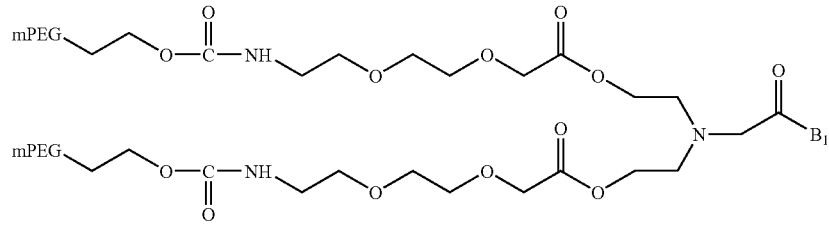
(If)
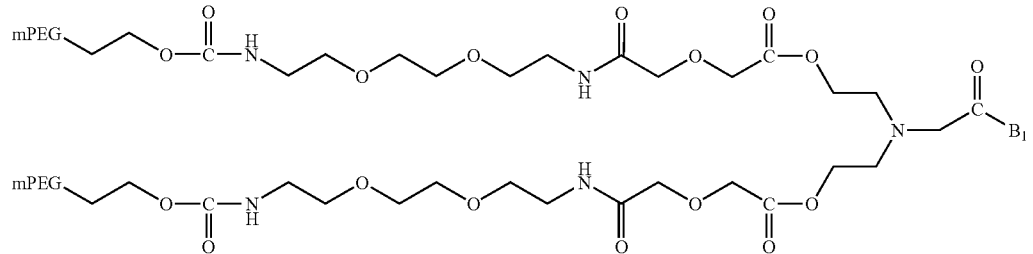
(Ig)
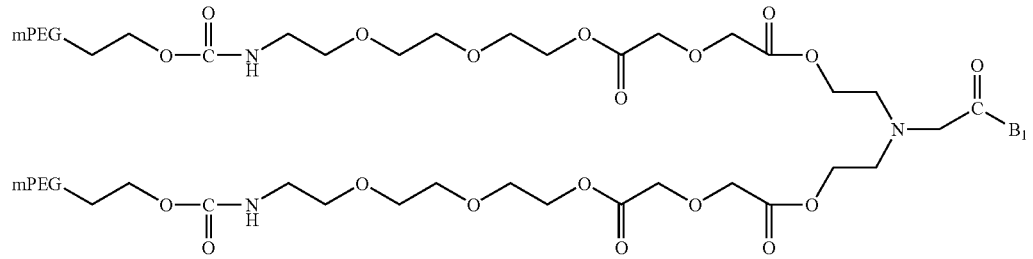
(Ih)
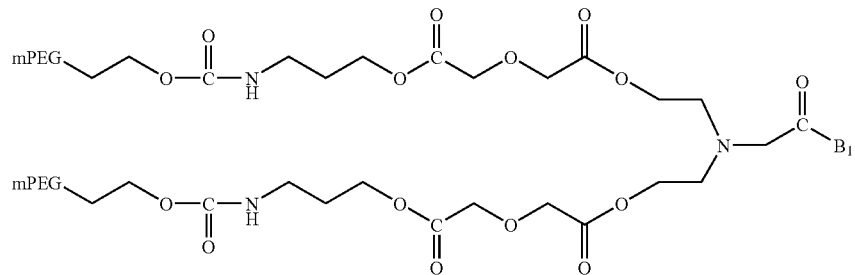
(Ii)
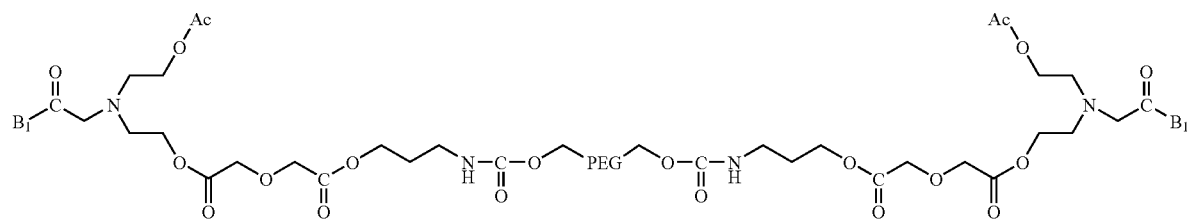
(Ij)
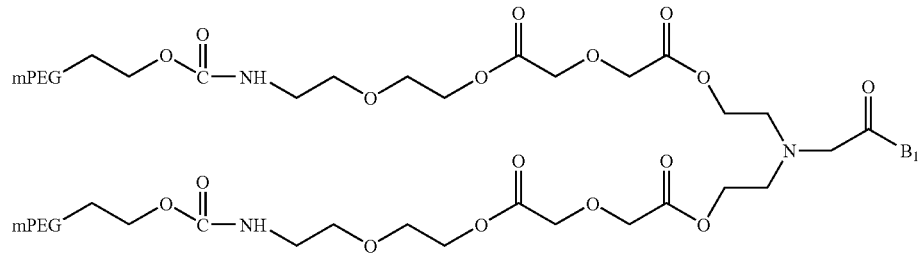
(Ik)

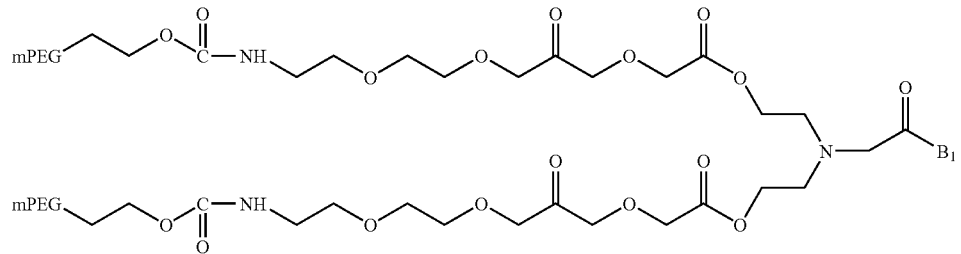
(Il)
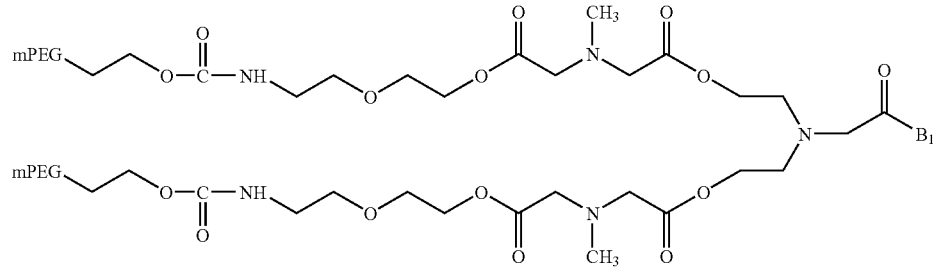
(Im)
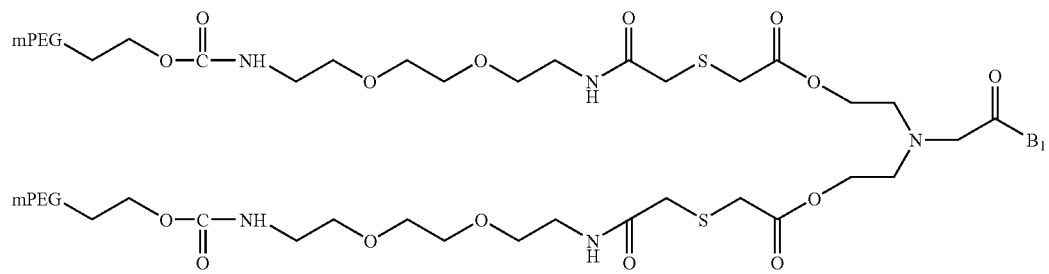
(In)
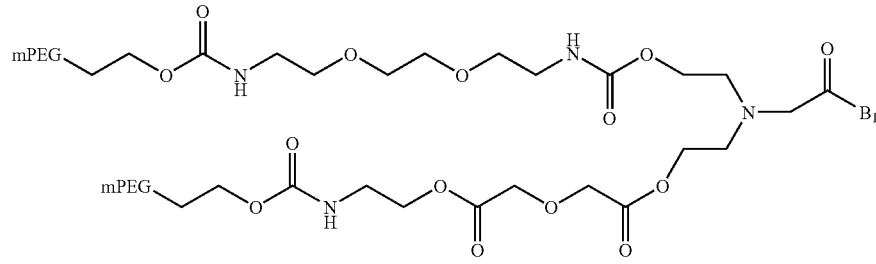
(Io)
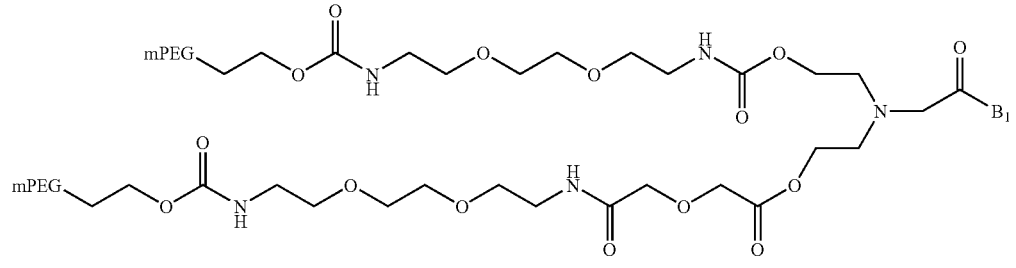
(Ip)
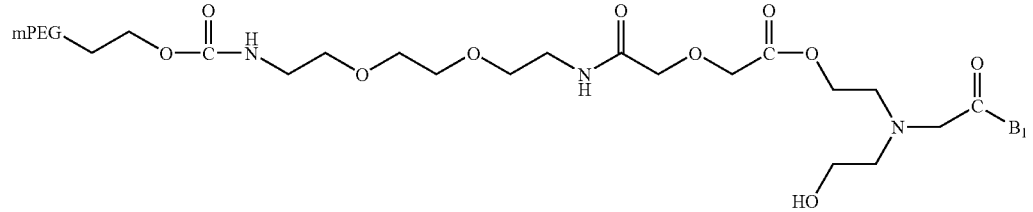
(Iq)

-continued

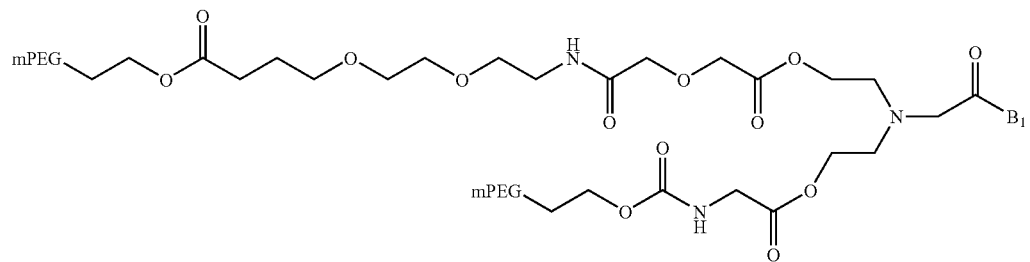
(Ir)

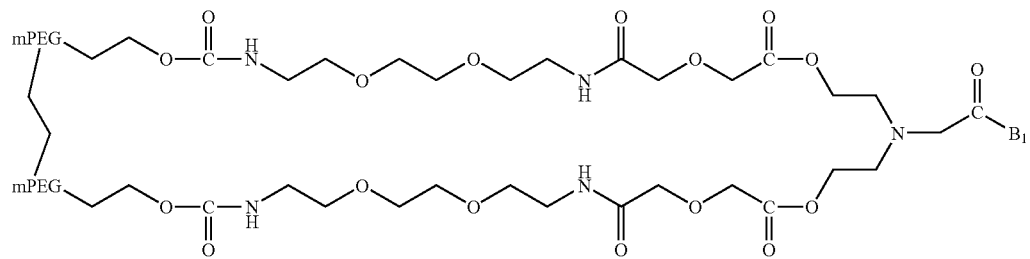
(Is)

where $B_1$ is a leaving or activating group such as:

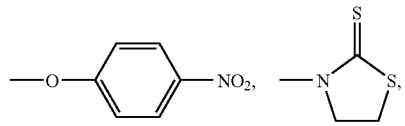

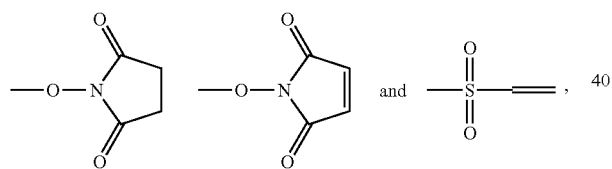 and or other suitable leaving or activating groups.

Reaction of the bicine-activated polymers with a suitable vancomycin-based target results in the transformation of the activated polymer into conjugates.

In alternative aspects, the activated polymer linkers are prepared using branched polymer residues such as those described commonly assigned U.S. Pat. Nos. 5,643,575; 5,919,455 and 6,113,906, the disclosure of each being incorporated herein by reference. Within this aspect of the invention, the activated polymers are of the formulae:

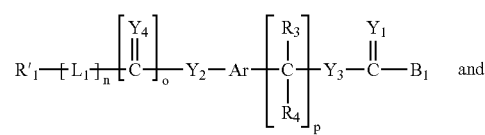 and

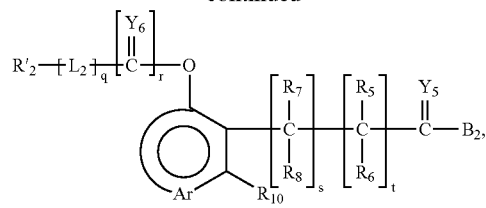

wherein $R'_1$ and $R'_2$ are branched PEG polymer residues such as

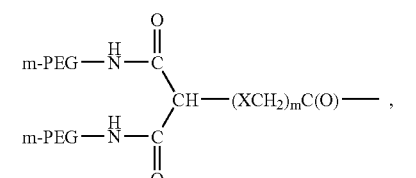

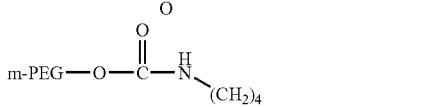

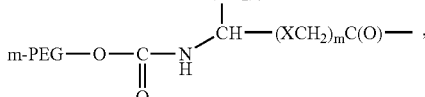

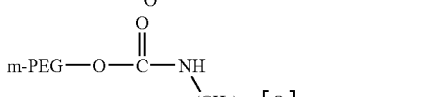

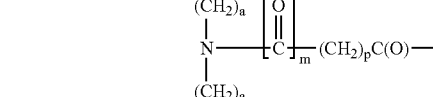

-continued

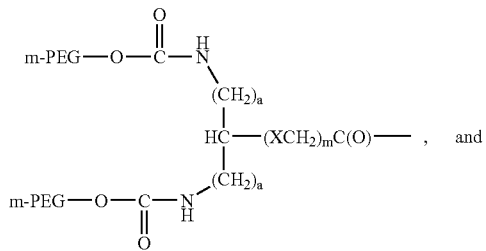

and

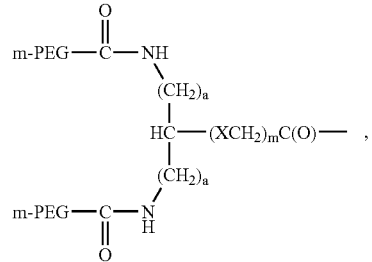

wherein (a) is an integer of from about 1 to about 5;

X is O, NQ, S, SO or SO$_2$; where Q is H, a C$_{1-8}$ alkyl, C$_{1-8}$ branched alkyl, C$_{1-8}$ substituted alkyl, aryl or aralkyl;

(m) is 0 or 1;

(p) is a positive integer, preferably from about 1 to about 6; and all other variables are as set forth above.

Some of the preferred vancomycin conjugates which result from reacting the vancomycin compounds with the activated polymer linkers corresponding to the above general formulae include:

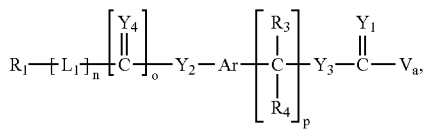 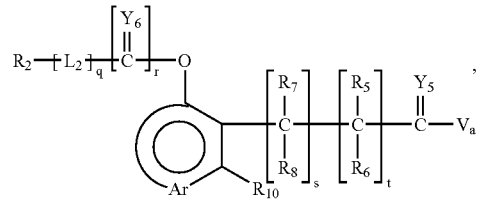

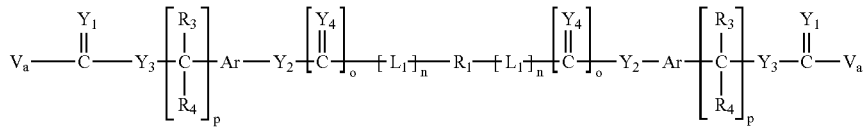

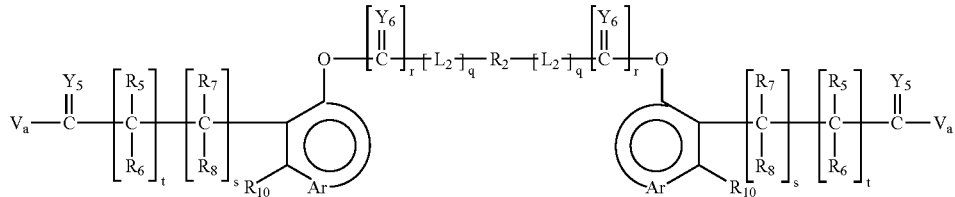

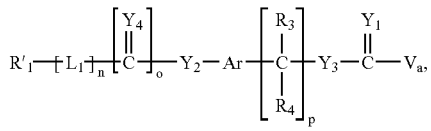 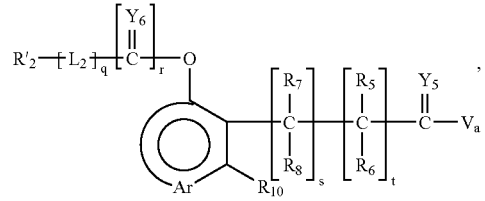

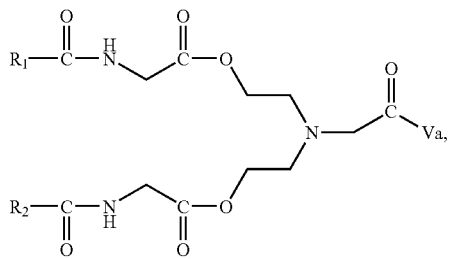 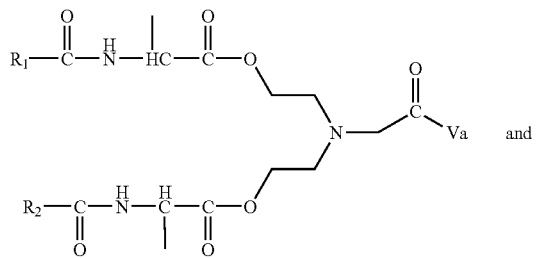

and

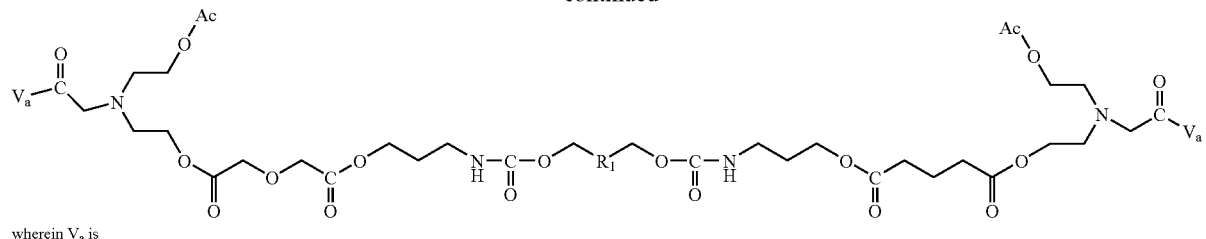
wherein $V_a$ is
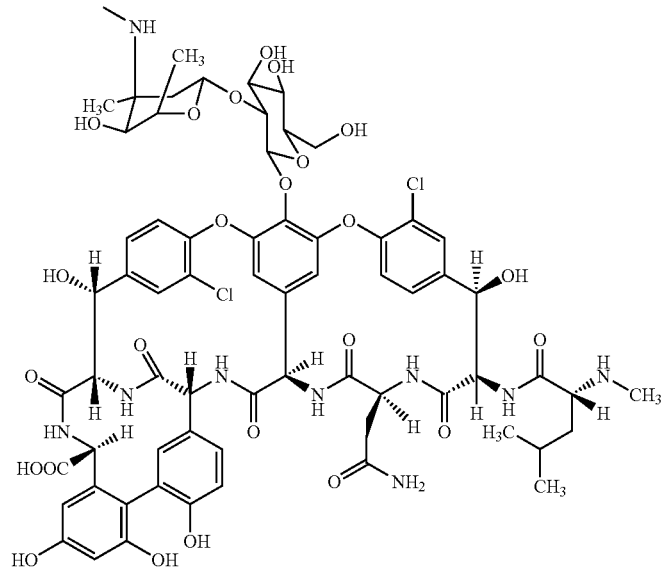
and all other variables are the same as that previously mentioned. More preferred $V_3$-linked polymer conjugates of the invention include:
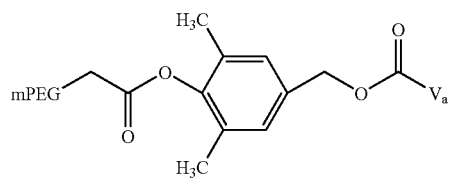
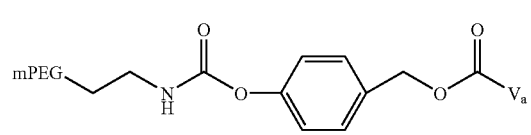
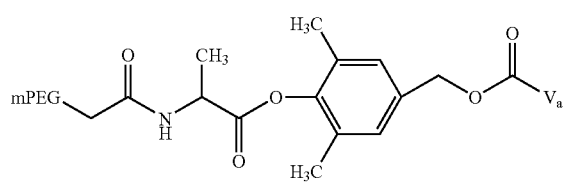
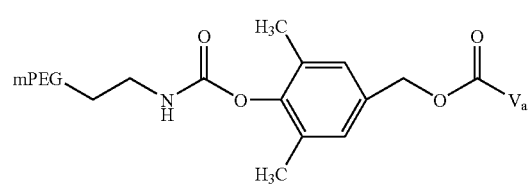
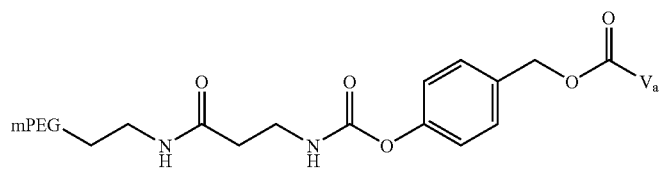
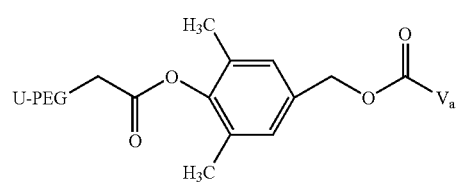

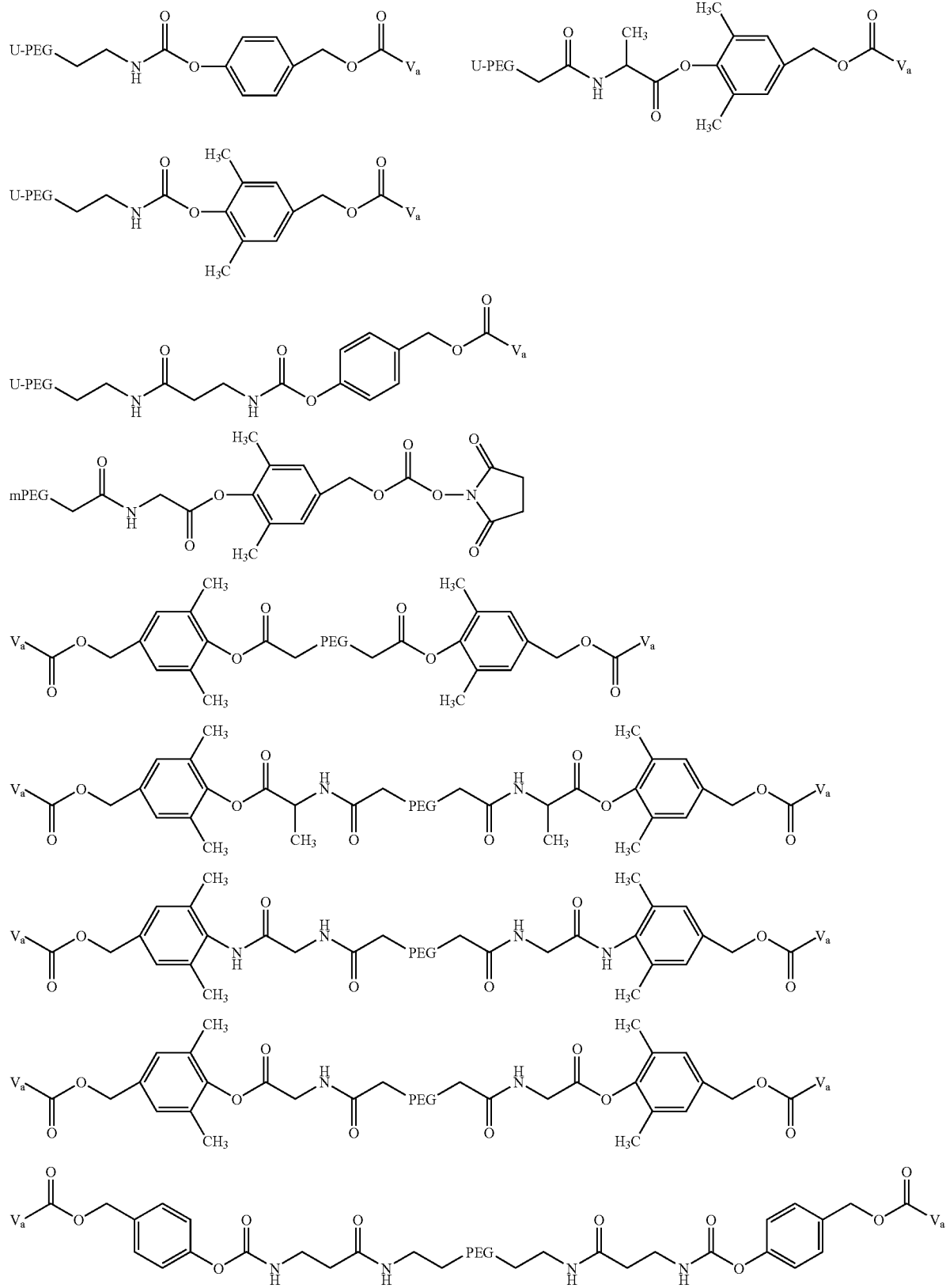

-continued
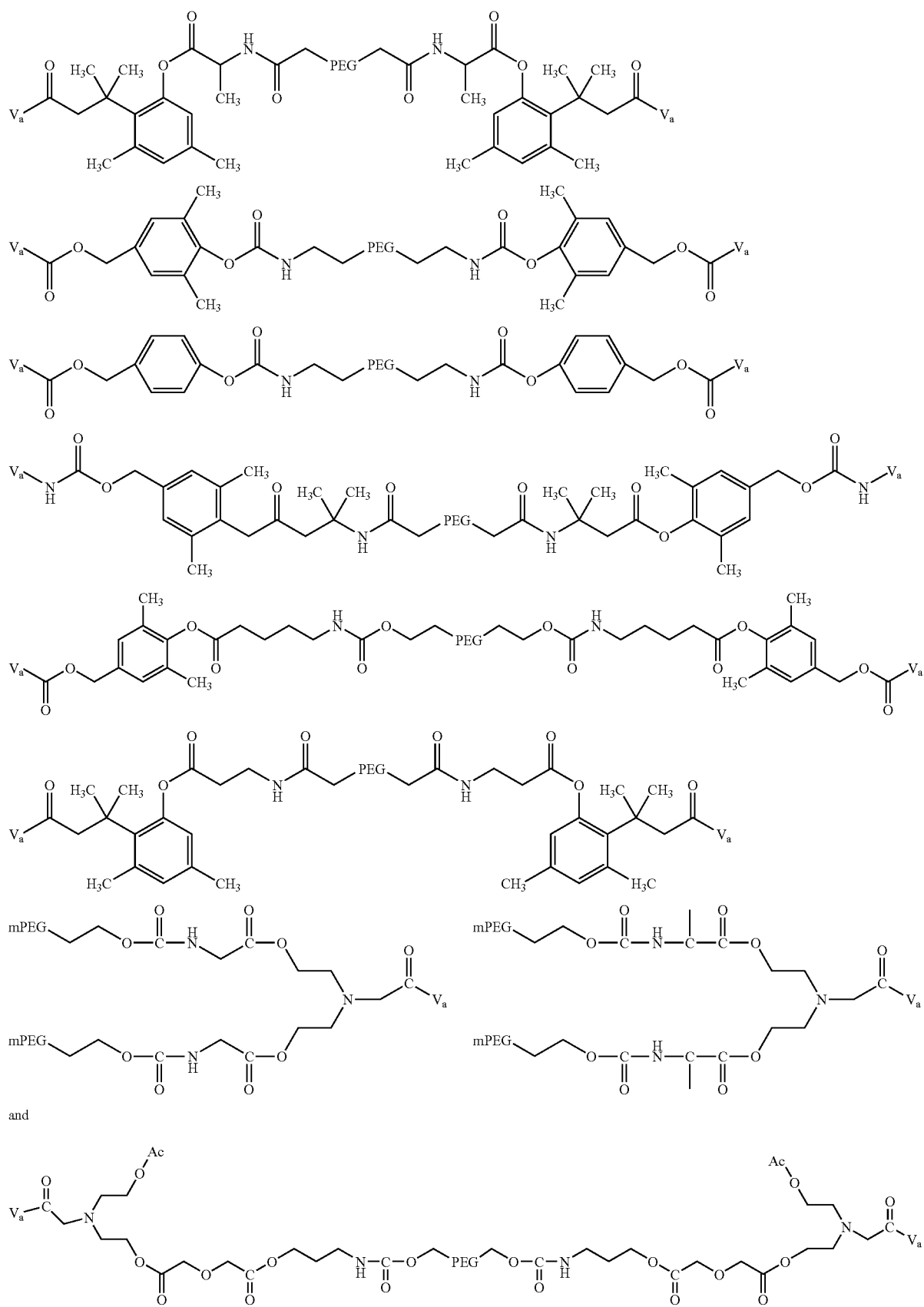
and wherein

PEG is —O(—CH$_2$CH$_2$O)$_x$—;

mPEG is H$_3$CO(—CH$_2$CH$_2$O)$_x$—;

x is a positive integer selected from about 10 to about 2300, and

U-PEG is one of the structures shown above in paragraph [0033] but more preferably the U-PEG conjugate is

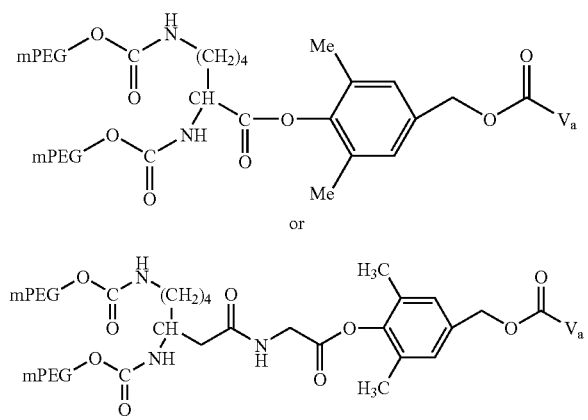

and V$_a$ is as shown above.

In a second aspect of the invention, the V$_3$-linked vancomycin conjugates are further modified to allow attachment of a second polymer to the vancomycin compound at the X$_1$ position. In carrying out this further reaction, it is preferred that the polymer residue portions, (whether linear or branched), of the activated polymer linkers, i.e. R$_1$, R'$_1$, R$_2$ and/or R'$_2$ are capped on non-activated end thereof. The polymer residues are described in detail below, however for purposes of describing this preferred embodiment, the polyethylene glycol (PEG) residue is usually capped on one end with a methyl group. Such PEG's are often referred to as mPEG's. The vancomycin conjugates therefore contain mPEG's attached on the V$_3$ position of the vancomycin.

This method therefore includes reacting the V$_3$-linked vancomycin-polymer conjugate with a second activated polymer linker which, in this case, comprises a polymer residue containing at least one leaving group capable of reacting with the N-methyl amino group of the V$_3$-linked vancomycin compound. This activated polymer linker may be the same as or different from that used to attach the polymer residue to the V$_3$ amino group. In certain preferred aspects of the invention, the polymer residue attached to the X$_1$ amino has a molecular weight which is greater than used for the polymer residue attached to the V$_3$ amino. Furthermore, the linkage selected for attachment of the polymer residue to the V$_3$ amino is, in certain preferred aspects, designed to hydrolyze more rapidly than that used to attach the polymer residue to the X$_1$ amino group. Further, by using a low molecular weight releasable polymer residue, or small molecular weight protecting group to attach to the sugar amino group (V$_3$), selective N-methyl amino derivatives can be obtained by removing the residue or protecting group from the sugar amino position once the N-methyl amino position (Z$_2$) has been derivatized. Moreover, as shown in the examples, the activated polymer used for linking the X$_1$ residue can be a bis-activated polymer so that two equivalents of vancomycin can be attached through the respective X$_1$ amino groups thereof. Once the X$_1$ amino group(s) has/have been derivitized, the V$_3$ modifications, e.g. mPEG linker or protecting groups can be hydrolyzed either in vitro in a PBS or similar buffer followed by purification or in vitro based upon enzyme degradation.

In order to prepare the vancomycin-polymer conjugate having a polymer residue attached on both the sugar amino and the N-methyl amino of the vancomycin compound, the reaction of the V$_3$-linked vancomycin compound with the second activated polymer linker is carried out in the presence of at least about a 5 fold molar excess amount of dimethylaminopyridine (DMAP) and a sufficient amount of a solvent which contains a mixture of dichloromethane (DCM) and dimethyl formamide (DMF). In preferred aspects, the amount of base is from about a 2 to about a 20 fold molar excess and in more preferred aspects, the amount of base is from about a 5 to about a 10 fold molar excess. The solvent mixture is preferably about equal parts dichloromethane and dichloroformamide although the ratio of solvents can range from about 3:1 to about 1:3.

Some preferred vancomycin-polymer conjugates having a polymer residue attached on the N-methyl amino group (X$_1$) are selected from among:

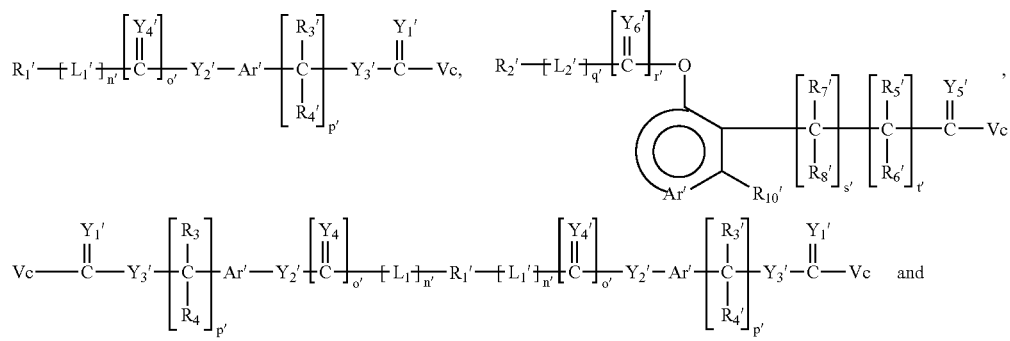

-continued

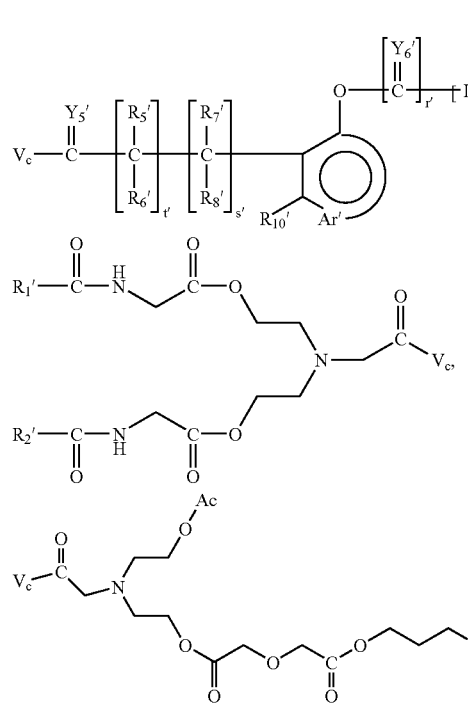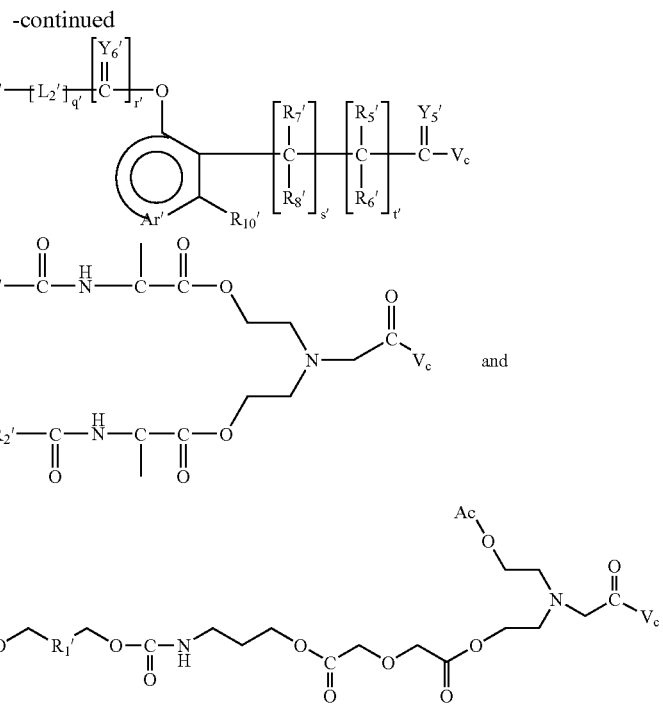

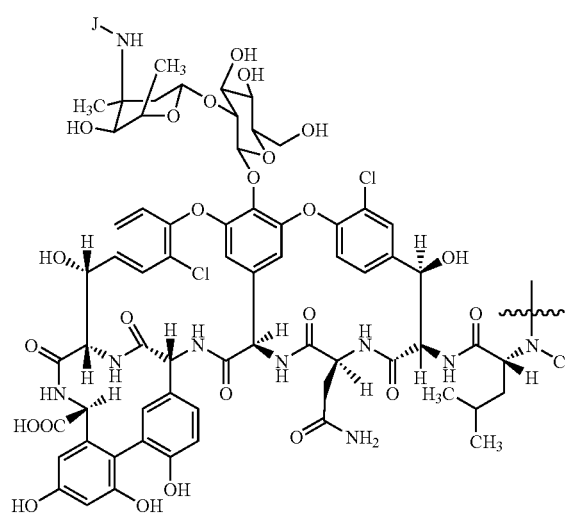

wherein

R₁' and R₂' are independently selected polymeric residues, which, in the non-bis-versions, include a capping group, e.g. methyl;

Vc is:

wherein J is H or selected from among polymer residues containing a capping group such as:

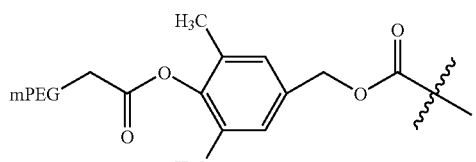

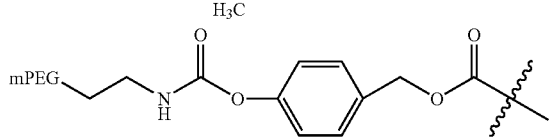

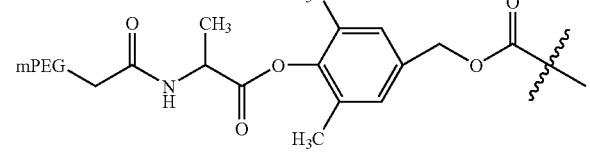

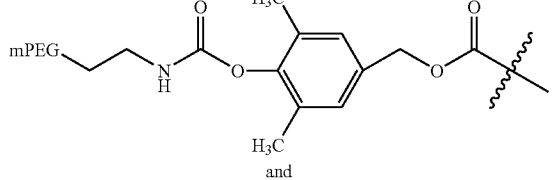

and

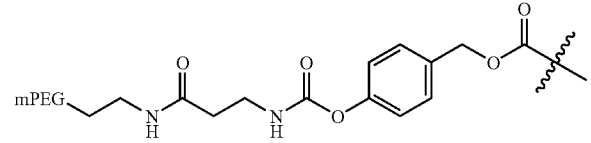

and all other variables are the same as that set forth above.

More specifically, certain preferred species corresponding to this aspect of the invention include:

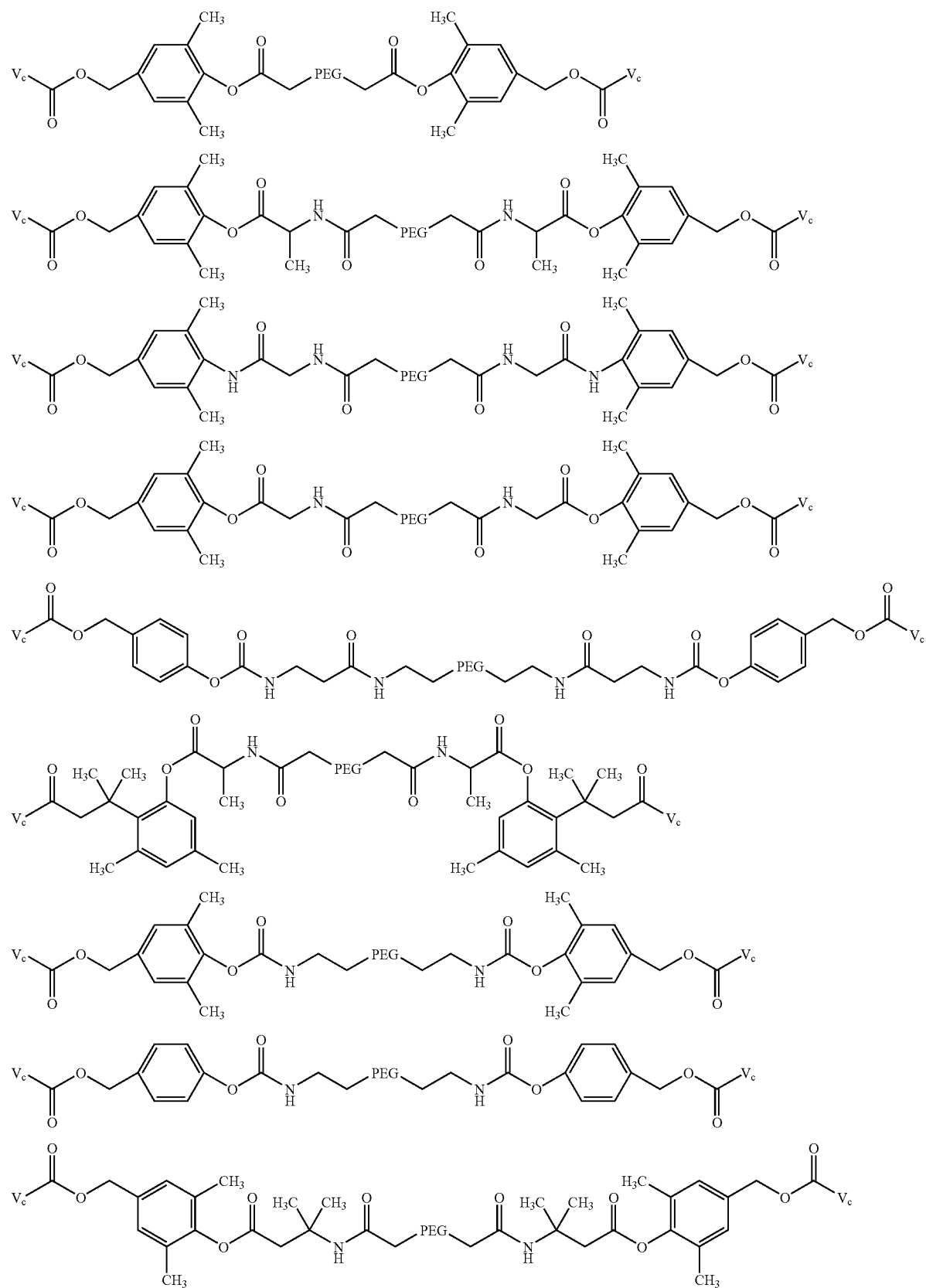

-continued

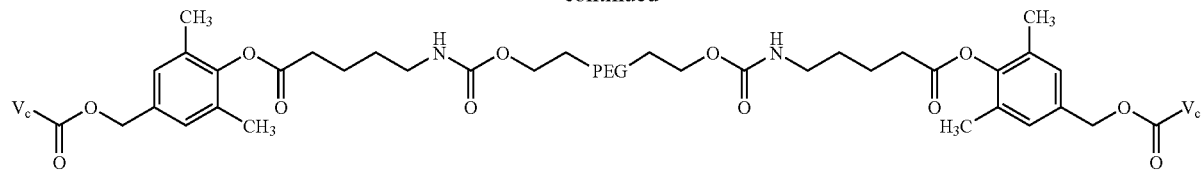

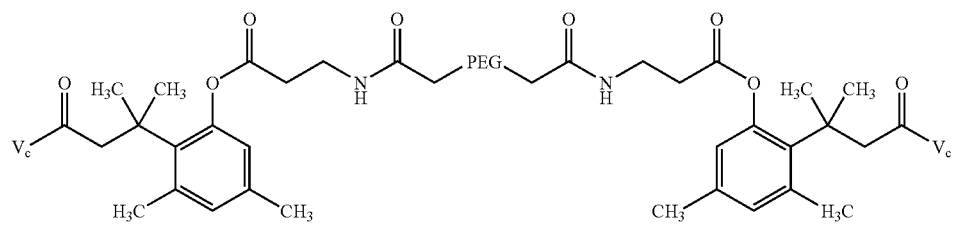

and

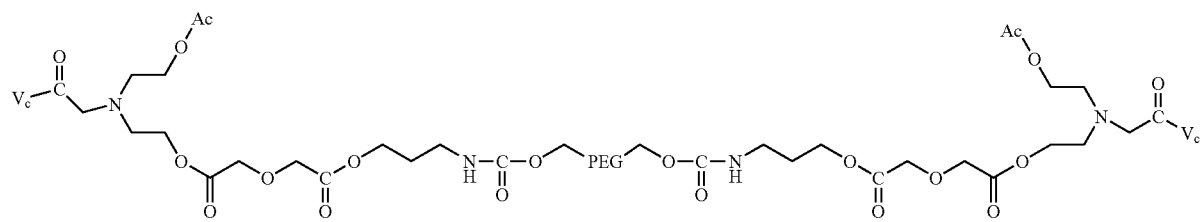

wherein

PEG is —O(—CH$_2$CH$_2$O)$_x$—;

x is a positive integer selected from about 10 to about 2300, and Vc is as described above.

In a still further aspect of the invention, there is provided an alternative method for attaching polymer residues to both the sugar and N-methyl amino groups of vancomycin compounds at the same time. This method includes reacting a vancomycin compound of formula (I) as shown above with at least about 2 equivalents of a polymer residue containing one leaving group (i.e. an mPEG or other mono-capped activated polymer linker) capable of reacting with the sugar amino group and/or the N-methyl amino group of the vancomycin compound in the presence of at least about a 5 to 20 fold molar excess amount of dimethylaminopyridine (DMAP) and a sufficient amount of a solvent mixture comprising dichloromethane (DCM) and dimethyl formamide (DMF). A 10 fold molar excess amount of DMAP is preferred.

This alternative method provides the artisan with a more direct path to providing vancomycin-compounds containing identical polymer residues attached to both the V$_3$ and X$_1$ amino groups as shown in the formula below:

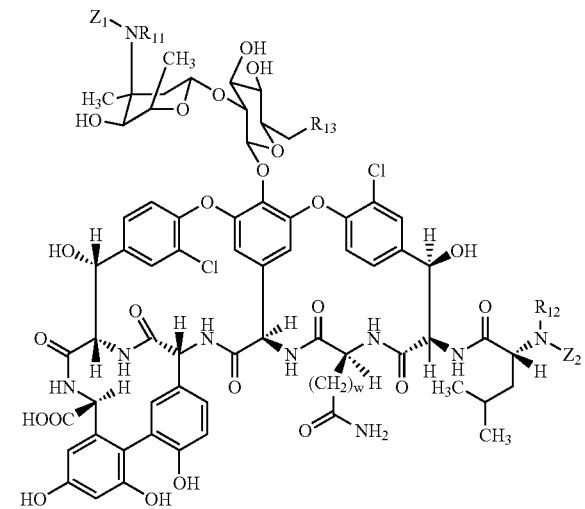

wherein:

R$_{11}$ and R$_{12}$ are independently selected from among hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxyalkyl, phenoxyalkyl and C$_{1-6}$ heteroalkoxys;

R$_{13}$ is OH, NH-aryl, NH-aralkyl, or NH—C$_{1-12}$ alkyl;

w is 1 or 2;

Z$_1$ and Z$_2$ are

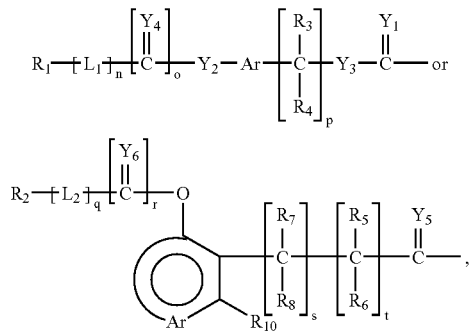

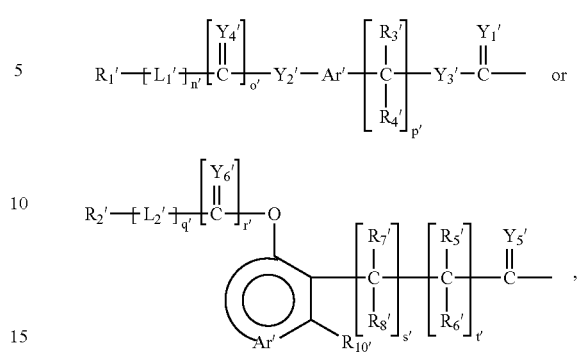

wherein

R$_1$ and R$_2$ are independently selected polymeric residues;

Y$_{1-6}$ are independently selected from the group consisting of O, S or NR$_9$;

R$_{3-10}$ are the same or different and are each independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxys;

Ar is a moiety which forms a multi-substituted aromatic hydrocarbon or a multi-substituted heterocyclic group;

L$_1$ and L$_2$ are independently selected bifunctional linkers;

p and t are independently selected positive integers;

n, q and s are independently either zero or a positive integer; and o and r are independently zero or one.

In a still further embodiment of the invention there are provided vancomycin polymer conjugates of the formula:

(II)

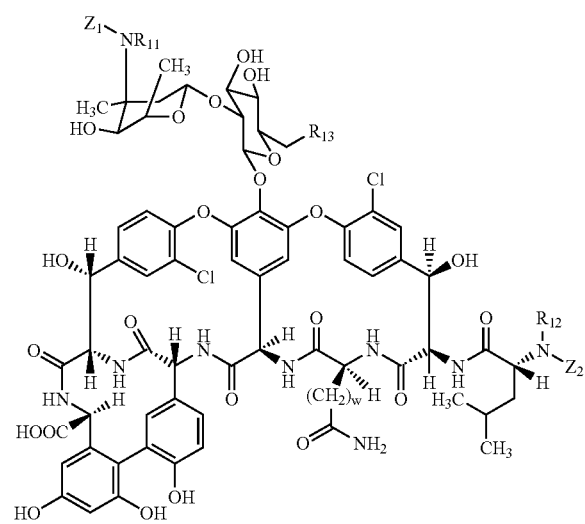

wherein:

Z$_1$, R$_{11}$, R$_{12}$, R$_{13}$ and w are the same as that previously defined and Z$_3$ is wherein R$_1$' and R$_2$' are independently selected polymeric residues;

Y$_{1-6}$' are independently selected from the group consisting of O, S or NR$_9$';

R$_{3-10}$' are the same or different and are each independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxys;

Ar' is a moiety which forms a multi-substituted aromatic hydrocarbon or a multi-substituted heterocyclic group;

L$_1$' and L$_2$' are independently selected bifunctional linkers;

p' and t' are independently selected positive integers;

n', q' and s' are independently either zero or a positive integer; and o' and r' are independently zero or one.

The preferred vancomycin compound for this aspect of the invention is:

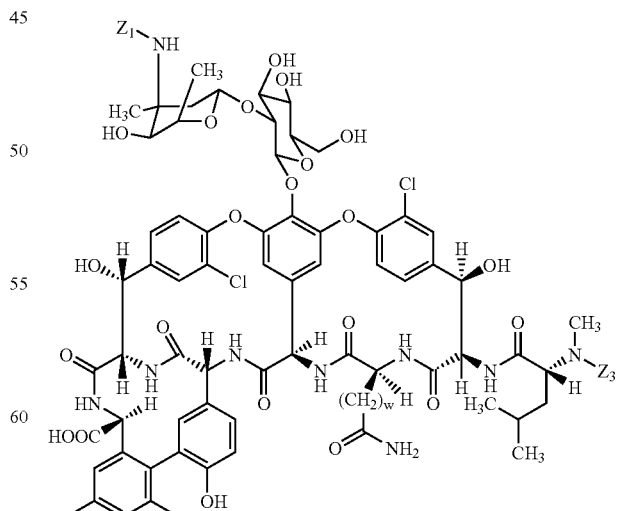

while Z$_1$ is preferably

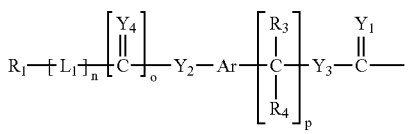

and $Z_3$ is preferably

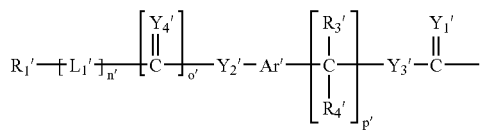

Some specific vancomycin-polymer conjugates corresponding to the above include those $V_3$—$X_1$-substituted vancomycin conjugates shown above in paragraph [0041].

In still further aspects of the invention, there are provided vancomycin-polymer conjugates in which the polymer residue is found substantially exclusively on the $X_1$ amino group and methods of preparing the same. Such conjugates are of she formula:

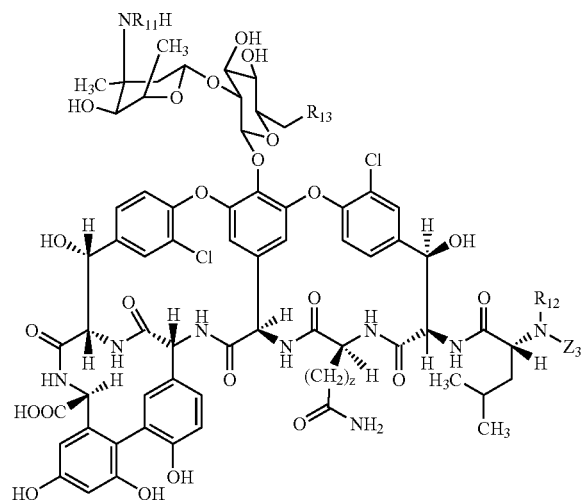

wherein all variables are as previously defined.

$R_1$, $R_1'$, $R_2$ and $R_2'$ are water soluble polymer residues which are preferably substantially non-antigenic. Preferably, they are polyalkylene oxides (PAO's) or polyethylene glycols (PEG's) or residues corresponding thereto. In some preferred aspects of the invention, $R_1$, $R_1'$, $R_2$ and $R_2'$ further include a capping group designated herein as A which allows the non-activated end to be capped or unavailable for further reaction. A non-limiting list of suitable PEG's include:

A-O—$(CH_2CH_2O)_x$—;

A-O—$(CH_2CH_2O)_x$—$CH_2C(O)$—O—;

A-O—$(CH_2CH_2O)_x$—$CH_2CH_2NR_{15}$—,

A-O—$(CH_2CH_2O)_x$—$CH_2CH_2S$—,

O—$(CH_2CH_2O)_x$—

—O—C(O)$CH_2$—O—$(CH_2CH_2O)_x$—$CH_2C(O)$—O—,

—$NR_{15}CH_2CH_2$—O—$(CH_2CH_2O)_x$—$CH_2CH_2NR_{15}$— and

—$SCH_2CH_2$—O—$(CH_2CH_2O)_x$—$CH_2CH_2S$—, wherein x is a positive integer representing the degree of polymerization and ranges from about 10 to about 2,300;

$R_{15}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxys, phenoxys and $C_{1-6}$ heteroalkoxys; and A is a capping group such as a $C_{1-6}$ alkyl, preferably methyl, or other PEG terminal activating groups, as such groups are understood by those of ordinary skill.

For the purpose of the present invention the structure:

—O—$(CH_2CH_2O)_x$— wherein x is a positive integer, is referred to as PEG throughout the application.

Also useful are polypropylene glycols, branched PEG derivatives such as those described above, see paragraph [0033], "star-PEG's" and multi-armed PEG's such as those described in Shearwater Corporation's 2001 catalog "Polyethylene Glycol and Derivatives for Biomedical Application". The disclosure of each of the foregoing is incorporated herein by reference. It will be understood that the water-soluble polymer can be functionalized for attachment to the bifunctional linkage groups if required without undue experimentation.

Although PAO's and PEG's can vary in average molecular weight, the polymer portion of the prodrug is broadly from about 2,000 Da to about 100,000 Da. In other aspects, the polymer has an average molecular weight of from about 5,000 Da to about 100,000 Da and is preferably from about 5,000 Da to about 40,000 Da. The average molecular weight of the polymer selected for inclusion in the prodrug must be sufficient so as to provide sufficient circulation of the prodrug before hydrolysis of the linker.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO's, the polymers are optionally selected from among one or more effectively non-antigenic materials such as dextran, polyvinyl alcohols, carbohydrate-based polymers, hydroxypropylmethylacrylamide (HPMA), polyglutamic acid, polyaspartic acid, polyhydroxyethyl aspartate (HEA), chitans and other like multifunctional non-antigenics as well as polyalkylene oxides, and/or copolymers thereof. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated. For-purposes of the present invention, "effectively non-antigenic" and "substantially non-antigenic" shall be understood to include all polymeric materials understood in the art as being substantially non-toxic and not eliciting an appreciable immune response in mammals regardless of the number of sites available for loading.

The leaving group moiety identified herein as $B_1$ and $B_2$ can be selected without limitation, from groups such as N-hydroxysuccinimidyl N-hydroxybenzotriazolyl, halogen, N-hydroxyphthalimidyl, p-nitrophenoxy, imidazolyl, thiazolidinyl thione, O-acyl ureas, pentafluorophenol or 2,4,6-trichlorophenol. Other suitable leaving groups will be apparent to those of ordinary skill.

For purposes of the present invention, leaving groups are to be understood as those groups which are capable of reacting with an amino group (nucleophile) found on the vancomycin compound.

Preferably the substituents are reacted in an inert solvent such as dimethylformamide (DMF), methylene chloride (DCM), tetrahydrofuran (THF), acetonitrile ($CH_3CN$), chloroform ($CHCl_3$), or mixtures thereof. The reaction is preferably conducted at a temperature from 0° C. up to about 22° C. (rm temperature).

Methods of Treatment

Another aspect of the present invention provides methods of treatment for various medical conditions in mammals. The methods include administering to the mammal in need of such treatment, an effective amount of the prodrug, i.e. vancomycin, which has been prepared as described herein. The compositions are useful for, among other things, treating vancomycin-sensitive infections.

The amount of the prodrug administered will depend upon the vancomycin compound selected. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis molecular weight of the polymer, etc. In general, however, it is contemplated that the vancomycin prodrugs will be administered in amounts ranging from about 0.5 to about 60 mg/kg twice a week. Preferably, the vancomycin is administered in amounts ranging from about 0.5 to about 30 mg/kg per day. The ranges set forth above are based on the amount of vancomycin derivative. The ranges are also illustrative and those skilled in the art will determine the optimal dosing of the prodrug selected based on clinical experience and the treatment indication. Actual dosages will be apparent to the artisan without undue experimentation.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof.

Another aspect of the invention is a method of treating vancomycin susceptible diseases in mammals using a combination of a vancomycin in unmodified or commonly available forms, e.g. vancomycin HCl, or other pharmaceutically acceptable salt, solvate or hydrate thereof, and a polymeric conjugate of the invention. The total amount of vancomycin administered to the patient in need thereof is an effective amount as mentioned above, based on the amount of vancomycin. The combination of prodrug and vancomycin derivative can be administered to a patient in need of the drug or such treatment as part of a single pharmaceutical dosage form (e.g. intravenous or parenteral injection/infusion or oral dosage form) or as part of a treatment regimen in which both of the vancomycin and vancomycin prodrug are administered as separate dosage forms to a patient in need thereof. Thus, the vancomycin and polymeric conjugate of the invention are administered either substantially concurrently in separate dosage forms or combined in a unit dosage form.

Since the present invention can relate to treatment with a combination of vancomycin dosage forms which can be administered separately, the invention also relates to combining separate pharmaceutical compositions in kit form. That is, a kit is contemplated wherein two separate unit dosage forms are combined: for example a vancomycin pharmaceutical composition and a separate pharmaceutical composition containing a polymer conjugate of the invention. The kit will preferably include directions for the administration of the separate components. The kit form is particularly advantageous when the separate components must be administered in different dosage forms and/or are administered at different dosage intervals. Thus a kit may comprise, in separate containers in a single package, pharmaceutical compositions for use in a therapeutically effective amount of vancomycin or a pharmaceutically acceptable salt, solvate or hydrate thereof in a pharmaceutically acceptable carrier and in a second container a therapeutically effective amount of a polymer conjugate as described herein in the form of a pharmaceutically acceptable salt, solvate or hydrate thereof in a pharmaceutically acceptable carrier.

Biological Data

1. $LD_{90-100}$ Examination of PEG-Vancomycin Conjugates 3, 13, 22, 30, 38, and 39, the synthesis of which is described below in ICR Swiss Mice Studies examining the in vivo anti-infective potential of PEG-vancomycin conjugates in ICR Swiss mice were performed. In the initial study, PEG-vancomycin conjugates 3, 13, 22, 30, 38, and 39 were administered at 100 mg/kg vancomycin equivalents in two equal split doses given 1 and 2.5 hours following a $LD_{90-100}$ inoculation of *Staphylococcus aureus* (Smith) to ICR Swiss mice. As controls, *S. aureus* (Smith) challenged mice were administered either saline or 100 mg/kg vancomycingiven in equal split doses. Ten mice were used per compound tested. Mice were observed for 1 week for survival. Significant anti-microbial activity was indicated by greater than 50% survival of the mice. This study showed all mice treated with PEG-vancomycin conjugates had significantly enhanced survival (80%-100%), as compared to 100% survival in mice treated with native vancomycin (@ 100 mg/kg).

A second study was also performed to examine the sustained anti-infective protection of PEG-vancomycin conjugate 22. ICR Swiss mice were administered with either 100 mg/kg vancomycin equivalents of 22, 100 mg/kg vancomycin, or saline in two equally split doses 1½ hours apart. Ten mice per treatment group were used. Mice were challenged with an $LD_{90-100}$ inoculum of S. aureus (Smith) 25.5 hours after initial administration of test compounds. Mice were observed for survival as before.

2. Pharmacokinetics of Vancomycin (1) and PEG-vancomycin Conjugates 13, 22, 30, 38, and 39 in Rats This study was performed to determine the circulatory pharmacokinetics of PEG-vancomycin conjugates (dimers) (13, 22, 30, 38, and 39) in rats. PEG-vancomycin conjugates containing a 50 mg/kg vancomycin equivalent dose and 50 mg/kg native vancomycin (1) were injected as a single intravenous dose into the tail vein of conscious rats at a rate of 0.5 ml/min [~2.5 min]. Blood samples were obtained 72 h prior to treatment and at 0.08 h, 0.5 h, 1 h, 2 h, 4 h, 8 h, 24 h, 48 h, 72 h, and 96 h. A 250 µL bled was done on rats sedated with 30% $O_2$/70% $CO_2$ via the retro-orbital plexus into EDTA containing vials. Blood was immediately processed for plasma and frozen on dry ice. Plasma samples were stored at −80° C. until analyzed. The plasma samples were analyzed by a fluorescence polarization immunoassay using an Abbott Laboratories $TD_x$ analyzer within two hours of thawing. A single compartment model using WinNonlin™ software was used to determine the-plasma pharmacokinetic parameters. The plasma concentration-time curves showed coefficients of determination ($r^2$) of greater than 0.96 for all PEG-vancomycin conjugates and 1.00 for vancomycin itself.

Biological Data

1. $LD_{90-100}$ Examination of PEG-Vancomycin Conjugates 3, 13, 22, 30, 38, and 39 in ICR Swiss Mice These studies indicate that PEG-vancomycin conjugates 3, 13, 22, 30, 38, and 39 when administered at 100 mg/kg vancomycin equivalents showed significant activity against S. aureus challenged mice. Likewise, the PEG-vancomycin conjugate 22 showed sustained 24 hour anti-microbial protection against S. aureus challenge in ICR Swiss mice.

Compound 22 showed significant anti-microbial activity with 80% survival of the mice. Native vancomycin treatment and saline control showed no protection with 0% survival. All the data are summarized in Tables 1 and 2.

TABLE 1

Compound Description and Summary of $LD_{90-100}$ Results

| Compound | % Active* | Saline Stability (24 h) 25° C. | $t_{1/2}$ in Rat Plasma Stability (h) 37° C. | Post¶ Challenge % Survival (mice) | Pre-‡ Challenge % Survival (mice) |
|---|---|---|---|---|---|
| Saline | — | — | — | 10 | 0 |
| 1 | — | — | — | 100 | 0 |
| 3 | 6.6 | 3.1% | 2 | 100 | — |
| 22 | 6.1 | 1.4% | 16 | 100 | 80 |
| 30 | 5.15 | <1% | >24 | 90 | — |
| 13 | 6.56 | 1.4% | 18.8 | 100 | — |

TABLE 1-continued

Compound Description and Summary of $LD_{90-100}$ Results

| Compound | % Active* | Saline Stability (24 h) 25° C. | $t_{1/2}$ in Rat Plasma Stability (h) 37° C. | Post¶ Challenge % Survival (mice) | Pre-‡ Challenge % Survival (mice) |
|---|---|---|---|---|---|
| 38 | 8.8 | ~2% | 4.6 | 100 | — |
| 39 | 5.39 | ~2% | ~5 | 80 | — |

*Vancomycin (Van) by weight

¶Compound given 1 h following S. aureus (Smith) challenge, survival after 1 week ‡Compound given 8 h prior to S. aureus (Smith) challenge, survival after 1 week

TABLE 2

Minimum Inhibitory Concentration (MIC) of PEG-Conjugates

| | MIC (µg/mL)* | | | |
|---|---|---|---|---|
| Compound | E.coli (25922) | E. faecalis (29212) | S. aureus (29214) | S. aureus (6538P) |
| 1 | >100 | 6.2 | 3.1 | 1.6 |
| 3 | >100 | 50 | 25 | 25 |
| 22 | >100 | — | 10.9 | 10.9 |
| 13 | >100 | >50 | >50 | >100 |
| 38 | >100 | >50 | >50 | >100 |
| 39 | >100 | >50 | >50 | >100 |

*vancomycin equivalents

2. Pharmacokinetics of Vancomycin (1) and PEG-vancomycin Conjugates 13, 22, 30, 38, and 39 in Rats In this study, vancomycin showed a circulatory half-life ($t_{1/2}$) of 0.34 h with a Cmax of 162 µg/mL and an area under the curve (AUC) of 78.8 h µg/mL. Vancomycin had a clearance. (CL) of 642 mL/h/kg and a volume of distribution at a steady state (Vss) of 309 mL/kg in rats.

Overall the pharmacokinetic estimates of the PEG-vancomycin conjugates uniformly showed a longer sustained, although lower concentration, of circulating free vancomycin in rat plasma. All of the PEG-vancomycin conjugates showed a 12 to 64 fold longer $t_{1/2}$ [4.08 h-21.9 h]. Not unexpectedly, because of the anticipated sustained release of the conjugated vancomycin preparations, all of the conjugates achieved Cmax values that were 16% to 33% [26 µg/mL-54 µg/mL] of those observed for unmodified vancomycin. The AUC for the PEG-vancomycin conjugates were 1.4 to 9.1 fold greater [112 h µg/mL-717 h µg/mL] than that observed for vancomycin and had concomitantly slower clearance rates [71 mL/h/kg-178 mL/kg] that were 11% to 28% of vancomycin's. The Vss of the PEG-vancomycin conjugates were 3-9 fold greater [938 mL/kg-2723 mL/kg] than that observed for vancomycin. The PK profile is summarized in the following Table 3.

TABLE 3

Pharmacokinetics of intravenous bolus administration of 50 mg/kg vancomycin equivalents of PEG-vancomycin conjugates in rats

| Compound | Cmax (ug/mL) | Plasma Half-life (hr) | CL (mL/hr/kg) | Vss (mL/kg) | AUC (hr * ug/mL) |
|---|---|---|---|---|---|
| 1  | 162.0 ± 9.0 | 0.34 ± 0.04  | 642.0 ± 83.7 | 309.3 ± 17.2   | 78.8 ± 10.8 |
| 22 | 47.9 ± 4.3  | 4.09 ± 0.25  | 178.3 ± 13.4 | 2640.8 ± 23.9  | 282.2 ± 28.5 |
| 30 | 54.6 ± 2.5  | 9.12 ± 0.98  | 70.0 ± 5.4   | 1648.3 ± 81.5  | 716.9 ± 56.8 |
| 13 | 25.5 ± 2.1  | 10.48 ± 0.58 | 131.1 ± 18.2 | 2723.3 ± 97.3  | 386.4 ± 51.4 |
| 38 | 53.7 ± 5.4  | 2.23 ± 0.38  | 293.9 ± 26.1 | 938.0 ± 94.3   | 171.0 ± 15.2 |
| 39 | 24.8 ± 7.7  | 21.19 ± 6.90 | 70.9 ± 6.3   | 2128.6 ± 560.1 | 708.4 ± 61.0 |

EXAMPLES

Figure 1B:
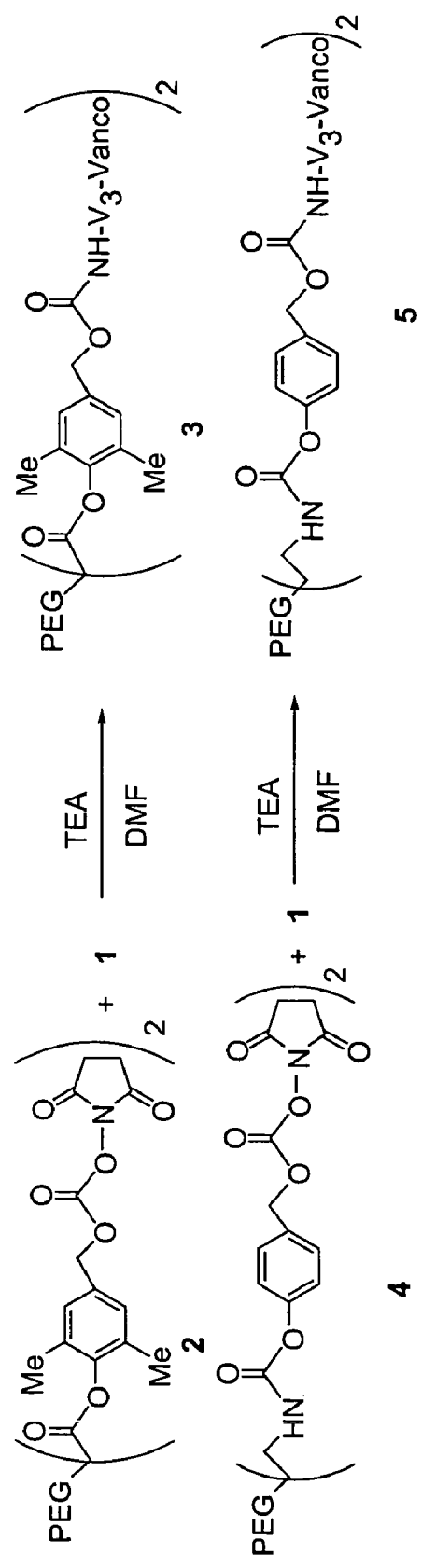
Figure 2:
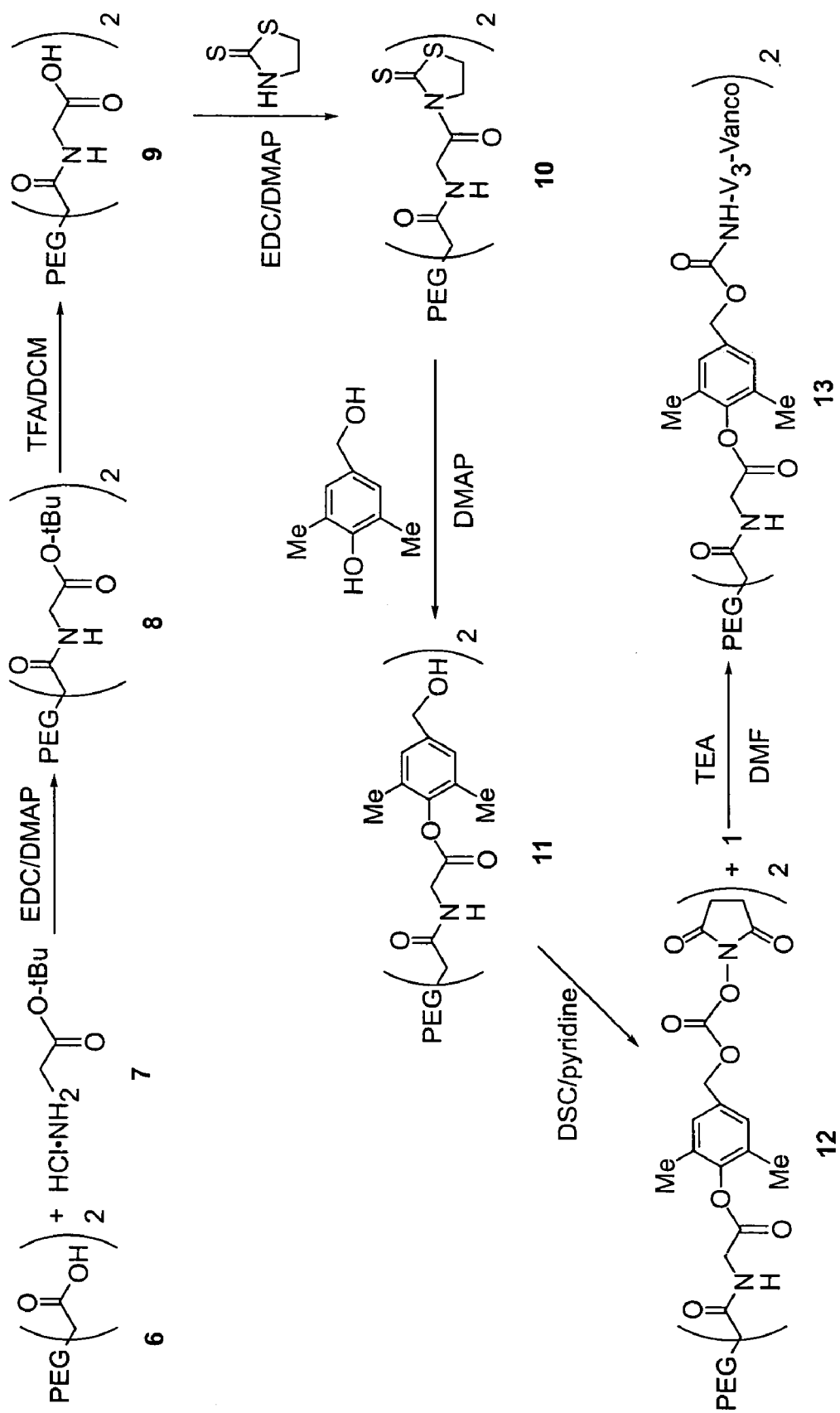
Figure 3:
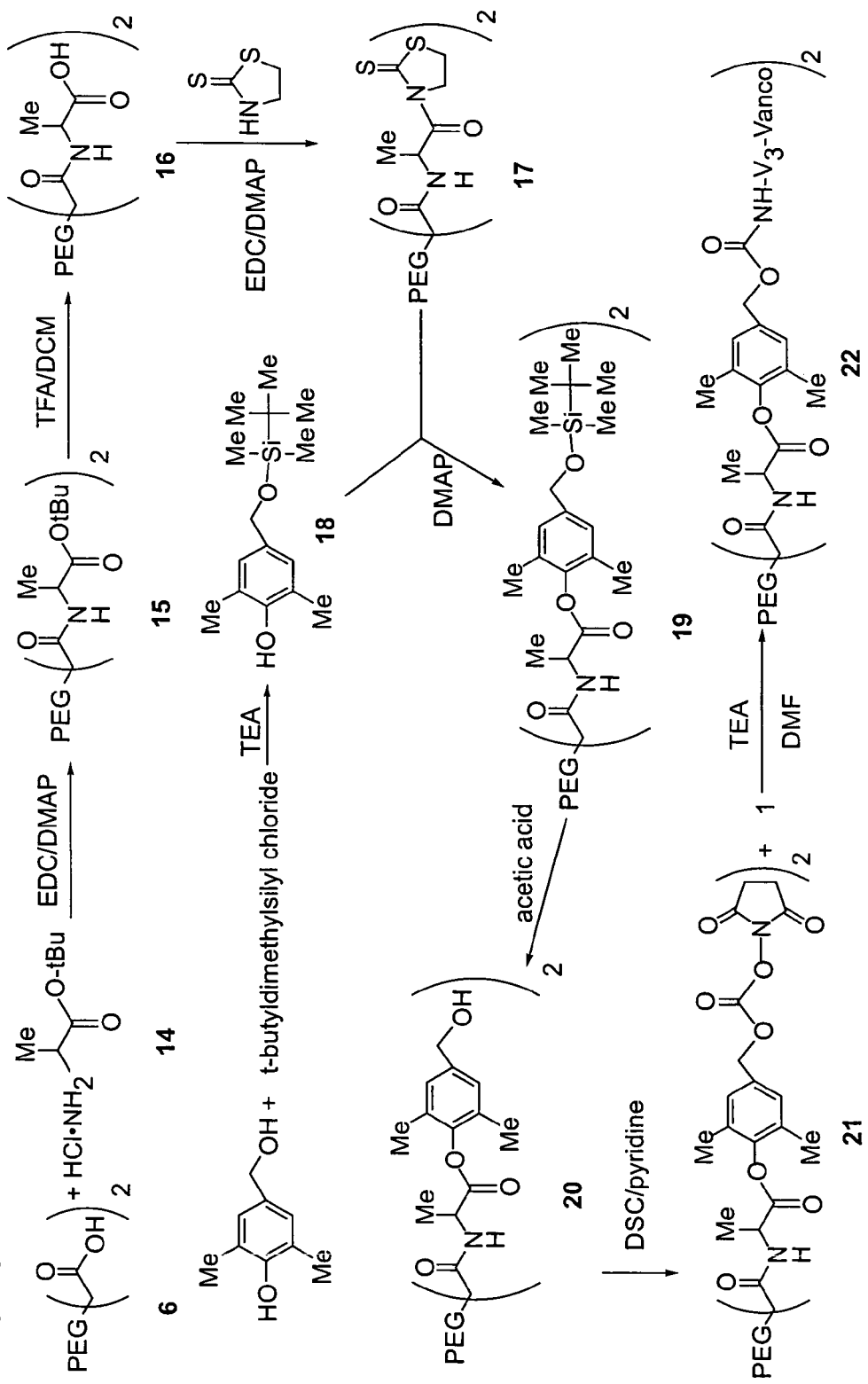
Figure 4:
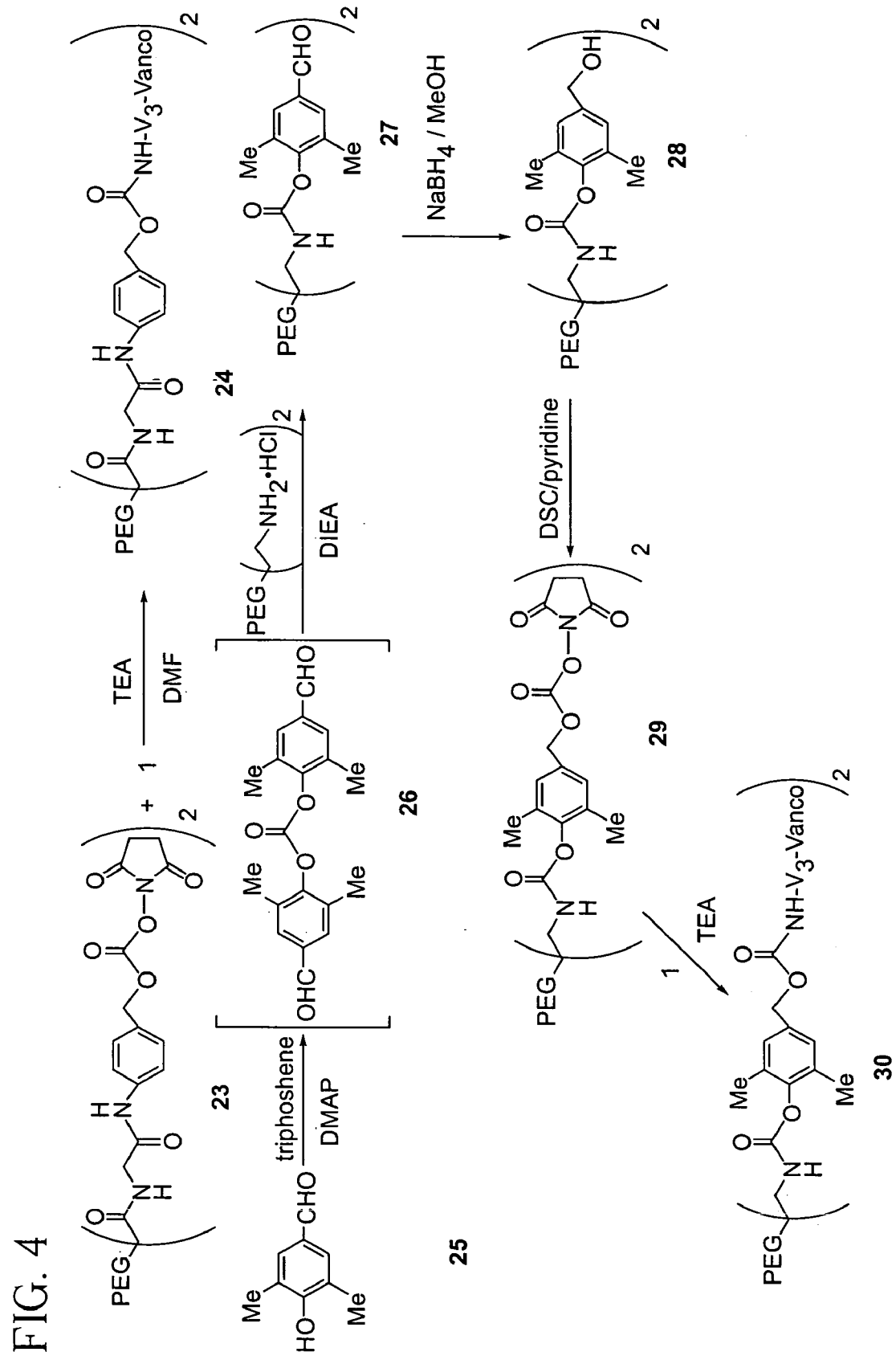
Figure 5:
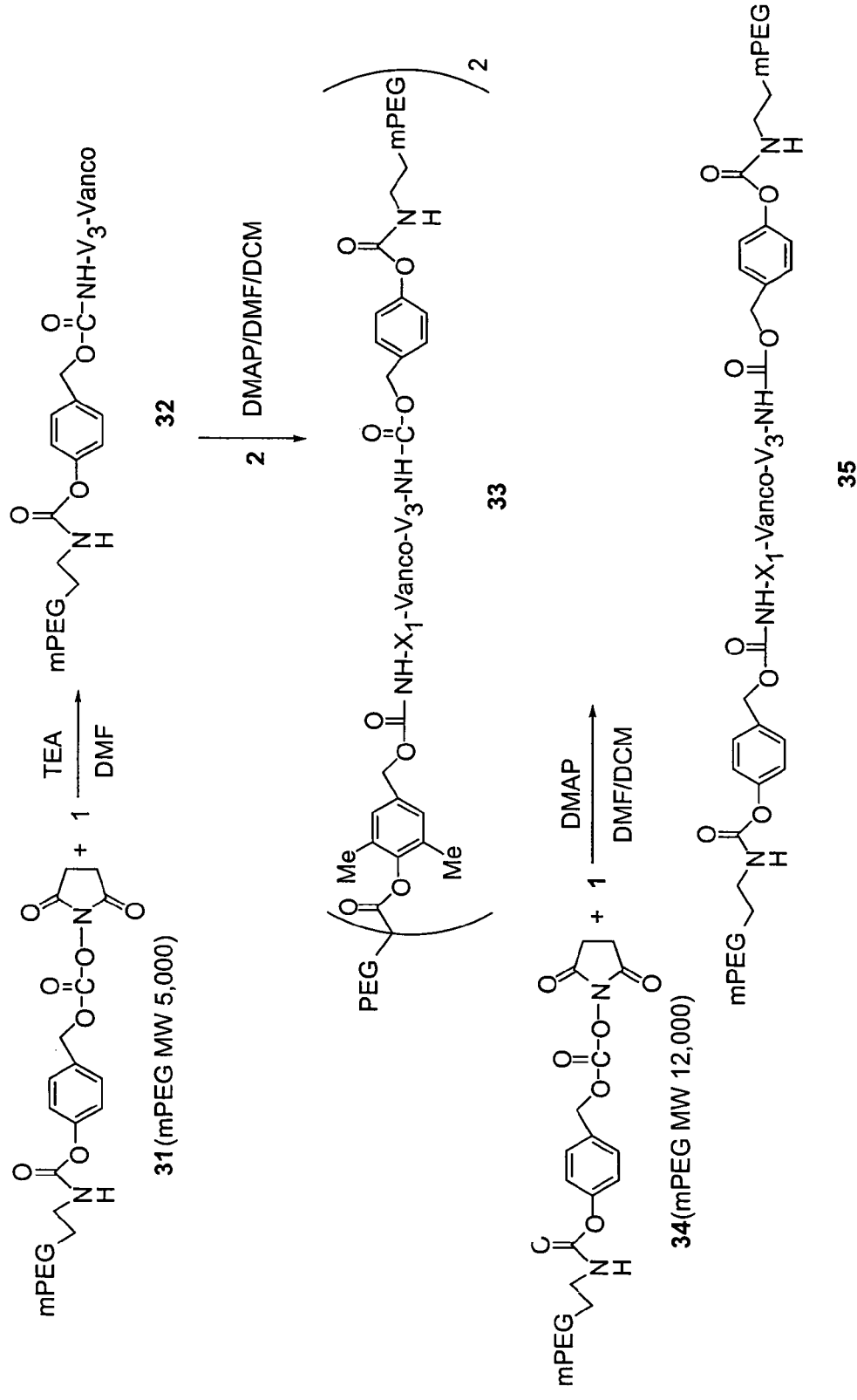
Figure 6A:
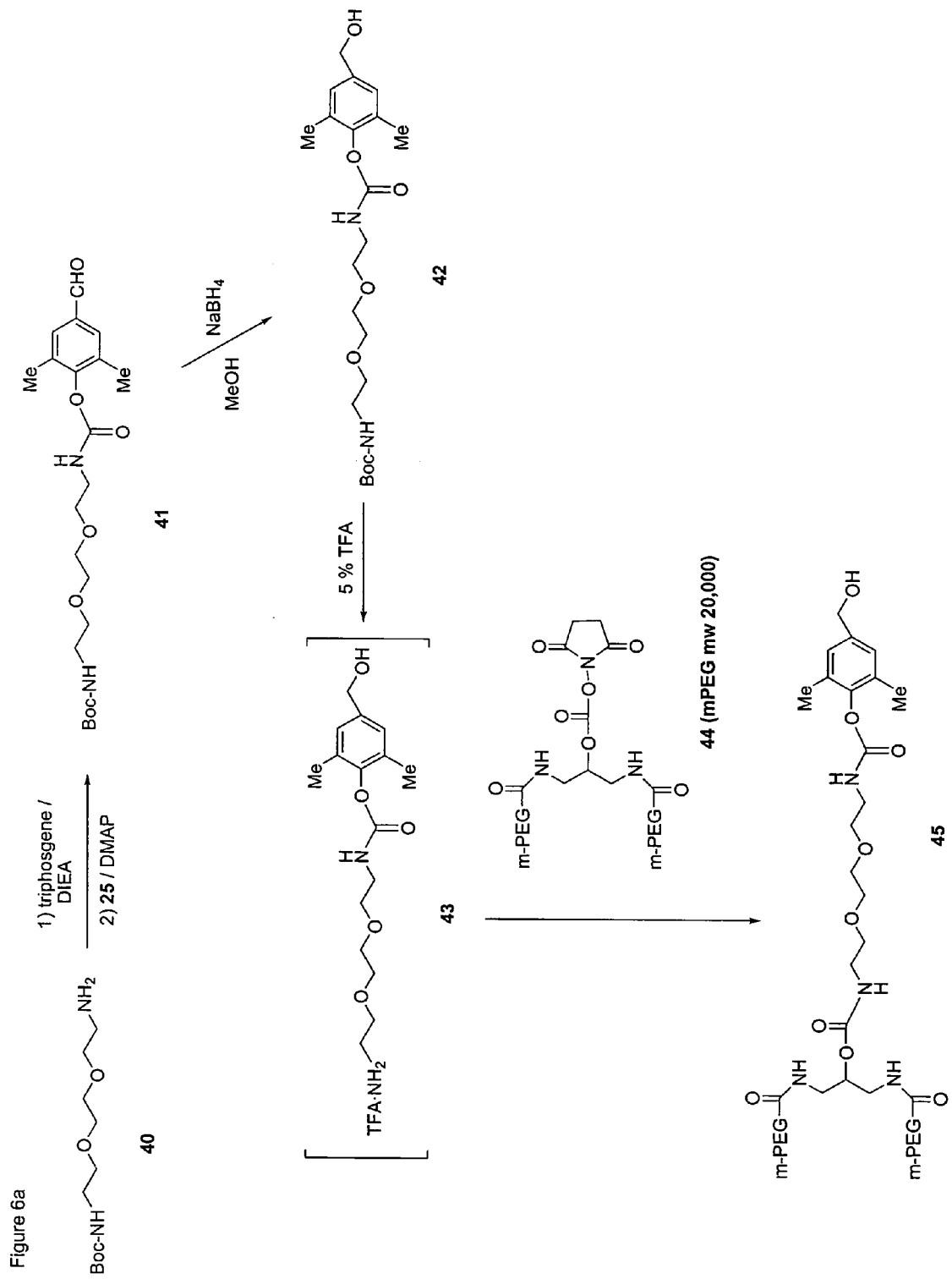
Figure 6B:
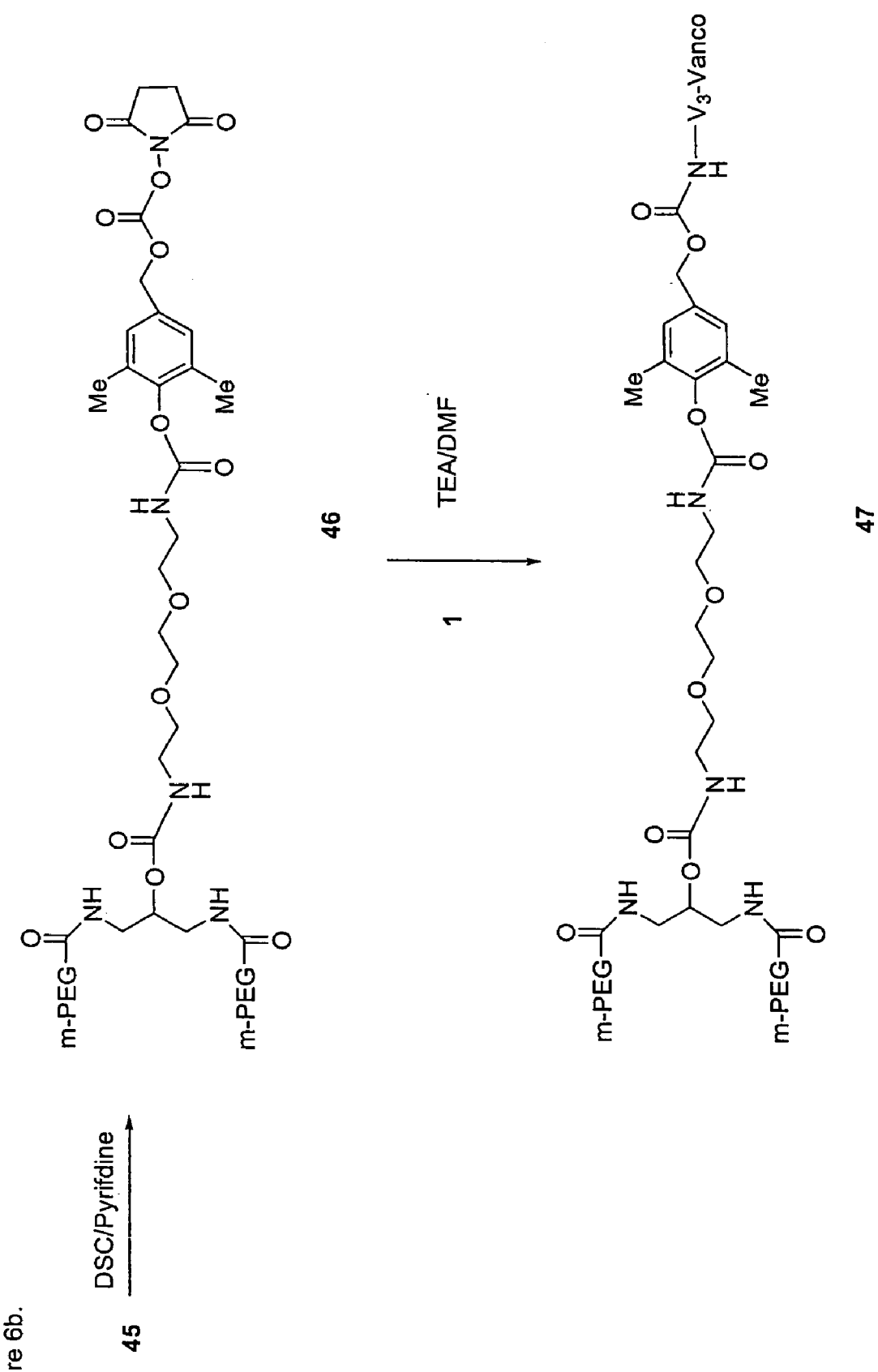
Figure 7:
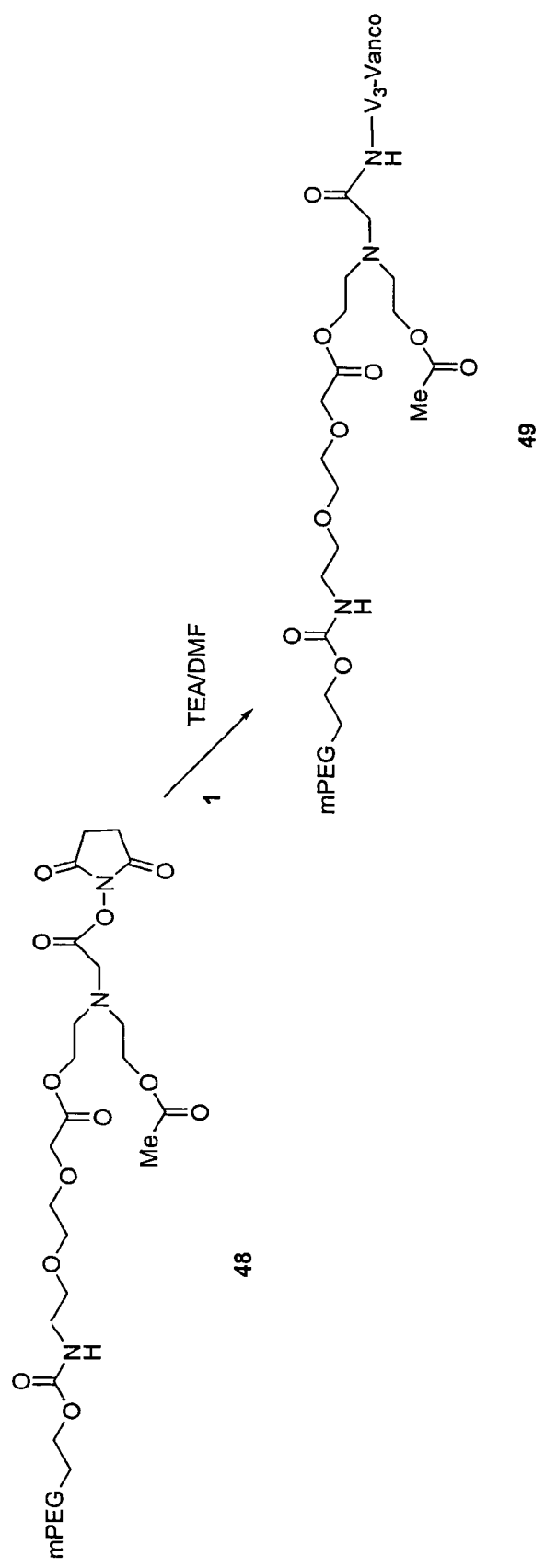

The following examples serve to provide further appreciation of the invention but are not meant in any way to restrict the effective scope of the invention. The underlined and bold-faced numbers recited in the Examples correspond to those shown in the FIGS. 1-7.

General Procedures. All reactions were run under an atmosphere of dry nitrogen or argon. Commercial reagents were used without further purification. All PEG compounds were dried under vacuum or by azeotropic distillation from toluene prior to use. Polyethylene glycol (PEG) linkers: compounds 2, 4, 23, 31, 34, and 36 are made according to the procedures described in US patent "Polymeric prodrugs of amino- and hydroxyl-containing bioactive agents" (U.S. Pat. No. 6,180,095) and the paper "Drug delivery systems employing 1,4- or 1,6-elimination: releasable poly(ethylene glycol) conjugates of amine-containing compounds" (J. Med. Chem., 1999, Vol. 42, No. 18, pages 3657-3667), the contents of which are disclosed herein by reference. $^{13}$C NMR spectra were obtained at 75.46 MHz using a Varian Mercury®300 NMR spectrometer and deuterated chloroform and pyridine as the solvents unless otherwise specified. Chemical shifts (δ) are reported in parts per million (ppm) downfield from tetramethylsilane (TMS). All vancomycin-polymer conjugation reactions were carried out in the presence of 4 Angstrom molecular sieves.

HPLC method. The reaction mixtures and the purity of intermediates and final products were monitored by a Beckman Coulter System Gold® HPLC instrument. It employs a ZOBAX® 300SB C8 reversed phase column (150×4.6 mm) or a Phenomenex Jupiter® 300A C18 reversed phase column (150×4.6 mm) with a multiwavelength UV detector, using a gradient of 10-90% of acetonitrile in 0.05% trifluoroacetic acid (TFA) at a flow rate of 1 mL/min.

Example 1

Compound 3. To a solution of compound 1 (0.535 g, 0.369 mmol) and triethylamine (TEA, 1.026 mL, 7.36 mmol) in anhydrous dimethylformamide (DMF, 150 mL) was added PEG linker 2 MW 40,000 daltons, prepared as described in the aforementioned U.S. Pat. No. 6,180,095, (7.5 g, 0.184 mmol) and the resulting mixture stirred at room temperature for 12 hrs. The solution was filtered through celite, and treated with ethyl ether (300 mL). Filtration gave crude product which was recrystallized from a mixture of DMF/TEA/isopropanol (IPA) (45 mL/1 mL/180 mL) twice to give 3 (7.61 g, 0.175 mmol, 95%). $^{13}$C NMR (67.8 MHz, $C_5D_5N$) δ 174.44, 172.32, 170.65, 169.15, 168.74, 167.02, 159.02, 157.39, 155.37, 142.98, 142.09, 133.22, 130.37, 128.45, 127.32, 119.79, 118.28, 107.79, 102.76, 98.54, 90.25, 88.38, 78.93, 77.34, 76.41, 64.41, 62.58, 61.65, 60.71, 58.87, 56.97, 54.39, 53.35, 35.64, 25.29, 24.23, 23.48, 22.32, 18.46, 16.35, 12.08.

Example 2

Compound 5. Prepared in 88% yield by reacting 1 with 4 as described above in Example 1 to yield 3, except that 2 is replaced by 4. The structure is confirmed by $^{13}$C NMR.

Example 3

Compound 8. To a solution of 40 kDa PEG di-acid (6, 22.0 g, 0.548 mmol), glycine t-butyl ester hydrochloride (1.10 g, 6.58 mmol), and 4-dimethylaminopyridine (DMAP, 1.60 g, 13.16 mmol) in anhydrous methylene chloride (DCM, 200 mL) cooled to 0° C. in an ice bath was added 1-(3-dimethylaminopropyl)-3-ethylcarbodiimide hydrochloride (EDC, 1.26 g, 6.58 mmol). This mixture was allowed to warm to room temperature and stirred for 12 hrs, followed by partial removal of the solvent under reduced pressure. The PEG derivative was precipitated with addition of ethyl ether, filtered, and crystallized from 2-propanol (IPA, 440 mL) to yield 8 (20.8 g, 0.515 mmol, 94%). $^{13}$C NMR (67.8 MHz, $CDCl_3$) δ 169.92, 168.38, 70.36-69.78 (PEG), 40.85, 27.68.

Example 4

Compound 9. A solution of 8 (20.0 g, 0.496 mmol) in DCM (200 mL) and trifluoroacetic acid (TFA, 100 mL) was stirred at room temperature for 2 hours, followed by partial removal of the solvent under reduced pressure. The PEG derivative was precipitated by the addition of ethyl ether, filtered, and washed with ethyl ether to yield 9 (18.2 g, 0.451 mmol, 91%). $^{13}$C NMR (67.8 MHz, $CDCl_3$) δ 170.07, 170.00, 72.91-67.29 (PEG), 39.99.

Example 5

Compound 10. To a solution of 9 (17.0 g, 0.423 mmol), 2-mercapto-thiazoline (2-MT, 0.20 g, 1.69 mmol), and DMAP (0.21 g, 1.69 mmol) in anhydrous DCM (150 mL) cooled to 0° C. was added EDC (0.32 g, 1.69 mmol). The reaction mixture was allowed to warm to room temperature and stirred for 12 hrs, followed by partial removal of the solvent under reduced pressure. The PEG derivative was precipitated by the addition of ethyl ether, filtered, and crystallized from IPA (340 mL) to yield 10 (16.5 g, 0.410 mmol, 97%). $^{13}$C NMR (67.8 MHz, $CDCl_3$) δ 200.96, 170.22, 170.01, 72.13-69.72 (PEG), 55.35, 45.58, 28.67.

Example 6

Compound 11. A solution of 10 (16.0 g, 0.40 mmol), 3,5-dimethyl-4-hydroxybenzylalcohol (0.78 g, 5.14 mmol), and DMAP (0.63 g, 5.14 mmol) in anhydrous DCM (150 mL) was refluxed for 18 hrs, followed by partial removal of the solvent under reduced pressure. The PEG derivative was precipitated with addition of ethyl ether, filtered, and crystallized from IPA to yield 11 (14.6 g, 0.36 mmol, 90%). $^{13}$C NMR (67.8 MHz, CDCl$_3$) δ 170.53, 167.47, 146.49, 138.80, 129.52, 126.61, 72.14-69.54 (PEG), 63.68, 39.96, 15.89.

Example 7

Compound 12. To a solution of 11 (3.8 g, 0.094 mmol) and disuccinimidyl carbonate (DSC, 0.19 g, 0.75 mmol) in anhydrous DCM (40 mL) and DMF (4 mL) cooled to 0° C. was added pyridine (0.059 g, 0.75 mmol). The reaction mixture was allowed to warm to room temperature and stirred for 12 hrs, followed by partial removal of the solvent under reduced pressure. The PEG linker was precipitated by the addition of ethyl ether, filtered, and crystallized from DCM/ethyl ether to yield 12 (3.3 g, 0.082 mmol, 87%). $^{13}$C NMR (67.8 MHz, CDCl$_3$) δ 170.52, 168.15, 167.24, 151.06, 148.02, 130.55, 130.42, 128.47, 71.83-69.64 (PEG), 40.12, 25.18, 16.05.

Example 8

Compound 13. Prepared in 88% yield by reacting 1 with 12 as described in Example 1 to yield 3, except that 2 is replaced by 12. $^{13}$C NMR (67.8 MHz, C$_5$D$_5$N) δ 174.68, 171.17, 168.62, 167.14, 159.00, 157.50, 155.50, 142.00, 133.50, 130.51, 128.38, 127.24, 78.93, 65.22, 63.76, 62.49, 54.39, 52.20, 44.61, 43.29, 35.52, 25.23, 24.20, 23.46, 22.30, 18.47, 16.37.

Example 9

Compound 15. To a solution of 6 (25.0 g, 0.623 mmol), alanine t-butyl ester hydrochloride 14 (1.36 g, 7.48 mmol), and DMAP (1.82 g, 14.95 mmol) in anhydrous DCM (300 mL) cooled to 0° C. in an ice bath was added EDC (1.44 g, 7.48 mmol). This mixture was allowed to warm to room temperature and stirred for 12 hrs, followed by partial removal of the solvent under reduced pressure. The PEG derivative was precipitated by the addition of ethyl ether, filtered, and crystallized from IPA (500 mL) to yield 15 (20.8 g, 0.515 mmol, 94%). $^{13}$C NMR (67.8 MHz, CDCl$_3$) δ 171.19, 168.78, 71.05-69.32 (PEG), 47.62, 27.64, 18.10.

Example 10

Compound 16. A solution of 15 (23.0 g, 0.570 mmol) in DCM (250 mL) and TFA (150 mL) was stirred at room temperature for 2 hours, followed by partial removal of the solvent under reduced pressure. The PEG derivative was precipitated by the addition of ethyl ether, filtered, and washed with ethyl ether to yield 16 (22.6 g, 0.559 mmol, 98%). $^{13}$C NMR (67.8 MHz, CDCl$_3$) δ 172.67, 168.98, 71.02-69.83 (PEG), 46.89, 17.93.

Example 11

Compound 17. To a solution of 16 (22.5 g, 0.558 mmol), 2-MT (0.266 g, 2.24 mmol), and DMAP (0.27 g, 2.24 mmol) in anhydrous DCM (250 mL) cooled to 0° C. was added EDC (0.43 g, 2.24 mmol). The reaction mixture was allowed to warm to room temperature and stirred for 12 hrs, followed by partial removal of the solvent under reduced pressure. The PEG derivative was precipitated with the addition of ethyl ether, filtered, and crystallized from IPA (450 mL) to yield 17 (21.3 g, 0.525 mmol, 94%). $^{13}$C NMR (67.8 MHz, CDCl$_3$) δ 200.41, 174.12, 168.92, 72.93-69.34 (PEG), 56.00, 48.03, 28.45, 17.85.

Example 12

Compound 18. To a solution of 3,5-dimethyl4-hydroxybenzylalcohol (8.00 g, 52.57 mmol) and t-butyldimethysilyl chloride (8.71 g, 57.8 mmol) in anhydrous DMF (40 mL) cooled to 0° C. for half an hour was added dropwise a solution of triethylamine (TEA, 21.27 g, 210.2 mmol) in anhydrous DMF (20 mL) over 30 minutes. The resulting solution was allowed to warm to room temperature and stirred overnight. The mixture was filtered and the filtrate evaporated under reduced pressure. The residue was suspended in water and extracted by DCM (3×150 mL). The organic layers were combined, washed with water (3×300 mL), dried (MgSO$_4$), filtered, and the solvent evaporated under reduced pressure to give 18 (12.0 g, 43.40 mmol, 82.6%). $^{13}$C NMR (67.8 MHz, CDCl$_3$) δ 151.31, 132.85, 126.87, 122.94, 64.87, 25.92, 18.38, 15.87, −5.32.

Example 13

Compound19. A solution of 17 (14.0 g, 0.346 mmol), 18 (1.20 g, 4.50 mmol), and DMAP (0.55 g, 4.50 mmol) in anhydrous DCM (150 mL) was refluxed for 18 hrs, followed by partial removal of the solvent under reduced pressure. The PEG derivative was precipitated by the addition of ethyl ether, filtered, and crystallized from IPA to yield 19 (12.6 g, 0.308 mmol, 89%). $^{13}$C NMR (67.8 MHz, CDCl$_3$) δ 170.08, 169.38, 146.05, 138.47, 129.22, 125.80, 72.916-8.83 (PEG), 64.06, 47.30, 25.68, 17.76, 16.10, −5.47.

Example 14

Compound 20. A solution of 19 (12.5 g, 0.31 mmol) in a mixture of glacial acetic acid (180 mL) and water (60 mL) was stirred for 2 hrs at room temperature, followed by extraction with DCM. The organic layer was dried (anhydrous sodium sulfate), filtered, and the solvent partially removed under reduced pressure. The PEG derivative was precipitated with addition of ethyl ether, filtered, and crystallized from DCM/ethyl ether to yield 20 (11.8 g, 0.29 mmol, 95%). $^{13}$C NMR (67.8 MHz, CDCl$_3$) δ 170.00, 169.38, 146.36, 138.71, 129.45, 126.62, 72.93-69.06 (PEG), 63.80, 47.30, 17.73, 16.04.

Example 15

Compound 21. To a solution of 20 (9.0 g, 0.222 mmol) and DSC (1.14 g, 4.44 mmol) in anhydrous DCM (90 mL) and DMF (9 mL) cooled to 0° C. was added pyridine (0.351 g, 4.44 mmol). The reaction mixture was allowed to warm to room temperature and stirred for 12 hrs, followed by partial removal of the solvent under reduced pressure. The PEG linker was precipitated with addition of ethyl ether, filtered, and crystallized from DCM/ethyl ether to yield 21 (6.5 g, 0.158 mmol, 71%). $^{13}$C NMR (67.8 MHz, CDCl$_3$) δ 170.05, 169.64, 168.20, 151.18, 148.07, 130.67, 130.51, 128.65, 71.98-69.93 (PEG), 47.48, 25.30, 17.82, 16.21.

Example 16

Compound 22. Prepared in 83% yield by reacting 1 with 21 as described in Example 1 for preparation of 3, except that 2 is replaced by 21. $^{13}$C NMR (67.8 MHz, $C_5D_5N$) δ 174.80, 171.46, 170.77, 144.20, 130.84, 128.75, 127.59, 119.00, 79.10, 78.38, 64.95, 62.92, 61.99, 54.69, 52.31, 51.38, 48.89, 35.85, 25.57, 24.52, 23.78, 22.65, 18.75, 16.79, 15.27.

Example 17

Compound 24. Prepared in 88% yield by reacting 1 with 23 as described in Example 1 for preparation of 3, except that 2 is replaced by 21. The structure of the product is confirmed by $^{13}$C NMR.

Example 18

Compound 27. To a solution of 3,5-dimethyl-4-hydroxybenzaldehyde 25 (0.73 g, 4.89 mmol) and triphosgene (0.21 g, 0.70 mmol) in 100 ml of dry DCM cooled to 15° C. was added diisopropylamine (DIEA, 1.02 mL) dropwise over a period of 5 minutes. The reaction mixture was then allowed to warm to room temperature and stirred for one hour to give compound 26, which was used without further purification. Compounds 40 kDa PEG di-amine hydrochloride (7.0 g, 0.175 mmol) and DIEA (0.061 mL) were added to the above solution and the resulting mixture stirred for 18 hrs at room temperature, followed by partial removal of the solvent under reduced pressure. The PEG derivative was precipitated by the addition of ethyl ether, filtered, and crystallized from IPA to yield 27 (5.6 g, 0.138 mmol, 79%). $^{13}$C NMR (67.8 MHz, $C_5D_5N$) δ 190.69, 162.10, 130.31, 128.21, 124.05, 123.57, 72.11-69.49 (PEG), 39.92, 15.72.

Example 19

Compound 28. To a solution of 27 (5.5 g, 0.14 mmol) in methanol (70 mL) cooled to 15° C. was added sodium borohydride (0.018 g, 0.45 mmol). The reaction mixture was allowed to warm to room temperature over a period of 2 hrs, followed by adjusting the pH to 6.5 with 1N HCl. The solvent was removed under reduced pressure, and the residue taken up in water. The pH was lowered to 2:0 with 0.5 N HCl, and the product extracted from the water with DCM. The organic layer was dried over anhydrous sodium sulfate, filtered, followed by partial removal of the solvent under reduced pressure. The product was precipitated with addition of ethyl ether, filtered, and washed with ethyl ether to yield 28 (4.7 g, 0.12 mmol, 85%). $^{13}$C NMR (67.8 MHz, $C_5D_5N$) δ 153.52, 130.12, 124.12, 121.33, 73.67-69.51 (PEG), 65.47, 39.91, 15.86.

Example 20

Compound 29. To a solution of 28 (4.0 g, 0.99 mmol) and DSC (0.41 g, 1.60 mmol) in anhydrous DCM (40 mL) and DMF (4 mL) cooled to 0° C. was added pyridine (0.125 g, 1.60 mmol). The reaction mixture was allowed to warm to room temperature and stirred for 12 hrs, followed by partial removal of the solvent under reduced pressure. The PEG linker was precipitated with addition of ethyl ether, filtered, and crystallized from DCM/ethyl ether to yield 29 (3.45 g, 0.85 mmol, 86%). $^{13}$C NMR (67.8 MHz, $CDCl_3$) δ 169.44, 151.34, 128.14, 126.65, 123.56, 72.38-68.90 (PEG), 41.52, 25.08, 15.79.

Example 21

Compound 30. Prepared in 86% yield by reacting 1 with 29 as described in Example 1 for preparation of 3, except that 2 is replaced by 29. $^{13}$C NMR (67.8 MHz, $C_5D_5N$) δ 174.44, 172.41, 170.65, 168.74, 166.18, 158.76, 157.45, 154.24, 152.74, 152.10, 148.09, 137.54, 128.77, 127.30, 90.29, 88.42, 78.84, 77.37, 76.43, 63.50, 62.66, 61.65, 60.74, 58.87, 56.99, 55.16, 54.20, 53.35, 52.81, 51.39, 35.64, 26.12, 25.26, 23.51, 22.30, 18.47, 17.43, 14.00.

Example 22

Compound 32. Prepared in 88% yield by reacting 1 with 31 as described in Example 1 for preparation of 3, except that 2 is replaced by 31. The structure is confirmed by $^{13}$C NMR.

Example 23

Compound 33. A solution of 2 (mw 40664, 1.53 g, 0.0377 mmol), 32 (0.50 g, 0.075 mmol) and DMAP (0.046 g, 0.375 mmol) in anhydrous DCM (50 mL) was stirred at room temperature for 12 hrs. The solvent was evaporated under reduced pressure, and the residue recrystallized from a mixture of IPA/DMF/TEA (48 mL:12 mL:0.2 mL) three times to give pure 33 (1.72 g, 0.032 mmol, 85%). $^{13}$C NMR (67.8 MHz, $C_5D_5N$) δ 173.18, 172.30, 169.05, 167.31, 162.73, 161.25, 156.41, 155.66, 144.90, 130.61, 129.39, 66.72, 59.01, 51.59, 41.98, 36.24, 31.35, 26.50, 23.68, 16.70.

Example 24

Compound 35. To a solution of compound 1 (0.106 g, 0.071 mmol) and DMAP (0.089 g, 0.729 mmol) in a mixture of anhydrous DMF:DCM (25 mL:25 mL) was added PEG linker 34 (mw 12332, 2.0 g, 0.162 mmol) and the resulting mixture stirred at room temperature for 12 hrs. The PEG derivative was precipitated with ethyl ether (200 mL), filtered, and the crude product recrystallized from a mixture of IPA/DMF (48 mL:12 mL) twice to give 35 (1.58 g, 0.610 mmol, 76%). The structure is confirmed by $^{13}$C NMR.

Example 25

Compound 37. Prepared in 91% yield by reacting 1 with 36, MW 5,000, as described in Example 1, for preparation of 3, except that 2 is replaced by 36. The structure is confirmed by $^{13}$C NMR.

Example 26

Compound 38. A solution of 2' PEG 20,000 (not 40,000) prepared the same way as that described in Example 1 for 2, (mw 20664, 4.44 g, 0.215 mmol), 37 (mw 5332, 2.73 g, 0.410 mmol) and DMAP (0.251 g, 2.05 mmol) in a mixture of anhydrous DCM:DMF (50 mL:50 mL) was stirred at room temperature for 12 hrs. The PEG derivative was precipitated by the addition of ethyl ether (300 mL), filtered, and the residue recrystallized from a mixture of ethanol:DMF:TEA (150 mL:150 mL:3.0 mL) twice to give 38 (6.82 g, 0.202 mmol, 94%). $^{13}$C NMR (67.8 MHz, $C_5D_5N$) δ 174.68, 171.94, 170.51, 168.73, 168.62, 162.35, 155.42, 141.02, 133.16, 132.06, 130.69, 130.37, 130.08, 128.45, 127.29, 78.08, 65.24, 63.77, 58.88, 54.48, 35.89, 31.02, 26.21, 25.28, 24.18, 23.46, 22.33, 18.29, 16.35.

Example 27

Compound 39. A solution of 2 (mw 40664, 3.84 g, 0.0945 mmol), 37 (mw 5332, 1.20 g, 0.180 mmol) and DMAP (0.251 g, 2.05 mmol) in a mixture of anhydrous DCM:DMF (60 mL:60 mL) was stirred at room temperature for 12 hrs. The PEG derivative was precipitated out with the addition of ethyl ether (300 mL), filtered, and the residue crystallized from a mixture of ethanol:DMF:TEA (150 mL:150 mL:1.2 mL) to give 39 (6.82 g, 0.202 mmol, 94%). The structure of the product is confirmed by $^{13}$C NMR.

Example 28

Compound 41. To a solution of 40 (4.0 g, 16.1 mmol) and triphosgene (1.92 g, 6.46 mmol) in anhydrous DCM (50 mL) cooled to 15° C. was added DIEA (7.6 mL, 43.6 mmol) dropwise over a period of 5 minutes, while maintaining the reaction temperature between 15° C. and 20° C. This mixture was allowed to warm to room temperature over a period of one hour, followed by the addition of 25 (1.97 g, 16.13 mmol) and DMAP (2.4 g, 16.1 mmol) and then stirred at room temperature overnight. The mixture was washed with 0.1N HCl solution, the organic layer dried (anhydrous sodium sulfate), filtered, and the solvent removed from the filtrate under reduced pressure to give crude 41. $^{13}$C NMR (67.8 MHz, CDCl$_3$) δ 191.18, 155.64, 152.99, 152.82, 133.42, 132.06, 129.76, 78.99, 41.00, 40.17, 28.21, 16.12.

Example 29

Compound 42. To a solution of 2 (1.0 g, 2.36 mmol) in methanol (30 mL) cooled to 15° C. was added sodium borohydride (0.1 g, 2.63 mmol) and the reaction mixture stirred at room temperature for one hour, followed by acidification with 0.1N HCl solution. The solvent was removed from the filtrate in vacuo, and the residue was taken up in water (20 mL) and extracted with DCM. The organic layer was dried (anhydrous sodium sulfate), filtered, and the solvent removed from the filtrate under reduced pressure. The crude product was then purified by silica gel chromatography to yield 42 (0.9 g, 90%). $^{13}$C NMR (67.8 MHz, CDCl$_3$) δ 155.65, 153.95, 146.81, 138.01, 130.33, 126.56, 78.86, 63.89, 40.69, 39.96, 28.09, 15.92.

Example 30

Compound 45. To a solution of 42 (0.9 g, 2.11 mmol) in DCM (57 mL) is added trifluoroacetic acid (3 mL) and the reaction mixture stirred for 1.5 hrs at room temperature, followed by removal of the solvent in vacuo to make 43. The residue is dissolved in anhydrous DCM (70 mL) and to this solution is added 44 (28.8 g, 0.72 mmol), prepared according to the aforementioned U.S. Pat. No. 5,643,575, and DMAP (1.26 g, 10.3 mmol). The mixture is cooled to 0° C. followed by the addition of EDC (0.56 g, 2.93 mmol), and the solution is allowed to warm to room temperature and stirred overnight followed by partial removal of the solvent under reduced pressure. The product is precipitated with ethyl ether, collected by filtration, and crystallized from DCM/ethyl ether to yield 45 (24.5 g, 85%). The structure of 45 is confirmed by $^{13}$C NMR.

Example 31

Compound 46. To a solution of 45 (6.2 g, 0.154 mmol) and DSC (0.315 g, 1.23 mmol) in a mixture of anhydrous DCM (120 mL) and DMF (12 mL) cooled to 0° C. is added pyridine (0.10 g, 1.23 mmol) and the mixture allowed to warm to room temperature and stirred overnight. The solvent is partially removed under reduced pressure and the product precipitated with ethyl ether, filtered, and crystallized from DCM/ethyl ether to give 46 (5.8 g, 89%). The structure of 46 is confirmed by $^{13}$C NMR.

Example 32

Compound 47. To a solution of 1 (0.138 g, 0.093 mmol) and triethylamine (TEA, 0.52 mL, 3.70 mmol) in DMF (50 mL) is added 46 (3 g, 0.074 mmol) and 5.5 g molecular sieves (4 Å) and the mixture stirred at 30° C. for 5 hrs. The reaction mixture is filtered through celite, the PEG conjugate precipitated with ether, filtered, and crystallized from DMF/ethanol (50:50) three times to give 47 (2.0 g, 0.0436 mmol, 59%).

Example 33

Compound 49. To a solution of 1 (0.276 g, 0.186 mmol) and triethylamine (TEA, 1.04 mL, 7.40 mmol) in DMF (50 mL) is added 48, prepared according to the aforementioned U.S. Ser. No. 10/218,167, (3 g, 0.148 mmol), mPEG 20,000 Da, and 5.5 g molecular sieves (4 Å) and the mixture stirred at 30° C. for 5 hrs. The reaction mixture is filtered through celite, the PEG conjugate precipitated with ether, filtered, and crystallized from DMF/ethanol (50:50) three times to give 49 (2.0 g, 0.0436 mmol, 59%).

Other embodiments of the invention will be apparent to one skilled in the art from a consideration of this specification or practice of the invention disclosed herein. It is intended that the specification and examples be considered as exemplary only, with the true scope and spirit of the invention being indicated by the following claims.

What is claimed:

1. A method of preparing a vancomycin-polymer conjugate wherein the polymer is conjugated to the suger amino group of a vancomycin, comprising:

reacting a vancomycin compound of the formula:

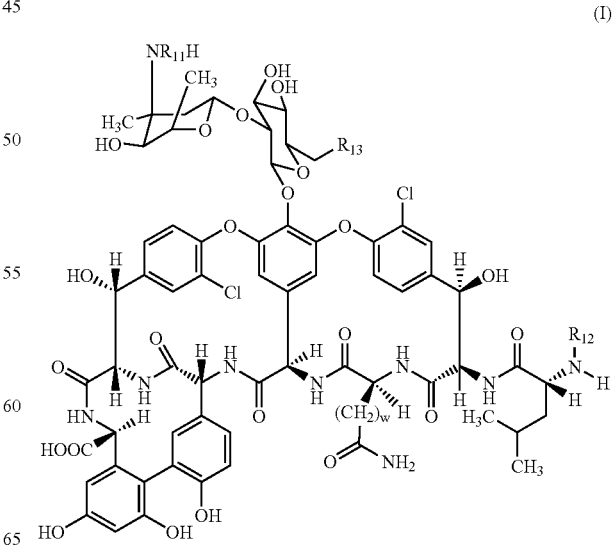

(I)

wherein
$R_{11}$ and $R_{12}$ are independently selected from the group consisting of hydrogen, $C_{1-6}$ alkyl[s], $C_{3-12}$ branched alkyl[s], $C_{3-8}$ cycloalkyl[s], $C_{1-6}$ substituted alkyl[s], $C_{3-8}$ substituted cycloalkyl[s], aryl[s], substituted aryl[s], aralkyl[s], $C_{1-6}$ heteroalkyl[s], substituted $C_{1-6}$ heteroalkyl[s], $C_{1-6}$ alkoxyalkyl, phenoxyalkyl and $C_{1-6}$ heteroalkoxy[s];

$R_{13}$ is OH, NH-aryl, NH-aralkyl, or NH—$C_{1-12}$ alkyl; and w is 1 or 2;

in the presence of at least about a ten-fold molar excess of triethylamine and a sufficient amount of dimethylformamide with a polyalkylene oxide residue containing at least one leaving group that reacts with the sugar amino group $NR_{11}H$ of said vancomycin compound.

2. The method of claim 1, wherein said polyalkylene oxide residue is activated, wherein the said activated polyalkylene oxide residue is selected from the group consisting of:

wherein:
$R_1$ and $R_2$ are independently selected from polyalkylene oxide residues;
$R'_1$ and $R'_2$ are independently selected from branched polyalkylene oxide residues;
$Y_{1-6}$ are independently selected from the group consisting of O, S or $NR_9$;
$R_{3-10}$ are independently selected from the group consisting of hydrogen, $C_{1-6}$ alkyl, $C_{3-12}$ branched alkyl, $C_{3-8}$ cycloalkyl, $C_{1-6}$ substituted alkyl, $C_{3-8}$ substituted cyloalkyl, aryl, substituted aryl, aralkyl, $C_{1-6}$ heteroalkyl, substituted $C_{1-6}$ heteroalkyl, $C_{1-6}$ alkoxyalkyl, phenoxyalkyl and $C_{1-6}$ heteroalkoxy;
Ar is a moiety which forms a multi-substituted aromatic hydrocarbon or a multi-substituted heterocyclic group;
$L_1$ and $L_2$ are independently selected from bifunctional linkers;
$B_1$ and $B_2$ are independently selected from leaving groups;

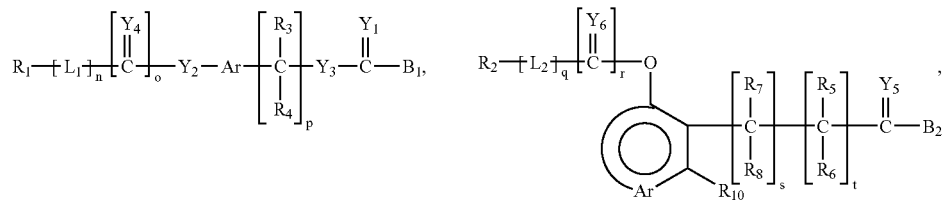

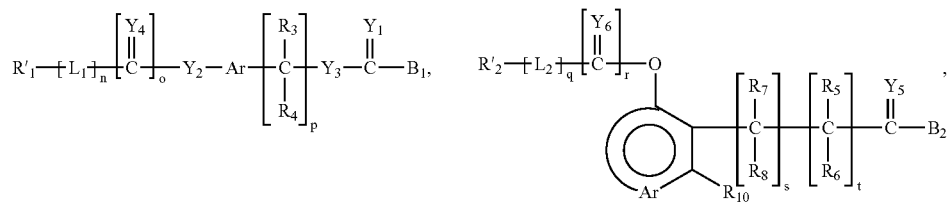

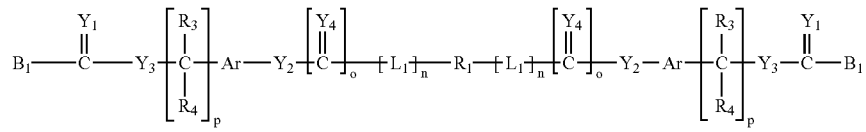

and

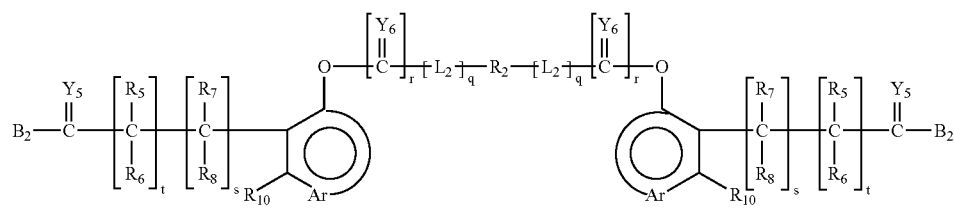

p and t are independently selected from positive integers;

n, q and s are independently either zero or a positive integer; and o and r are independently zero or one.

3. The method of claim 2, wherein said activated polyalkylene oxide residue is selected from the group consisting of

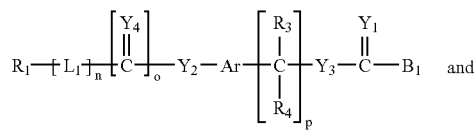

and

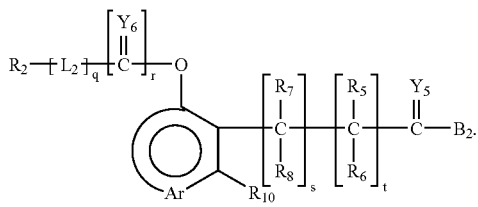

4. The method of claim 1, wherein said polyalkylene oxide residue is activated, and wherein said activated polyalkylene oxide is selected from the group consisting of:

(Ia)
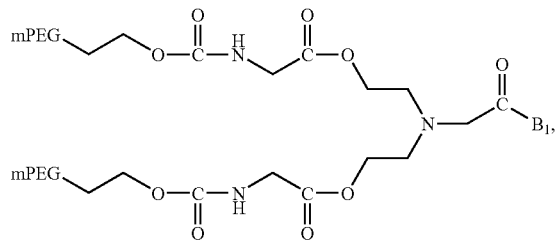

(Ib)
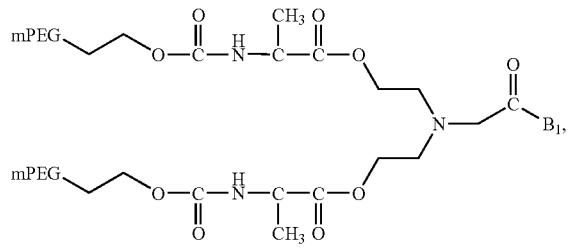

(Ic)
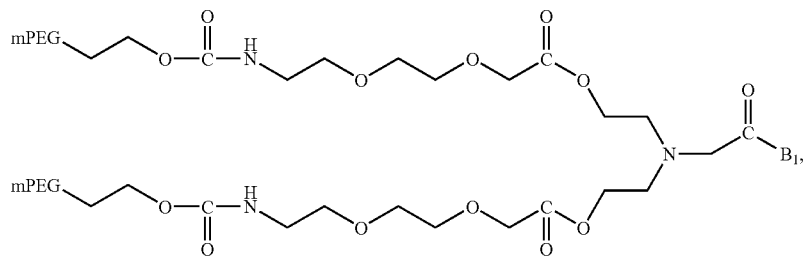

(Id)
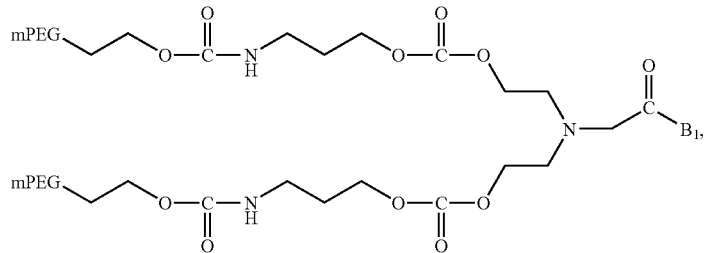

(Ie)
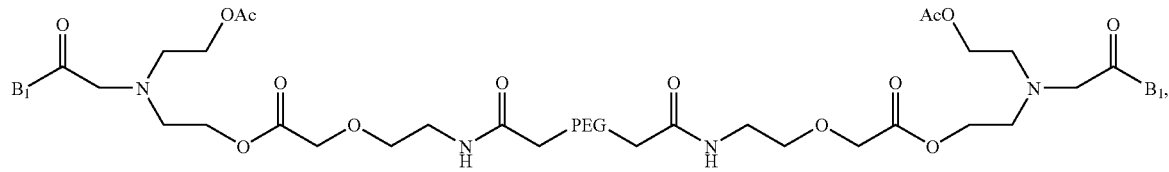

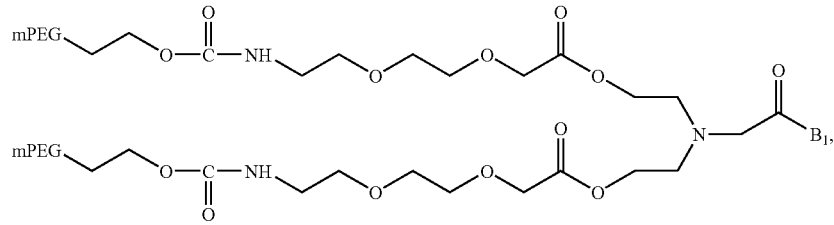
(If)
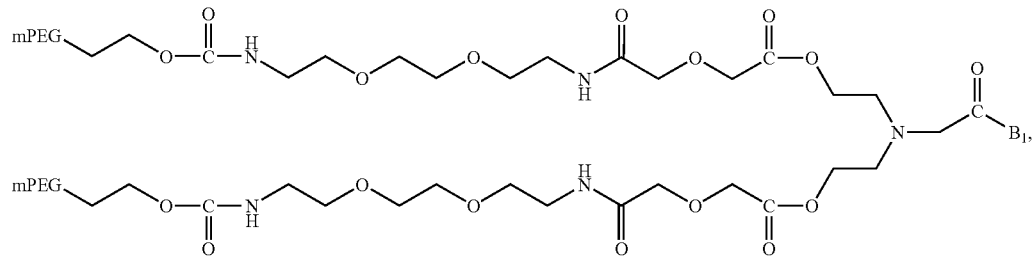
(Ig)
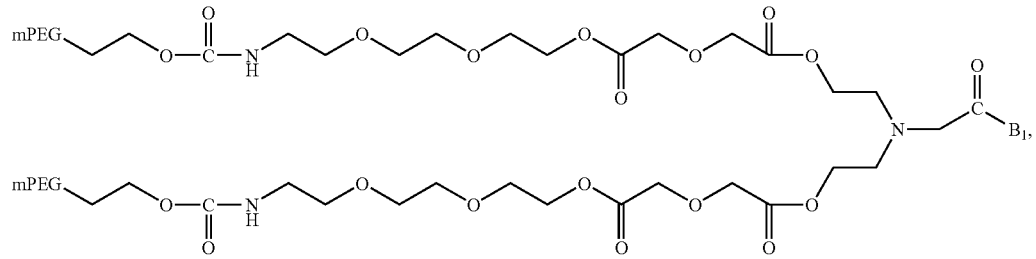
(Ih)
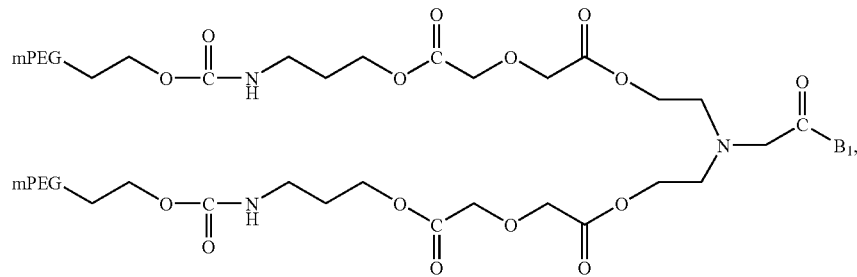
(Ii)
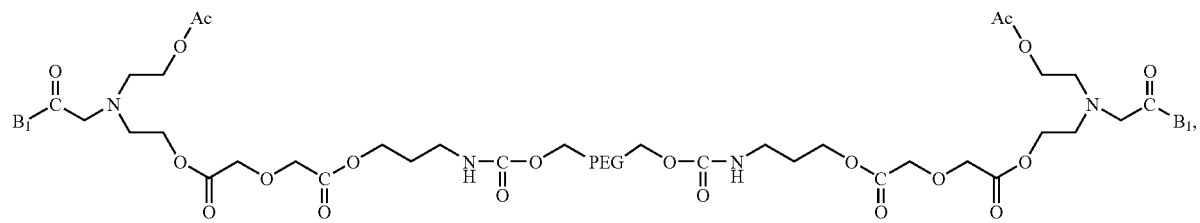
(Ij)
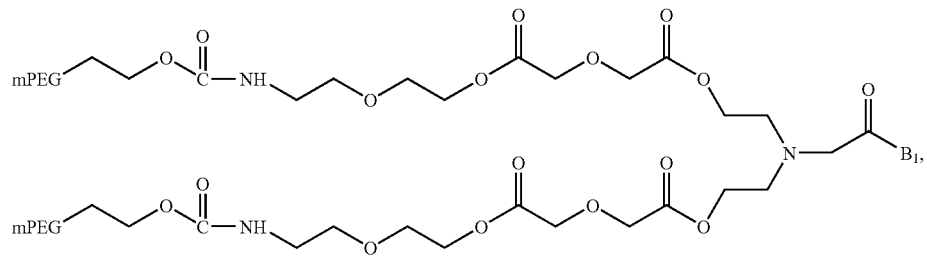
(Ik)

-continued
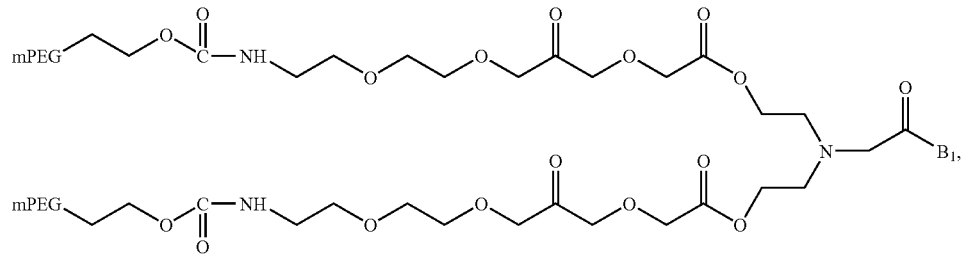
(Il)
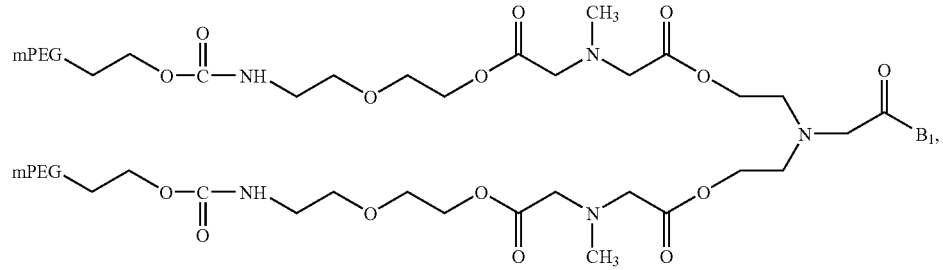
(Im)
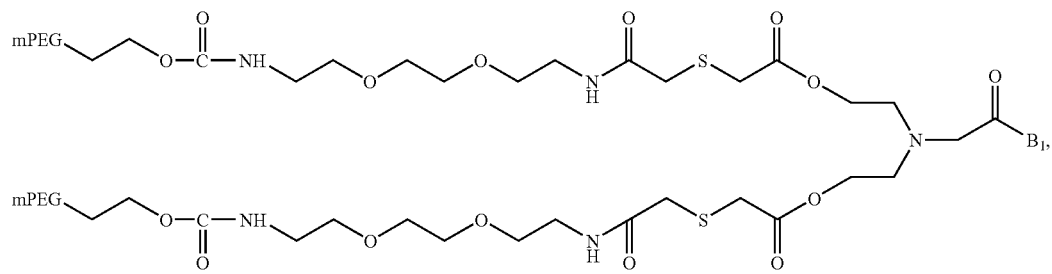
(In)
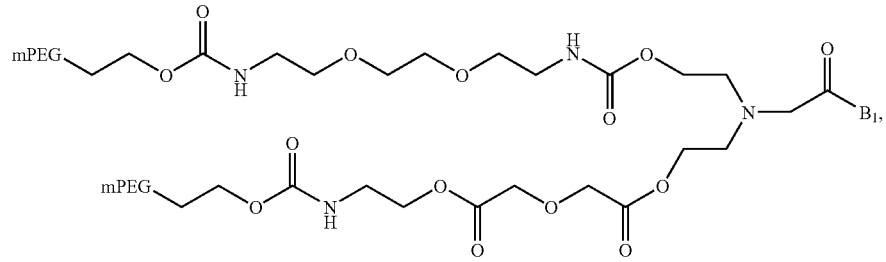
(Io)
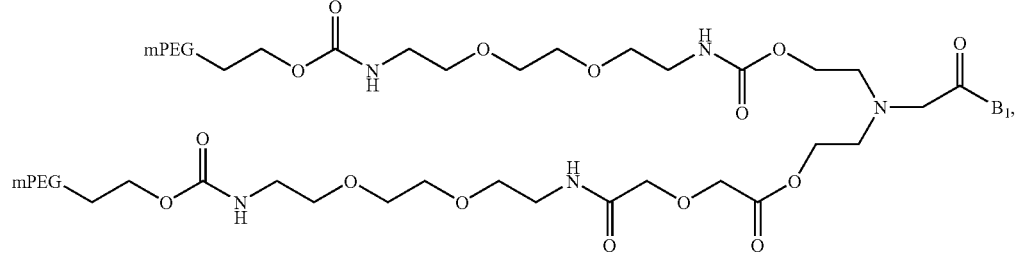
(Ip)
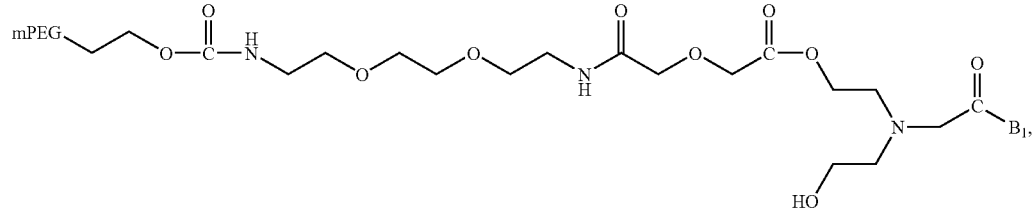
(Iq)

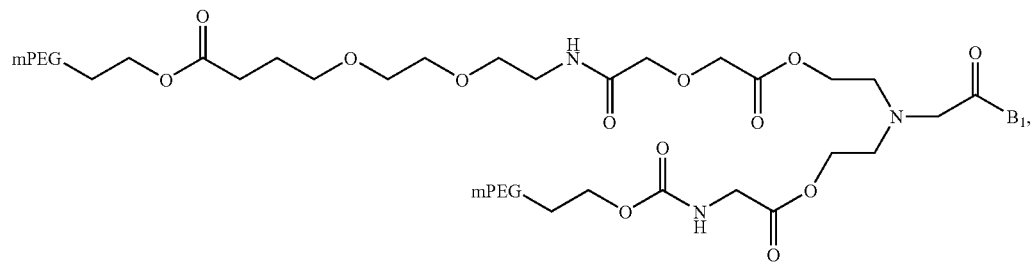
(Ir)
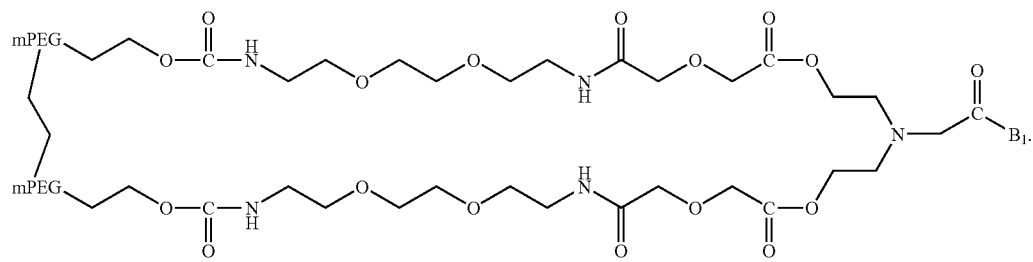
(Is)
wherein $B_1$ is selected from the group consisting of:
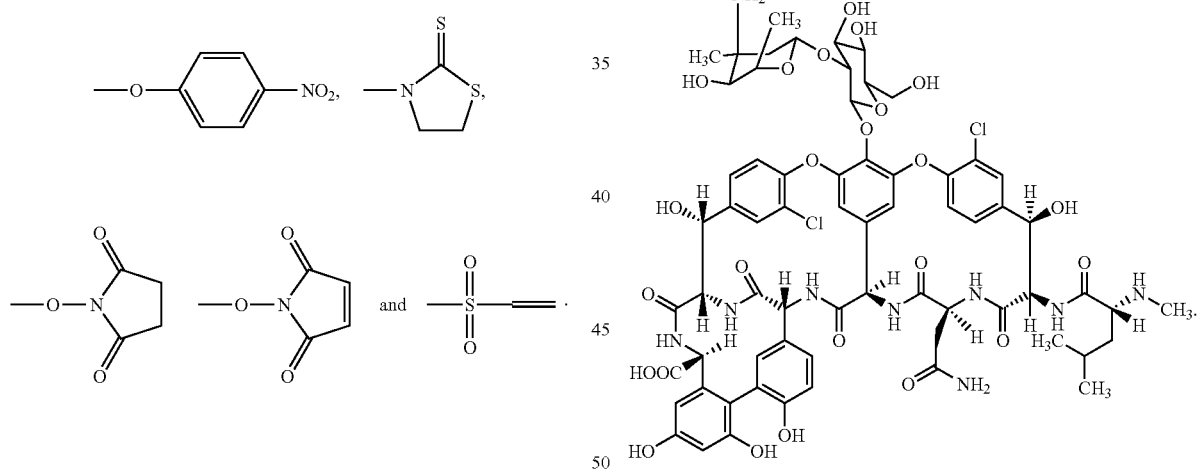
5. The method of claim 1, wherein said vancomycin compound is:
6. The method of claim 2, wherein said vancomycin polymer conjugate is selected from the group consisting of
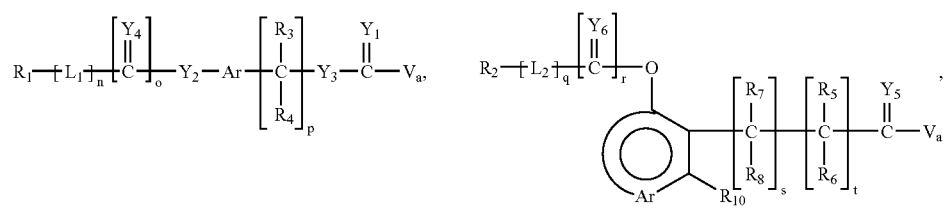

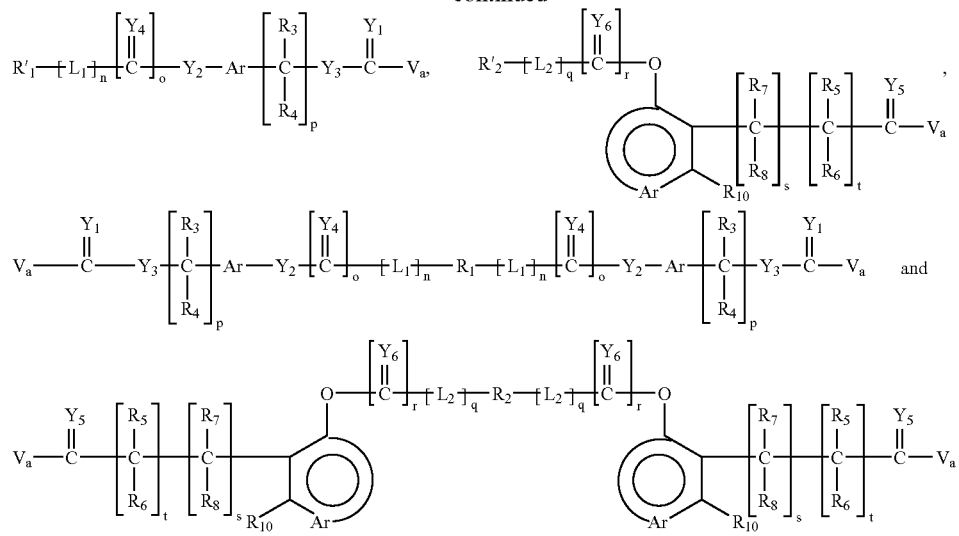
wherein $V_a$ is
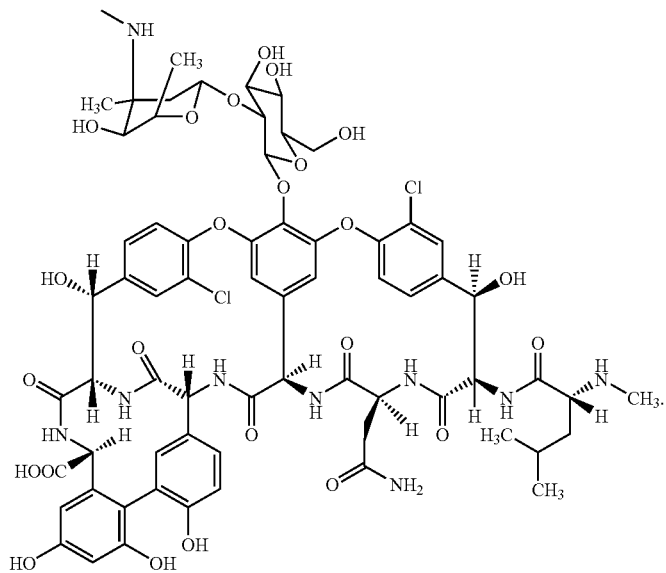
7. The method of claim 1, wherein said polyalkylene oxide containing said leaving group is selected from the group consisting of
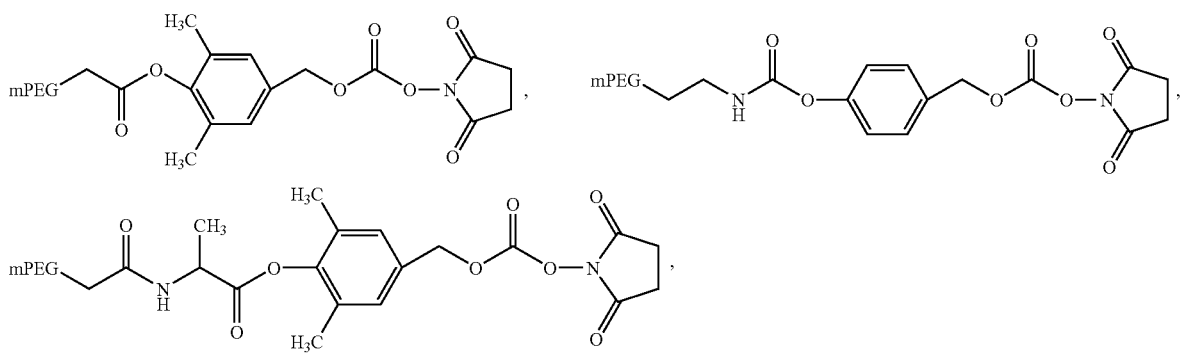

-continued
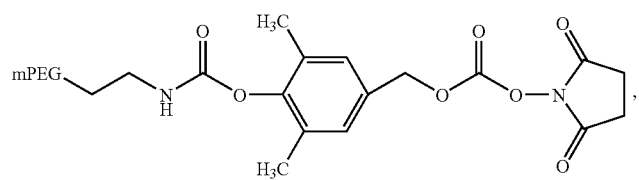
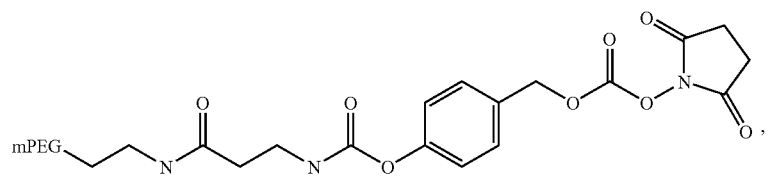
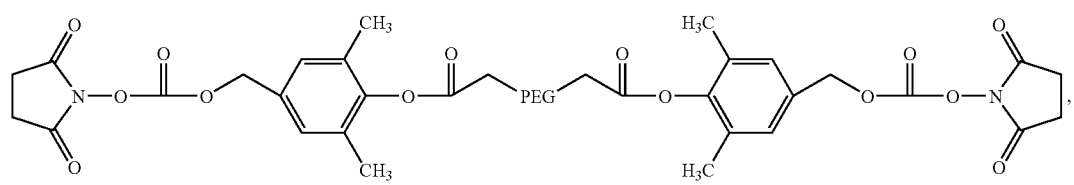
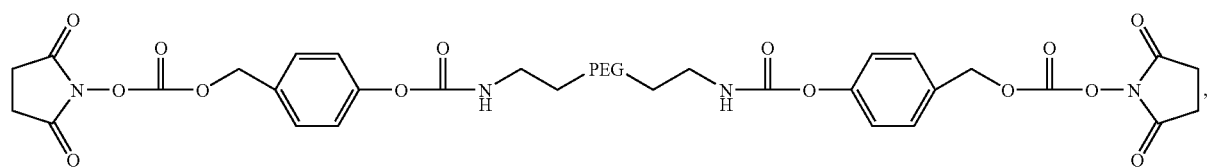
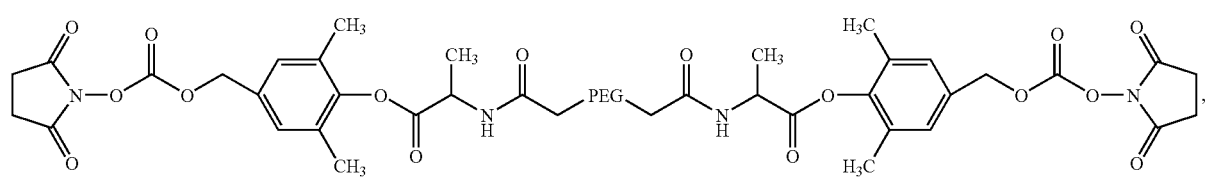
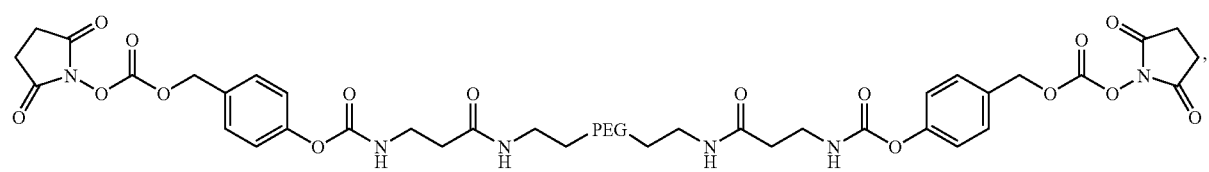
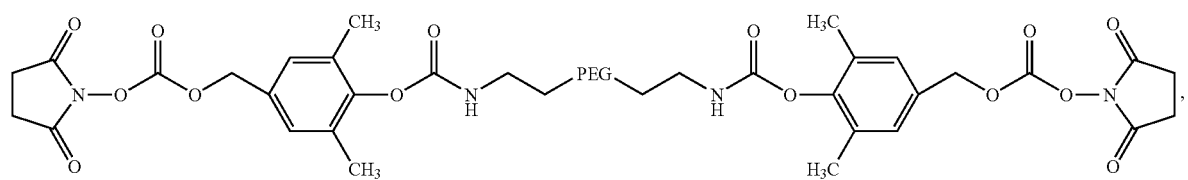
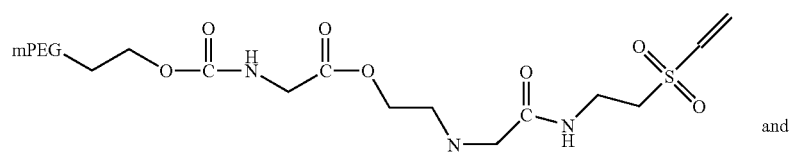 and
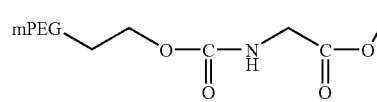

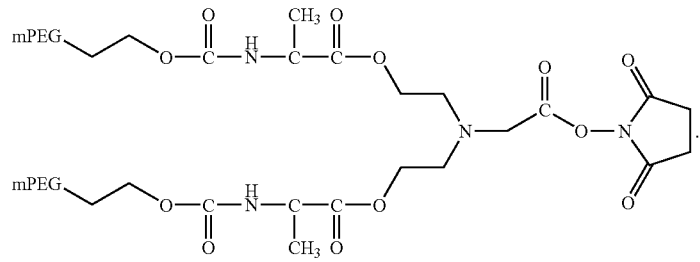
8. The method of claim 2, wherein $R_1$ and $R_2$ are independently selected from polyethylene glycol residues and $R'_1$ and $R'_2$ are independently selected from branched polyethylene glycol residues.
9. The method of claim 1, wherein said vancomycin-polymer conjugate is selected from the group consisting of
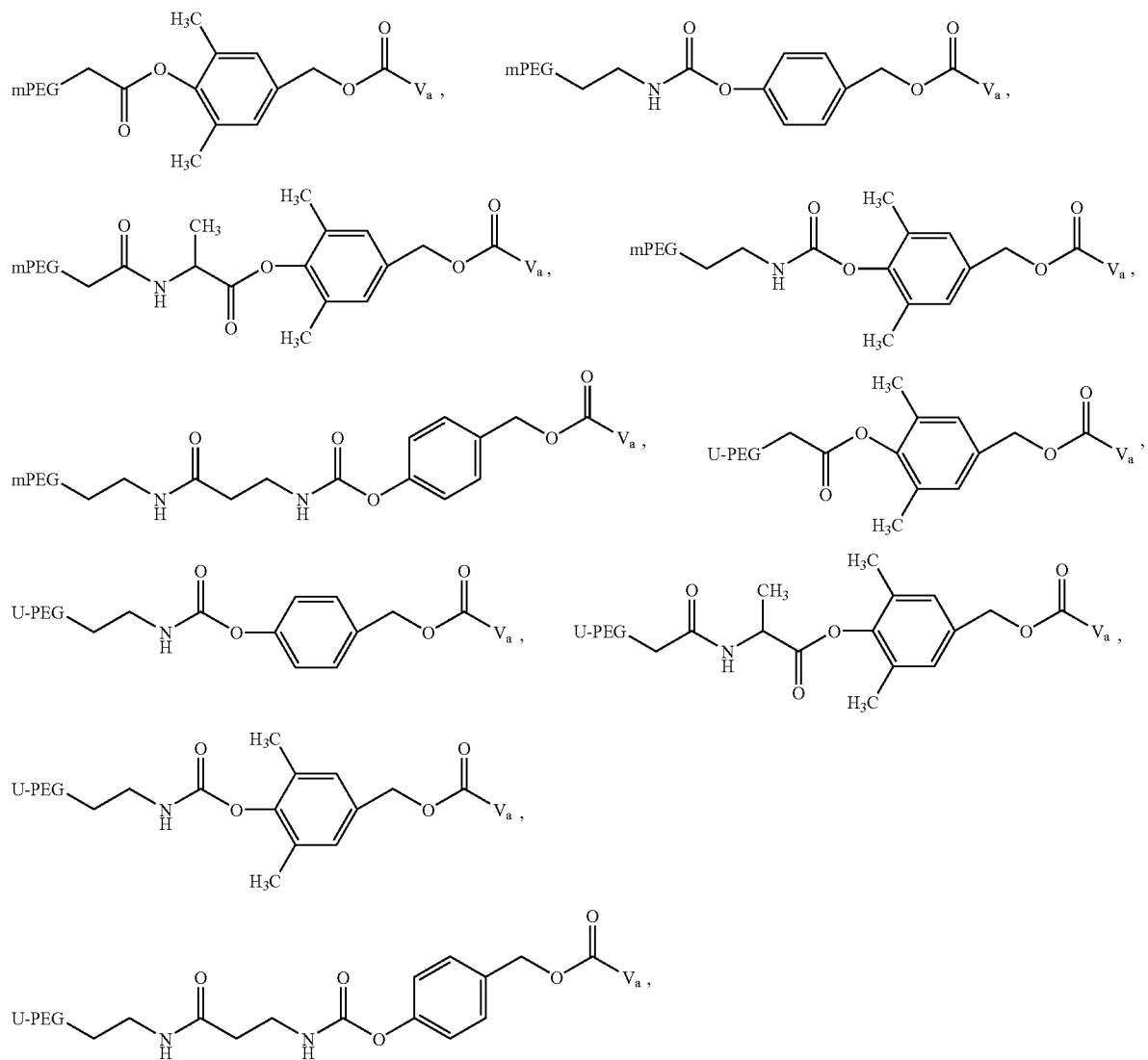

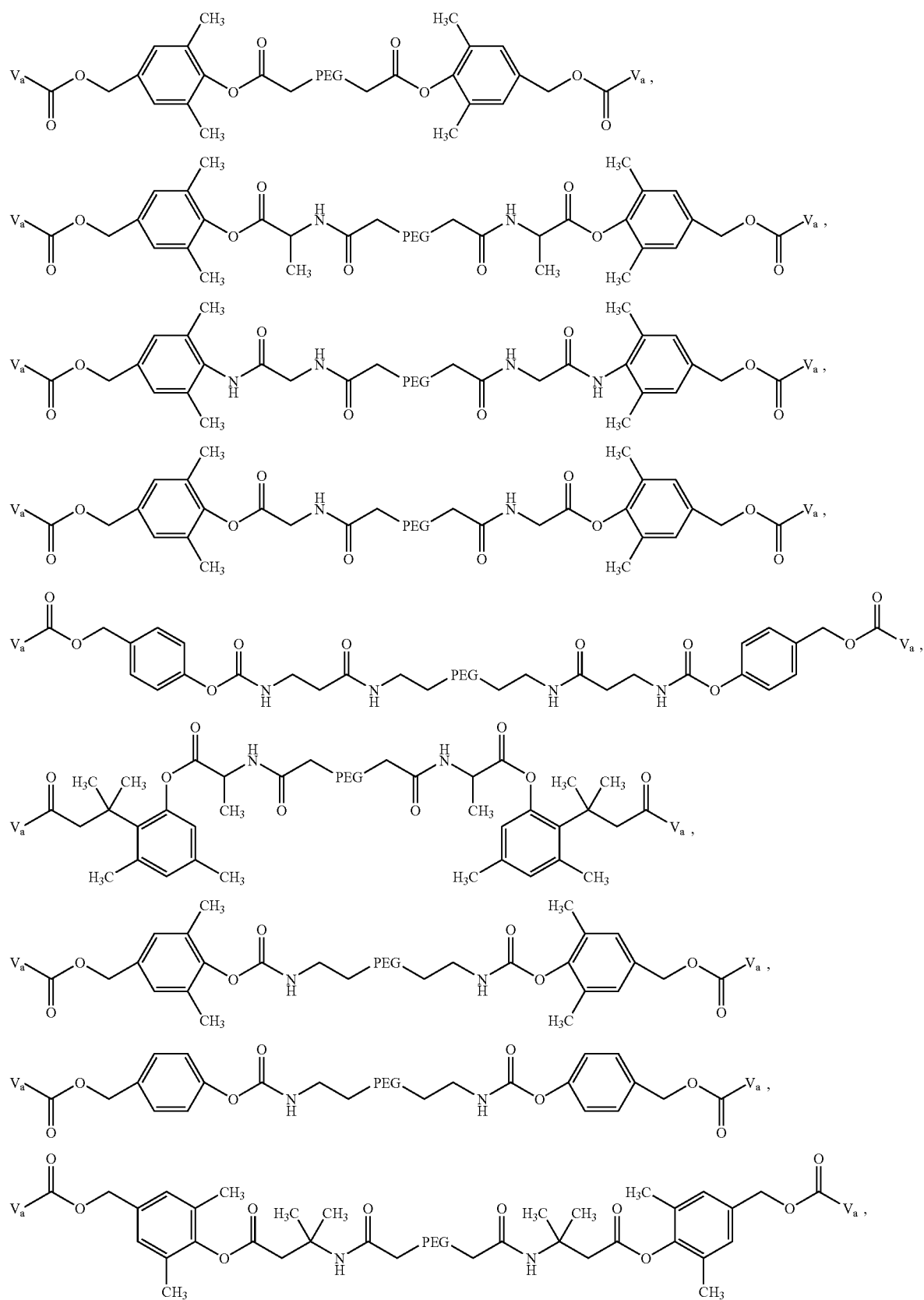

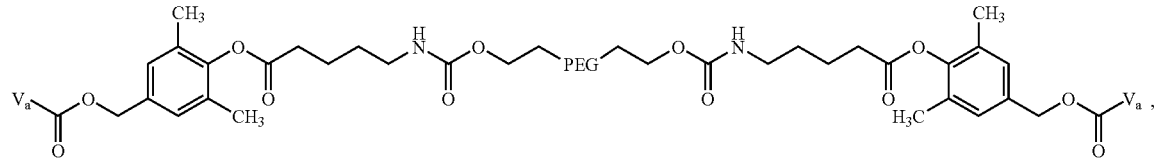
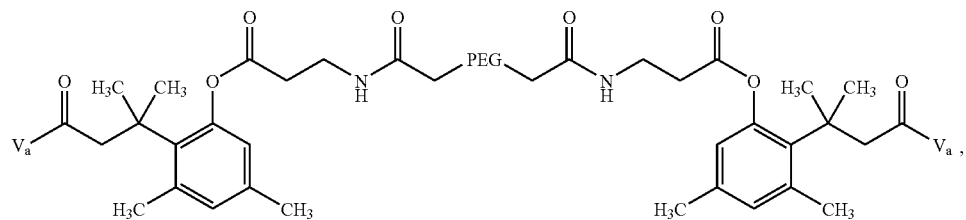
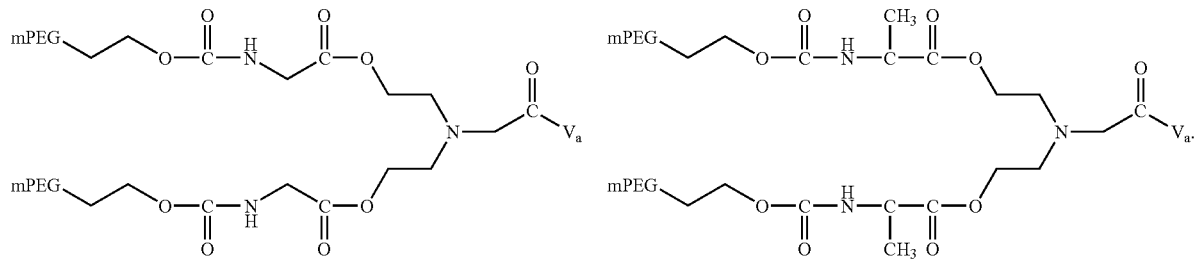
wherein
PEG is —O(—CH$_2$CH$_2$O)$_x$—;
mPEG is H$_3$CO(—CH$_2$CH$_2$O)$_x$—;
x is a positive integer selected from about 10 to about 2300, and
U-PEG is selected from the group consisting of
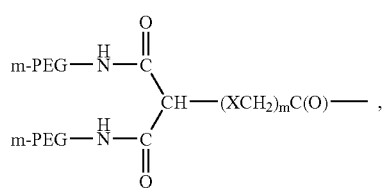
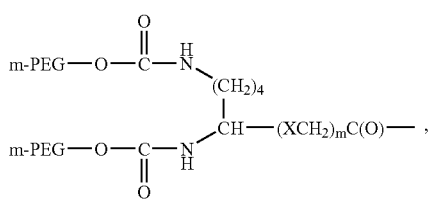
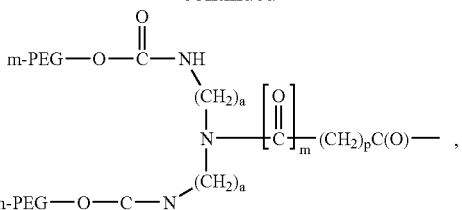
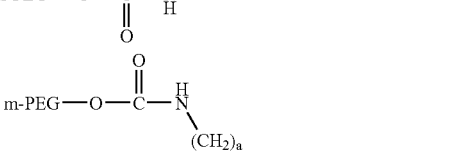
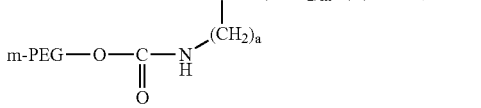, and
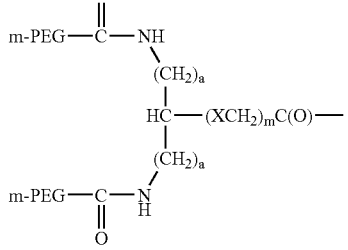

-continued $V_a$ is

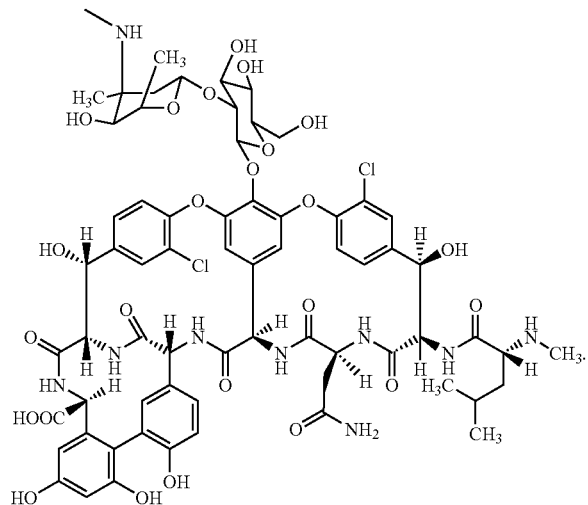

10. The method of claim 1, wherein said molar excess of triethylamine is at least about 30-fold.

11. The method of claim 1, wherein said molar excess of triethylamine is at least about 20-fold.

12. The method of claim 1, wherein said sufficient amount of dimethylformamide ranges from about 10 ml/g vancomycin to about 500 ml/g vancomycin.

13. The method of claim 1, wherein said sufficient amount of dimethylformamide ranges from about 100 ml/g vancomycin to about 200 ml/g vancomycin.

14. The method of claim 4, wherein said vancomycin polymer conjugate is selected from the group consisting of

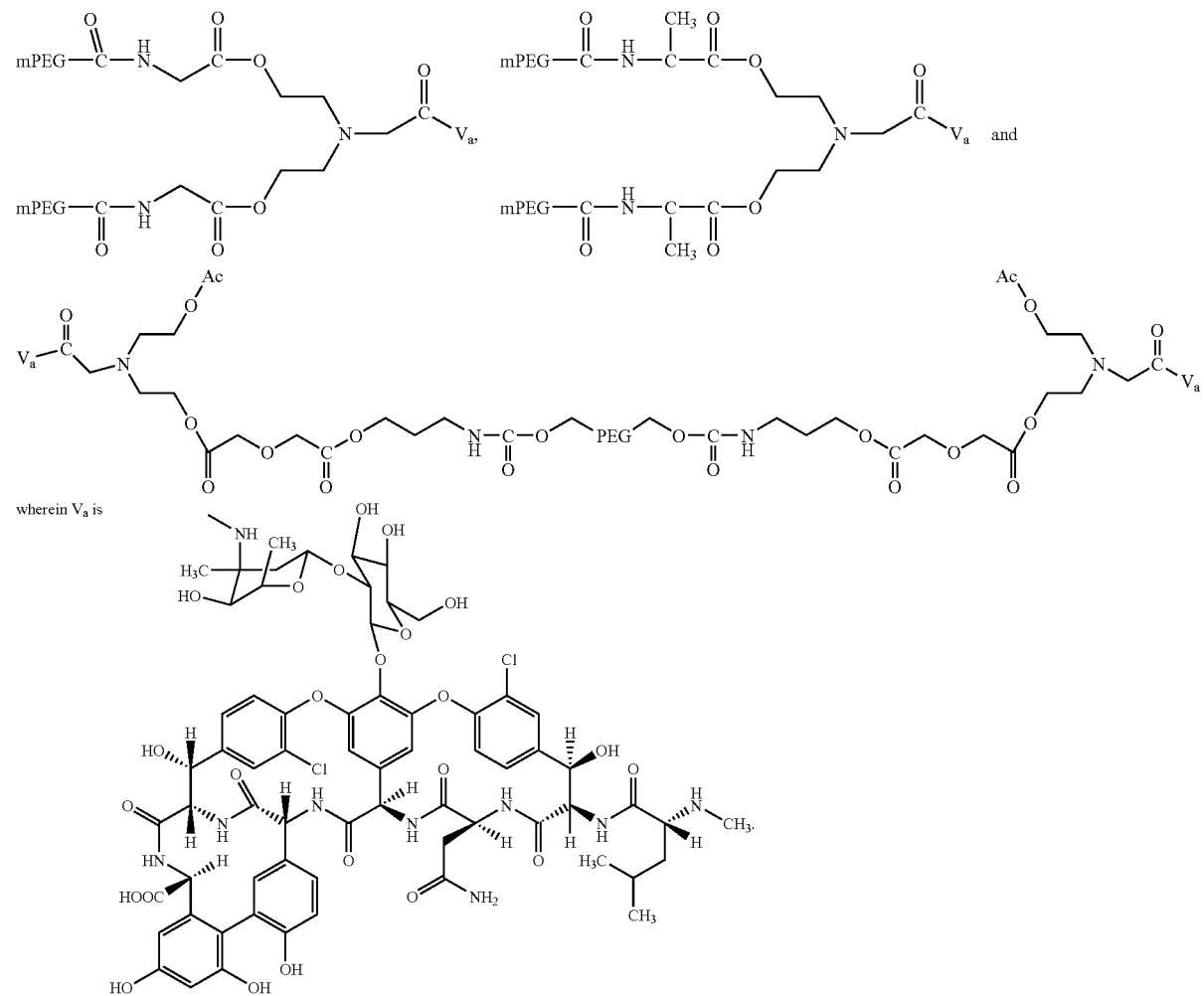

* * * * *

UNITED STATES PATENT AND TRADEMARK OFFICE
CERTIFICATE OF CORRECTION

PATENT NO. : 7,273,845 B2
APPLICATION NO. : 10/705743
DATED : September 25, 2007
INVENTOR(S) : Hong Zhao et al.

It is certified that error appears in the above-identified patent and that said Letters Patent is hereby corrected as shown below:

Column 53, line 17:
"wherein the said" should read --wherein said--

Column 54, lines 6-7:
"the group consisting of O, S or NR$_9$" should read --the group consisting of O, S and NR$_9$--

Column 65:
the second compound should appear as follows:

-- 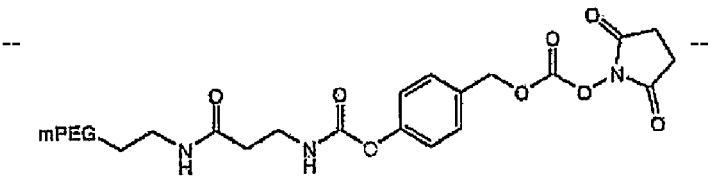 --

Column 71, line 35:
the word "and" and the following compound should appear below the third compound and above the word "wherein"

-- 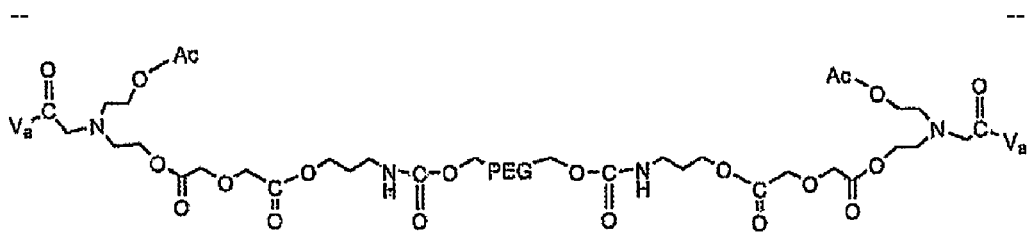 --

Signed and Sealed this

Fourth Day of December, 2007

JON W. DUDAS
*Director of the United States Patent and Trademark Office*